US010639299B2

(12) United States Patent
Yang et al.

(10) Patent No.: US 10,639,299 B2
(45) Date of Patent: May 5, 2020

(54) CALCIUM SENSING RECEPTORS, LIGANDS, COMPOSITIONS, AND METHODS OF USE

(71) Applicants: Georgia State University Research Foundation, Inc., Atlanta, GA (US); University of Georgia Research Foundation, Inc., Athens, GA (US); Board of Trustees of Michigan State University, East Lansing, MI (US)

(72) Inventors: Jenny Jie Yang, Marietta, GA (US); Jian Hu, Atlanta, GA (US); Edward Brown, Atlanta, GA (US); Kelley Moremen, Athens, GA (US)

(73) Assignees: Georgia State University Research Foundation, Inc., Atlanta, GA (US); University of Georgia Research Foundation, Inc., Athens, GA (US); Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 16/090,380

(22) PCT Filed: Mar. 29, 2017

(86) PCT No.: PCT/US2017/024789
§ 371 (c)(1),
(2) Date: Oct. 1, 2018

(87) PCT Pub. No.: WO2017/172944
PCT Pub. Date: Oct. 5, 2017

(65) Prior Publication Data
US 2019/0111032 A1 Apr. 18, 2019

Related U.S. Application Data

(60) Provisional application No. 62/314,707, filed on Mar. 29, 2016.

(51) Int. Cl.
*A61K 31/435* (2006.01)
*A61K 31/437* (2006.01)
*G01N 33/68* (2006.01)
*G01N 33/50* (2006.01)
*C07K 16/18* (2006.01)
*C07K 14/705* (2006.01)

(52) U.S. Cl.
CPC .......... *A61K 31/437* (2013.01); *C07K 14/705* (2013.01); *C07K 16/18* (2013.01); *G01N 33/50* (2013.01); *G01N 33/6872* (2013.01); *G01N 2500/02* (2013.01)

(58) Field of Classification Search
CPC .................................................. A61K 31/435
USPC ...................................................... 514/292
See application file for complete search history.

(56) References Cited

U.S. PATENT DOCUMENTS 6,069,150 A * 5/2000 Spinelli ............... A61K 31/437
514/312
2003/0166540 A1 9/2003 Feder et al.
2004/0030100 A1 2/2004 Xiao

FOREIGN PATENT DOCUMENTS

WO 2015156402 A1 10/2015

OTHER PUBLICATIONS

International Search Report and Written Opinion for PCT/US2017/024789 dated Sep. 8, 2017.
Zhang, et al. "Indentification of an L-Phenylalanine Binding Site Enhancing the Cooperative Responses of the Calcium-sensing Receptor to Calcium." J. Biol. Chem. 2014; 289(8): 5296-5309.
D'Souza-Li, et al. "Identification and Functional Characterization of Novel Calcium-Sensing Receptor Mutations in Familial Hypocalciuric Hypercalcemia and Autosomal Dominant Hypocalcemia." J. Clin. Endocrin. Metab. 2002; 87(3): 1309-1318.
Huang, et al. "Identification and Dissection of Ca2+-Binding Sites in the Extracellular Domain of Ca2+-Sensing Receptor." J. Biol. Chem. 2007; 282(26): 1-22.
Zhang, et al. "Structural Basis for Regulation of Human Calcium-Sensing Receptor by Magnesium Ions and Unexpected Tryptophan Derivative Co-agonist." Sci. Adv. 2016; 2(5): 1-9.
Breitwieser, G.E., Calcium sensing receptors and calcium oscillations: calcium as a first messenger. Curr Top Dev Biol, 2006. 73: p. 85-114.
Brown, E.M. and R.J. MacLeod, Extracellular calcium sensing and extracellular calcium signaling. Physiol Rev, 2001. 81(1): p. 239-297.
Brown, E.M., et al., Cloning and characterization of an extracellular Ca(2+)-sensing receptor from bovine parathyroid. Nature, 1993. 366(6455): p. 575-80.
Wellendorph, P. and H. Brauner-Osborne, Molecular basis for amino acid sensing by family C G-protein-coupled receptors. Br J Pharmacol, 2009. 156(6): p. 869-84.
Brown, E.M., et al., Extracellular calcium potentiates the inhibitory effects of magnesium on parathyroid function in dispersed bovine parathyroid cells. Metabolism, 1984. 33(2): p. 171-6.
Buchan, A.M., et al., Mechanism of action of the calcium-sensing receptor in human antral gastrin cells. Gastroenterology, 2001. 120(5): p. 1128-39.
Conigrave, A.D. and D.R. Hampson, Broad-spectrum L-amino acid sensing by class 3 G-protein-coupled receptors. Trends Endocrinol Metab, 2006. 17(10): p. 398-407.

(Continued)

*Primary Examiner* — Raymond J Henley, III
(74) *Attorney, Agent, or Firm* — Thomas|Horstemeyer, LLP

(57) ABSTRACT

Described herein are compounds that can bind CaSR and/or a CaSR extracellular domain and formulations thereof. Also described herein are methods of inhibiting CaSR and/or treating a disease or disorder associated with a mutation in CaSR by administering a compound or formulation thereof described herein. Also described herein are assays that can be used to identify compounds that can bind an extracellular domain of CaSR.

16 Claims, 46 Drawing Sheets

Specification includes a Sequence Listing.

(56) References Cited

OTHER PUBLICATIONS

Conigrave, A.D. and D.R. Hampson, Broad-spectrum amino acid-sensing class C G-protein coupled receptors: molecular mechanisms, physiological significance and options for drug.
Conigrave, A.D., et al., L-amino acid sensing by the calcium-sensing receptor: a general mechanism for coupling protein and calcium metabolism? Eur J Clin Nutr, 2002. 56(11): p. 1072-80.
Conigrave, A.D., S.J. Quinn, and E.M. Brown, L-amino acid sensing by the extracellular Ca2+-sensing receptor. Proc Natl Acad Sci U S A, 2000. 97(9): p. 4814-9.
Davey, A.E., et al., Positive and negative allosteric modulators promote biased signaling at the calcium-sensing receptor. Endocrinology, 2012, 153(3): p. 1232-41.
EE, M., et al., A Ca(2+)-sensing receptor mutation causes hypoparathyroidism by increasing receptor sensitivity to Ca2+ and maximal signal transduction. Pediatric Research 1997 42: 443-447.
H. Minami et al.,"Direct Determination of Silicon in Powdered Aluminium Oxide by use of Slurry Sampling with in Situ Fusion Graphite-Furnace Atomic-Absorption Spectrometry." Fresenius' Journal of Analytical Chemistry 370, 855 (2001).
Hannan, F.M., et al., Identification of 70 calcium-sensing receptor mutations in hyper- and hypo-calcaemic patients: evidence for clustering of extracellular domain mutations at calcium-binding sites. Hum Mol Genet, 2012. 21(12): p. 2768-78.
J. A. Monn et al.,"Synthesis and Pharmacological Characterization of C4-Disubstituted Analogs of 1S,2S,5R,6S-2-Aminobicyclo[3.1.0]hexane-2,6-dicarboxylate: Identification of a Potent, Selective Metabotropic Glutamate Receptor Agonist and Determination of Agonist-Bound Human mGlu2 and mGlu3 Amino Terminal Domain Structures" J. Med. Chem. 58, 1776 (2015).
Jacobsen, S.E., et al., Delineation of the GPRC6A receptor signaling pathways using a mammalian cell line stably expressing the receptor. J Pharmacol Exp Ther, 2013. 347(2): p. 298-309.
Kenakin, T. and A. Christopoulos, Measurements of ligand bias and functional affinity. Nat Rev Drug Discov, 2013. 12 (6): p. 483.
L. Meng et al., "Enzymatic Basis for N-Glycan Sialylation" J. Biol. Chem. 288, 34680 (2013).
M. D. Winn et al., "Overview of the CCP4 Suite and Current Developments" Acta Crystallogr. 67, 235 (2011).
Nemeth, E.F. and W.G. Goodman, Calcimimetic and Calcilytic Drugs: Feats, Flops, and Futures. Calcif Tissue Int, pp. 341-358 2015.
P, C., et al., Characterization of 25 calcium-sensing receptor mutations in disorders of calcium homeostasis. Society for Endocrinology. BES Endocrine 2007 Abstracts 13: p. 1.
P. D. Adams et al., "PHENIX: A Comprehensive Python-Based System for Macromolecular Structure Solution" Acta Crystallogr. 66, 213 (2010).
P. Emsley; et al, "Features and Development of Coot" Acta Crystallogr. 66, 486 (2010).
S. Pidasheva, et al, "CASRdb: Calcium-Sensing Receptor Locus-Specific Database for Mutations Causing Familial (Benign) Hypocalciuric Hypercalcemia, Neonatal Severe Hyperparathyroidism, and Autosomal Dominant Hypocalcemia" Hum. Mutat. 24, 107 (2004).
S. J. Quinn et al., "CaSR-Mediated Interactions Between Calcium and Magnesium Homeostasis in Mice" Am. J. Physiol. Endocrinol. Metab. 304, E724 (2013).
Schachter, H., "Biosynthetic Controls that Determine the Branching and Microheterogeneity of Protein-Bound Oligosaccharides." Biochem Cell Biol, 1986. 64(3): p. 163-81.
T. Herraiz, et al, "L-Tryptophan Reacts with Naturally Occurring and Food-Occurring Phenolic Aldehydes to Give Phenolic Tetrahydro-â-carboline Alkaloids: Activity as Antioxidants and Free Radical Scavengers" J. Agric. Food Chem. 51, 2168 (2003).
W. Yang, et al, "Structural Analysis, Identification, and Design of Calcium-Binding Sites in Proteins" Proteins 47, p. 344-356 (2002).
Y. Geng, et al, "Structural Mechanism of Ligand Activation in Human GABAB Receptor" Nature 504, 254 (2013).
Yang, W., et al., The effects of ca(2+) binding on the dynamic properties of a designed ca(2+)-binding protein(,). Biochemistry, 2005. 44(23): p. 8267-73.
Young, S.H. and E. Rozengurt, Amino acids and Ca2+ stimulate different patterns of Ca2+ oscillations through the Ca2+-sensing receptor. Am J Physiol Cell Physiol, 2002. 282(6): p. C1414-22.
Zhang, C., et al., "Direct determination of multiple ligand interactions with the extracellular domain of the calcium-sensing receptor." J Biol Chem, 2014. 289(48): p. 33529-42.
Zhang, C., et al., "Role of Ca2+ and L-Phe in regulating functional cooperativity of disease-associated "toggle" calcium-sensing receptor mutations." PLoS One, 2014. 9(11): p. e113622.
Yang, W., et al., Rational design of a calcium-binding protein. J Am Chem Soc, 2003. 125(20): p. 6165-71.
Ye, Y., et al., Metal binding affinity and structural properties of an isolated EF-loop in a scaffold protein. Protein Eng, 2001. 14(12): p. 1001-13.
Tang, S., et al., Design and application of a class of sensors to monitor Ca2+ dynamics in high Ca2+ concentration cellular compartments. Proc Natl Acad Sci U S A, 2011. 108(39): p. 16265-70.

\* cited by examiner

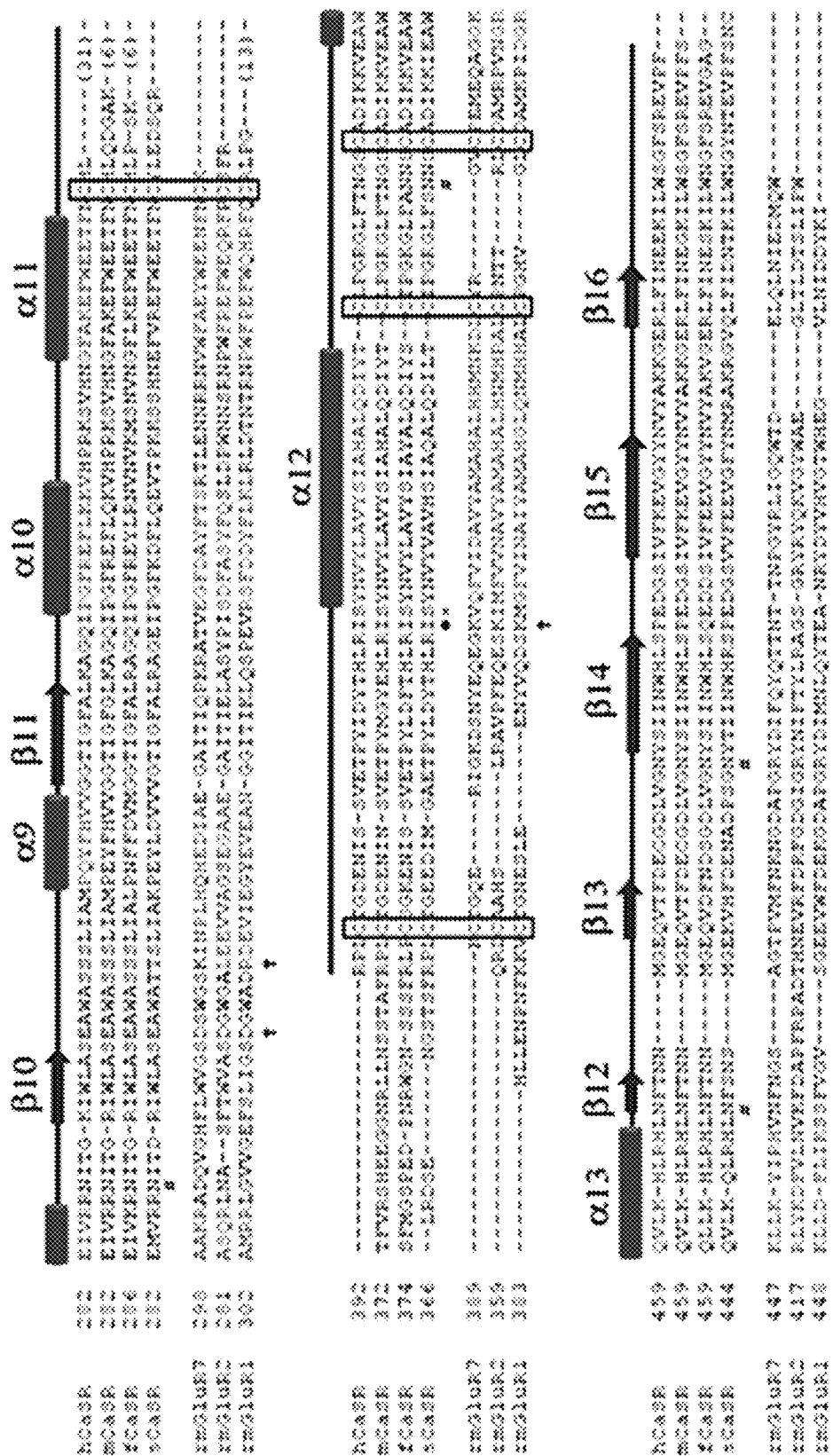
Fig. 1-cont'd

1. Reducing
2. Non-reducing

| Co-activators | EC$_{50}$ of [Mg$^{2+}$]$_o$ |
|---|---|
| 0.5 mM [Ca$^{2+}$]$_o$ | 7.2 ± 0.39 |
| 0.5 mM [Ca$^{2+}$]$_o$ + 0.0001 mM TNCA | 6.7 ± 0.25 |
| 0.5 mM [Ca$^{2+}$]$_o$ + 0.001 mM TNCA | 5.7 ± 0.47 |
| 0.5 mM [Ca$^{2+}$]$_o$ + 0.01 mM TNCA | 5.5 ± 0.27 |
| 0.5 mM [Ca$^{2+}$]$_o$ + 0.1 mM TNCA | 4.8 ± 0.24 |
| 0.5 mM [Ca$^{2+}$]$_o$ + 0.5 mM TNCA | 3.3 ± 0.70 |

FIG. 6

| Crystal | hCaSR-ECD | hCaSR-ECD/Gd$^{3+}$ |
|---|---|---|
| Data Collection | | |
| Wavelength (Å) | 0.9785 | 1.6985 |
| Space group | C2 | C2 |
| Cell Dimensions (Å) | a=170.9, b=82.9, c=94.3 α=γ=90°, β=105.1° | a=172.1, b=83.1, c=94.5 α=γ=90°, β=105.2° |
| $^1$Resolution (Å) | 40-2.1 (2.16-2.1) | 40-2.7 (2.8-2.7) |
| $^1$Redundancy | 3.8 (3.8) | 3.6 (3.6) |
| $^1$Completeness (%) | 100.0 (100.0) | 98.9 (99.9) |
| $^1$I/σI | 18.1 (1.5) | 12.0 (2.8) |
| $^{1,2}$R$_{merge}$ | 0.072 (0.913) | 0.093 (0.772) |
| $^{1,3}$R$_{pim}$ | 0.043 (0.541) | 0.058 (0.468) |
| $^§$CC$_{1/2}$ of the highest resolution shell | 0.631 | 0.645 |
| Refinement | | |
| Unique reflections | 74,544 | 34,777 |
| Number of Atoms | | |
|   Protein | 7,449 | 7,264 |
|   TNCA | 32 | 32 |
|   Mg$^{2+}$ | 3 | 3 |
|   Gd$^{3+}$ | - | 2 |
|   Other ligands/ions | 94 | 90 |
|   Water | 323 | 17 |
| $^{||}$R$_{work}$/R$_{free}$ | 0.190/0.223 | 0.188/0.245 |
| Wilson B-factor (Å$^2$) | 38.5 | 69.2 |
| B-factors (Å$^2$) | | |
|   Protein | 45.8 | 68.2 |
|   TNCA | 34.9 | 61.8 |
|   Mg$^{2+}$ | 53.1 | 74.5 |
|   Gd$^{3+}$ | - | 110.6 |
|   Other ligands/ions | 62.9 | 108.3 |
|   Water | 46.1 | 51.6 |
| R.m.s. deviations | | |
|   Bond lengths (Å) | 0.010 | 0.012 |
|   Bond angles (°) | 1.39 | 1.52 |
| Ramachandran plot (%) | | |
|   Favored | 97.0 | 95.0 |

FIG. 8

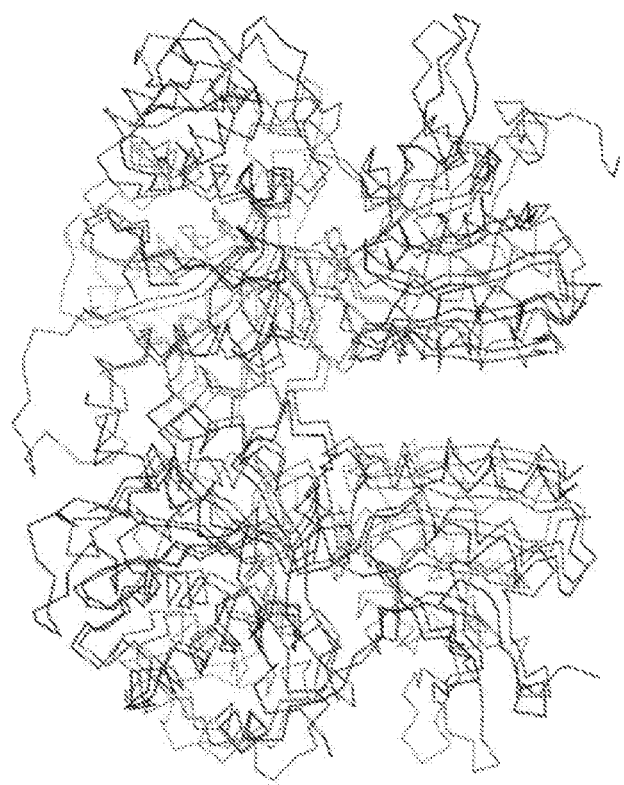
FIG. 9

| Co-activator (mM) | Population Assay | | Single Cell Imaging | |
|---|---|---|---|---|
| | EC$_{50}$ | Hill number | EC$_{50}$ | Hill number |
| 0.0 Ca$^{2+}$ | ND | ND | 12.9 ± 0.3 | 2.9 ± 0.2 |
| 0.5 Ca$^{2+}$ | 7.2 ± 0.4 | 5.5 ± 0.5 | 7.5 ± 0.3 | 4.7 ± 0.8 |
| 1.5 Ca$^{2+}$ | 4.5 ± 0.3 | 2.9 ± 0.6 | 5.9 ± 0.4 | 4.1 ± 0.8 |
| 0.5 Ca$^{2+}$ + 0.5 TNCA | 3.3 ± 0.7 | 3.5 ± 1.0 | ND | ND |
| 0.0 Ca$^{2+}$ + 0.25 TNCA | ND | ND | 5.6 ± 0.3 | 5.2 ± 1.3 |
| 0.5 Ca$^{2+}$ + 0.25 TNCA | ND | ND | 4.8 ± 0.2 | 4.7 ± 0.6 |
| 1.5 Ca$^{2+}$ + 0.25 TNCA | ND | ND | 4.4 ± 0.1 | 3.5 ± 0.2 |
| 0.5 Ca$^{2+}$ + 10.0 Phe | 6.0 ± 0.7 | 4.9 ± 2.3 | ND | ND |

ND: not determined

| Co-activator (0.5 mM Ca$^{2+}$) | 0 mM TNCA | | 0.5 mM TNCA | |
| --- | --- | --- | --- | --- |
| | EC$_{50}$ | Hill number | EC$_{50}$ | Hill number |
| WT | 7.2 ± 0.4 | 4.0 ± 1.0 | 3.3 ± 0.7 | 3.5 ± 1.0 |
| E228I | 10.8 ± 0.3 | 3.9 ± 0.4 | 4.9 ± 0.3 | 6.2 ± 2.6 |
| E228/229I | 10.0 ± 0.5 | 4.6 ± 0.5 | 3.5 ± 0.5 | 4.3 ± 1.7 |
| E297I | No Response | | No Response | |

FIG. 16

| Co-activator (0.0 mM Ca$^{2+}$) | 0 mM TNCA | | 0.25 mM TNCA | |
| --- | --- | --- | --- | --- |
| | EC$_{50}$ | Hill number | EC$_{50}$ | Hill number |
| WT | 12.9 ± 0.3 | 2.9 ± 0.2 | 5.6 ± 0.3 | 5.2 ± 1.3 |
| E228I | 15.6 ± 0.9 | 3.5 ± 0.6 | 6.3 ± 0.2 | 4.6 ± 0.6 |
| E297I | No Response | | No Response | |

FIG. 17

| CaSRL | Residue/Atom | Distance (Å) |
|---|---|---|
| O | S147/N | 3.50 |
|  | S147/OG | 2.64 |
|  | S170/N | 2.87 |
|  | S170/OG | 3.33 |
| OXT | S147/N | 2.89 |
| N | A168/O | 2.65 |
|  | S170/OG | 2.82 |
| NE | E297/OE1 | 2.87 |
|  | E297/OE2 | 3.26 |
| CA | Y218/CD1 | 3.48 |
| C | Y218/CD1 | 3.33 |
| CG | A298/CB | 3.54 |
| CE2 | A298/CA | 3.65 |
| CH2 | W70/CH2 | 3.40 |
| CZ2 | I416/CG1 | 4.19 |

SEQ ID NO: 1
YGPDQRAQKKGDILGGLFPIHFGVAAKDQDLKSRPESVECIRYNFRGFRW
LQAMIFAIEEINSSPALLPNLTLGYRIFDTCNTVSKALEATLSFVAQNKIDSLNLDEFCNCSEHIPSTIA
VVGATGSSGVSTAVANLLGLFYIPQVSYASSSRLLSNKNQFKSFLRTIPNDEHQATAMADIIEYFRWNWVG
TIAADDDYGRPGIEKFREEAEERDICIDFSELISQYSDEEIQHVVEVIQNSTAKVIVVFSSGPDLEPLI
KEIVRRNITGKIWLASEAWASSSLIAMPQYFHVVGGTIGFALKAGQIPGFREFLKNVHPRKSVHNGFAKE
FWEETFNCHLQEGANGPLEVDTFLRGHEESGDRFSNSSTAERPLCTGDENISSVETPYIDYTHLRISYNV
YLAVYSIAHALQDIYTCLPGRGLFTWNGSCADIKKVEAWQVLKHLRHLNFTNNMGEQVTFDECGDLVGNYS
IINWHLSPEDGSIVFKEVGYYNVYAKKGERLFINEEKILWSGFSREVPFSNCSRDCLAGTRKGIIEGEPT
CCFECVECPDGEYSDETDASACNKCPDDFWSNENHTSCIAKEIEFLSWTEPF

FIG. 34A

SEQ ID NO: 2
YGPDQRAQKKGDILGGLFPIHFGVAAKDQDLKSRPESVECIRYNFRGFRW
LQAMIFAIEEINSSPALLPNLTLGYRIFDTCNTVSKALEATLSFVAQNKIDSLNLDEFCNCSEHIPSTIA
VVGATGSSGVSTAVANLLGLFYIPQVSYASSSRLLSMKNQFKSFLRTIPNDEHQATAMADIIEYFRWNWVG
TIAADDDYGRPGIEKFREEAEERDICIDFSELISQYSDEEIQHVVEVIQNSTAKVIVVFSSGPDLEPLI
KEIVRRNITGKIWLASEAWASSSLIAMPQYFHVVGGTIGFALKAGQIPGFREFLKNVHPRKSVHNGFAKE
FWEETFNCHLQEGAKGPLPVDTFLRGHEESGDRFSNSSTAERPLCTGDENISSVETPYIDYTHLRISYNV
YLAVYSIAHALQDIYTCLPGRGLFTWNGSCADIKKVEAWQVLKHLRHLNFTNNMGEQVTFDECGDLVGNYS
IINWHLSPEDGSIVFKEVGYYNVYAKKGERLFINEEKILWSGFSREVPFSNCSRDCLAGTRKGIIEGEPT
CCFECVECPDGEYSDETDASACNKCPDDFWSNENHTSCIAKEIEFLSWTEPF

FIG. 34B

```
SEQ 7:  shark      mvfpspfgpccqlvlrwktskenrccslkvsttesaptitetskkagtfvskltlveaeq
SEQ 8:  zebrafish  ------------------------------------------------------------
SEQ 9:  salmon     ------------------------------------------------------------
SEQ 10: chicken    ------------------------------------------------------------
SEQ 11: mouse      ------------------------------------------------------------
SEQ 12: rat        ------------------------------------------------------------
SEQ 13: human      ------------------------------------------------------------
SEQ 14: gibbon     ------------------------------------------------------------
SEQ 15: dog        ------------------------------------------------------------
SEQ 16: Cow        ------------------------------------------------------------
SEQ 17: Alpaca     ------------------------------------------------------------
SEQ 18: pig        ------------------------------------------------------------ shark      sdllkalgeedetmgghhyglllgftllqsycvseygpnqraqktgdillgglfpihfg
zebrafish  -----------mrfhlkfylhylv---llg-sscvistygpnqraqktgdillgglfpmhfg
salmon     ------------mrfylyylv---llg-fssvistygpdqraqktgdillgglfpmhfg
chicken    -------------mtlysccli---ll-lftwntaaygpnqraqkkgdillgglfpihfg
mouse      -------------mawfgycla---ll-altwhssaygpdqraqkkgdillgglfpihfg
rat        -------------masysccla---ll-alawhssaygpdqraqkkgdillgglfpihfg
human      -------------mafysccwv---ll-altwhtsaygpdqraqkkgdillgglfpihfg
gibbon     -------------mafysccwv---ll-altwhtsaygpdqraqkkgdillgglfpihfg
dog        -------------mafhsc-sl---lllaitwctsaygpdqraqkkgdillgglfpihfg
Cow        -------------malysccwi---llafstwctsaygpdqraqkkgdillgglfpihfg
Alpaca     -------------masysccwi---llaf-awcasaygpdqraqkkgdillgglfpihfg
pig        -------------mafssccwi---llal-twctsaygpdqraqkkgdillgglfpihfg
                              :    :    ;    ;  *.*.*;******.* shark      vtakdqdlksrpemtkcfrynfrgfrwlqamifaleeinnsmaflpnitlgyrifdtcnt
zebrafish  vaskdqdlaarpestecvrynfrgfrwlqamifaiseinnsstllpnitlgyrifdtcnt
salmon     vtskdqdlaarpestecvrynfrgfrwlqamifaleeinnsstllpnitlgyrifdtcnt
chicken    vaakdqdlksrpesveciryngfrwlqamifaleeinnspallpnmtlgyrifdtcnt
mouse      vsakdqdlksrpesveciryngfrwlqamifaleeinsspallpnmtlgyrifdtcnt
rat        vaakdqdlksrpesveciryngfrwlqamifaleeinsspallpnmtlgyrifdtcnt
human      vaakdqdlksrpesveciryngfrwlqamifaleeinsspallpnltlgyrifdtcnt
gibbon     vaakdqdlksrpesveciryngfrwlqamifaleeinsspallpnltlgyrifdtcnt
dog        vaakdqdlksrpesveciryngfrwlqamifaleeinsspallpnmtlgyrifdtcnt
Cow        vavkdqdlksrpesveciryngfrwlqamifaleeinsspallpnmtlgyrifdtcnt
Alpaca     vaakdqdlksrpesveciryngfrwlqamifaleeinsspallpnmtlgyrifdtcnt
pig        vaakdqnlesrpesveciryngfrwlqamifaleeinsspallpnmtlgyrifdtcnt
           *: ****;* ;***  ;*,*************;*********.*  ;***:*********
```

FIG. 35

```
shark      vskaleatlsfvaqnkidslnldefcncsdhipstiavvgatgsgistavanllglfyip
zebrafish  vskaleaslsfvaqkkidslnldefcnctgnipstiavvgasqsavstavadllglfyip
salmon     vskaleatlsfvaqnkidslnldefcnctdhipstiavvqasgsavstavanllglfyip
chicken    vskaleatlsfvaqnkidslnldefcncshipstiavvgatgsgvstavanllglfyip
mouse      vskaleatlsfvaqnkidslnldefcncsehipstiavvgatgsgvstavanllglfyip
rat        vskaleatlsfvaqnkidslnldefcncsehipstiavvgatgsgvstavanllglfyip
human      vskaleatlsfvaqnkidslnldefcncsehipstiavvgatgsgvstavanllglfyip
gibbon     vskaleatlsfvaqnkidslnldefcncsehipstiavvgatgsgvstavanllglfyip
dog        vskaleatlsfvaqnkidslnldefcncsehipstiavvgatgsgistavanllglfyip
Cow        vskaleatlsfvaqnkidslnldefcncsehipstiavvgatgsgistavanllglfyip
Alpaca     vskaleatlsfvaqnkidslnldefcncsehipstiavvgatgsgistavanllglfyip
pig        vskaleatlsfvaqnkidslnldefcncsehipstiavvgatgsgistavanllglfyip
           ****:***********:,********:*,:***:****** shark      qvsyasssrllsnknqyksflrtipndeqqatamadllqhfqwnwvgtlaaddydygrpgi
zebrafish  qisyasssrllsnknqyksfmrtiptdeyqaiamaallehfqwnwvialasddeygrpgi
salmon     qisyasssrllsnknqfksfmrtiptdehqatamadlldyfqwnwviavasddeygrpgi
chicken    qvsyasssrllsnknqfksflrtipndehqatamadlleyfrwnwvgtlaadddygrpgi
mouse      qvsyasssrllsnknqfksflrtipndehqatamadlleyfrwnwvgtlaadddygrpgi
rat        qvsyasssrllsnknqyksflrtipndehqatamadlleyfrwnwvgtlaadddygrpgi
human      qvsyasssrllsnknqfksflrtipndehqatamadlleyfrwnwvgtlaadddygrpgi
gibbon     qvsyasssrllsnknqfksflrtipndehqatamadlleyfrwnwvgtlaadddygrpgi
dog        qvsyasssrllsnknqfksflrtipndehqatamadlleyfrwnwvgtlaadddygrpgi
Cow        qvsyasssrllsnknqfksflrtipndehqatamadlleyfrwnwvgtlaadddygrpgi
Alpaca     qvsyasssrllsnknqfksflrtipndehqatamadlleyfrwnwvgtlaadddygrpgi
pig        qvsyasssrllsnknqfksflrtipndehqatamadlleyfrwnwvgtlaadddygrpgi
           *:*************:*:**,  * **:::*:**** ::*::**** shark      ekfreeaeerdlcidfselisqyytqeelqhvaevignstakvivvfssgpdlepliqei
zebrafish  ekfenemfhrdlcidlnvllsqyvdeaeirrladrlqnssakvivvfasgpdieplvkem
salmon     ekfekemeerdlcihlselisqyfeewqigglvdrienssakvivvfasgpdieplikem
chicken    ekfreeaeerdlcidfselisqysdeeiqqvvevignstarvivvfssgpdlepllkei
mouse      ekfreeaeerdlcidfselisqysdeeiqqvvevignstakvivvfssgpdleplikei
rat        ekfreeaeerdlcidfselisqysdeeiqqvvevignstakvivvfssgpdleplikei
human      ekfreeaeerdlcidfselisqysdeeiqhvvevignstakvivvfssgpdleplikei
gibbon     ekfreeaeerdlcidfselisqysdeeiqhvvevignstakvivvfssgpdleplikei
dog        ekfreeaeerdlcidfselisqysdeeiqqvvevignstakvivvfssgpdleplikei
Cow        ekfreeaeerdlcidfselisqysdeekqqvvevignstakvivvfssgpdleplikei
Alpaca     ekfreeaeerdlcidfselisqysdeeeqqvvevignstakvivvfssgpdleplikei
pig        ekfreeaeerdlcidfselisqysdeeiqqvvevignstakvivvfssgpdleplikei
           ***,:* ,*****,:, *****  :  ::: :,:  *:**:******:***(**;::*;
```

FIG. 35, ctd.

```
shark      vrrnitgriwlaseawasssliakpeyfhvvggtigfalraghipqfyeflqrvhpsrss
zebrafish  vrrnitdrvwlaseawassslvakpeyldvmggtigfalraghipqfkdflqqvhpkkss
salmon     vrrnitdriwlaseawattssliakpeyldvvvgtigfalrageipqfkdflqevtpkkss
chicken    vrrnitgkiwlaseawasssliampeffrvigstigfalkagqipqfreflqtvhpkksa
mouse      vrrnitgriwlaseawasssliampeyfhvvggtigfglkagqipgfreflqkvhprksv
rat        vrrnitgriwlaseawasssliampeyfhvvggtigfglkagqipgfreflqkvhprksv
human      vrrnitgkiwlaseawasssliampqyfhvvggtigfalkagqipgfreflkkvhprksv
gibbon     vrrnitgkiwlaseawasssliampqyfhvvggtigfalkagqipgfreflkkvhprksv
dog        vrrnitgriwlaseawasssliampeyfhvvggtigfalkagqipgfreflqkvhprksv
Cow        vrrnitgriwlaseawasssliampeyfhvvggtigfglkagqipgfreflqkvhprksv
Alpaca     vrrnitgriwlaseawasssliampeyfhvvggtigfalkagqipgfreflqkvhprksv
pig        vrrnitgkiwlaseawasssliampeyfhvvggtigfalkagqipgfreflqkvhpsksv
           ****  :****::*:*  *:::  *: .****.*:.  ::,* * :* shark      dngfvkefweetfkcyltaksltqlkqsk-tpghdgstvvgnitssklippctgdenims
zebrafish  hnefvrafwastfncyledsprn----------------adsengstsfrplctqeedias
salmon     hnefvrefweetfncyledsqrl----------------rdsengstsfrplctgeedimg
chicken    nngfakefweetfncylpaesknspasasfhkahseg-lgagngtaafrppctgdenits
mouse      hngfakefweetfnchlqdgakgplpvdtfvrsheeggncllnsstafrplctgdenins
rat        hngfakefweetfnchlqegakgplpvdtfvrsheeggncllnsstafrplctgdenins
human      hngfakefweetfnchlqegakgplpvdtflrgheeagdrfsnsstafrplctgdeniss
gibbon     hngfakefweetfnchlqegakgplpvdtflrgheesggrfsnsstafrplctgdeniss
dog        hngfakefweetfnchlqegakgplsmdtflrgheegggrisnsstafrplctgdeniss
Cow        hngfakefweetfnchlqegakgplpvdtflrgheeggarlsnsptafrplctgeenlss
Alpaca     hngfakefweetfnchlqegakgplpvdnflrgheegggrtsnsstafrplctgdeniss
pig        hngfakefweetfnchlqegakgplttdtflrgheegggrisnsstafrplctgdeniss
           .* *.:********:*:*   ,                   ; : * ***:*:* , shark      vetpyldythmrisynvymavysiahalqdiytctpgkglfengscadikkveawqvlkh
zebrafish  vetpyldythlrisynvyvavyaiaqalqdiltctpgkglfsngscadirkveawqvlkq
salmon     aetpyldythlrisynvyvavhsiaqalqdiltcipgrglfsnnscadikieawqvlkq
chicken    vetpymdfthlrisynvylavysiahalqdiytctpgkglftngscadikkveawqvlkh
mouse      vetpymdyehlrisynvylavysiahalqdiytclpgrglftngscadikkveawqvlkh
rat        vetpymdyehlrisynvylavysiahalqdiytclpgrglftngscadikkveawqvlkh
human      vetpyidythlrisynvylavysiahalqdiytclpgrglftngscadikkveawqvlkh
gibbon     vetpyidythlrisynvylavysiahalqdiytclpgrglftngscadikkveawqvlkh
dog        vetpymdythlrisynvylavysiahalqdiytclpgrglftngscadikkveawqvlkh
Cow        vetpymdythlrisynvylavysiahalqdiytclpgrglftngscadikkveawqvlkh
Alpaca     vetpymdythlrisynvylavysiahalqdiytclpgrglftngscadikkveawqvlkh
pig        vetpymdythlrisynvylavysiahalqdiytclpgrglftngscadikkveawqvlkh
           .****:*: *:*******;**::**:***** ** **:*:* * *****:*:*******:
```

FIG. 35, ctd.

```
shark       lkhlkftnsmgeqvdfddqgdlkgnytiinwqissedgsvvfgevgnynayakpgerlyi
zebrafish   lrhlnfidsmgervrfdngselsanytiinwhrspedgsvvfkevgyysihnknvaklsi
salmon      lrhlnfsnsmgekvhfdenadpsgnytiinwhrspedgsvvfeevgfynmarakrgvqlfi
chicken     lrhlnftsnmgeqvdfdefgdlvgnysiinwhlspedgsvvfeevghynvyakkgerlfi
mouse       lrhlnftnmgeqvtfdecgdlvgnysiinwhlspedgsivfkevgyynvyakkgerlfi
rat         lrhlnftnmgeqvtfdecgdlvgnysiinwhlspedgsivfkevgyynvyakkgerlfi
human       lrhlnftnmgeqvtfdecgdlvgnysiinwhlspedgsivfkevgyynvyakkgerlfi
gibbon      lrhlnftnmgeqvtfdecgdlvgnysiinwhlsaedgsivfkevgyynvyakkgerlfi
dog         lrhlnftnmgeqvtfdecgdlmgnysiinwhlspedgsivfkevgyynvyakkgerlfi
cow         lrhlnftsnmgeqvtfdecgdlagnysiinwhlspedgsivfkevgyynvyakkgerlfi
Alpaca      lrhlnftnmgeqvtfdecgdlagnysiinwhlspedgsivfkevgyynvyakkgerlfi
pig         lrhlnftsnmgeqvtfdeygdlagnysiinwhlspedgsivfkevgyynvyakkgerlfi
            *;**;*  ..****;* **;  ;*  .;**; * ** *;;* *;      ;* * shark       nsskvlsgfskv-----------vpfsncthdcipgtrkgiiegeptccfecvscaegey
zebrafish   dkskilwngrlte----------vpfsncsvecepgtrkgiildgeptccfectecsdgey
salmon      dntkilwngynte----------vpfsncsedcepgtrkgiiesmptccfectecseqey
chicken     nenkilwsgfske----------vpfsncsrdclpgtrkgiiegeptccfecvdcpdgey
mouse       negkilwsgfsre----------vpfsncsrdcqagtrkgiiegeptccfecaecpdgey
rat         neekilwsgfsre----------vpfsncsrdcqagtrkgiiegeptccfecvecpdgey
human       neekilwsgfsre----------vpfsncsrdclagtrkgiiegeptccfecvecpdgey
gibbon      neekilwsgfsrepltfvlsvpqvpfsncsrdclagtrkgiiegeptccfecvecpdgey
dog         neekilwsgfsre----------mpfsncsrdclagtrkgiiegeptccfecvecpdgey
cow         ndekilwsgfsre----------vpfsncsrdclagtrkgiiegeptccfecvecpdgey
Alpaca      neekilwsgfsre----------vpfsncsrdclagtrkgiiegeptccfecvecpdgey
pig         neekilwsgfsrepltvvlpilqvpfsncsrdclagtrkgiiegeptccfecvecpdgey
            ;.  *;**.*                ;*****;;*  *****;. *****,, * ;*** shark           sdendasactkcpndfwsnenhtyciekeieylswtepf
zebrafish       sdhkdasfcvkcpnnswsngnhtscflkqieflswtepf
salmon          sdhkdasvctkcpndswsnenhtscflkeieflswtepf
chicken         sdetdasacdkcpedywsnenhtscipkqieflswtepf
mouse           sgetdasacdkcpddfwsnenhtsciakeieflawtepf
rat             sgetdasacdkcpddfwsnenhtsciakeieflawtepf
human           sdetdasacnkcpddfwsnenhtsciakeieflswtepf
gibbon          sdetdasacnkcpddfwsnenhtsciakeieflswtepf
dog             sdetdasacdkcpddfwsnenhtsciakeieflswtepf
cow             sdetdasacdkcpddfwsnenhtsciakeieflswtepf
Alpaca          sdetdasacdkcpddfwsnenhtsciakeieflswtepf
pig             sdetdasacdkcpddfwsnenhtsciakeieflswtepf
                * ,.*** * ***;; *** *** *; *;*;*;;*****
```

FIG. 35, ctd.

US 10,639,299 B2

CALCIUM SENSING RECEPTORS, LIGANDS, COMPOSITIONS, AND METHODS OF USE

CROSS-REFERENCE TO RELATED APPLICATIONS

This application claims the benefit of and priority to U.S. Provisional Patent Application No. 62/314,707, filed on Mar. 29, 2016, entitled "CALCIUM SENSING RECEPTORS, LIGANDS, COMPOSITIONS, AND METHODS OF USE," the contents of which is incorporated by reference herein in its entirety.

STATEMENT REGARDING FEDERALLY SPONSORED RESEARCH OR DEVELOPMENT

This invention was made with Government support under contract GM103390 awarded by the National Institutes of Health. The Government has certain rights in the invention.

SEQUENCE LISTING

This application contains a sequence listing filed in electronic form as an ASCII.txt file entitled 220702-2270_ST25.K created on Mar. 27, 2017. The content of the sequence listing is incorporated herein in its entirety.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 2B shows a SDS-PAGE of purified protein sample in reducing (lane 1) and non-reducing (lane 2) conditions, respectively. hCaSR-ECD forms a homodimer as determined by the elution volume observed in size exclusion chromatography and non-reducing SDS-PAGE. The intermolecular disulfide bonds can contribute to dimerization.

FIG. 3A can demonstrate CaSR-mediated $[Ca^{2+}]_i$ responses measured by imaging of single cell calcium oscillation with Fura-2 using HEK293 cells transfected with CaSR in the presence of various concentrations of $[Ca^{2+}]_o$ and $[Mg^{2+}]_o$ and fit to the Hill equation. FIG. 3B can demonstrate that ERK1/2 activities upon stimulation by agonists were detected using western blot and further quantified using ImageJ. The measurements were plotted against different concentrations of $[Ca^{2+}]_o$ or $[Mg^{2+}]_o$ and fit to the Hill equation. FIG. 3C can demonstrate identified metal binding sites in the structure of hCaSR-ECD homodimer. $Mg^{2+}$ and $Gd^{3+}$ are depicted as a hot pink and dark blue spheres, respectively. An anomalous difference map of $Gd^{3+}$ ($\sigma=8.0$) is shown in purple. W represents water molecules. Both site 1 (FIG. 3E) and site 3 (FIG. 3D) are on the "acidic patch" at the dimerization interface of subdomain 2 (FIG. 14), whereas $Mg^{2+}$ at site 2 in subdomain 1 (FIG. 3F) is primarily coordinated by the backbone carbonyl oxygen atoms. (3G) Single mutations of E228I on the "acidic patch" significantly reduce CaSR-mediated $[Ca^{2+}]_i$ responses in the cell population assay.

FIGS. 4B-4E show images that can demonstrate membrane expression of CaSR and its variants. Immunostaining of non-permeabilized HEK293 cells expressing hCaSR was carried out using an anti-FLAG monoclonal antibody, which recognizes the FLAG tag inserted in the CaSR ECD, and detection was carried out with Alexa Fluor 488-conjugated, goat anti-mouse secondary antibody. Blue: DAPI staining cell nuclei. Green: hCaSR immunoreactivity.

FIG. 5A shows a $F_o$-$F_c$ omit map of (CaSR ligand, which is also referred to herein as TNCA) at $\sigma=4.5$. The protein is shown in ribbon mode and the ligand shown in stick mode. The residues around TNCA are labeled in the zoomed-in figure. FIG. 5B shows the results from LC-ESI-MS of a protein sample (top), buffer (middle), and the standard compound (bottom) in negative-ion mode. The high resolution isotopic MS spectra of the indicated peaks are shown in the inserted figures. FIG. 5C shows a representative oscillation pattern from a single HEK293 cell stimulated with various concentrations of extracellular $Ca^{2+}$ or $Mg^{2+}$ in the absence and (FIG. 5D) presence of 0.25 mM TNCATNCA. FIG. 5E can demonstrate the frequency distribution of the $[Ca^{2+}]_i$ oscillation frequency (peak/min) in HEK-293 cells transfected with WT CaSR stimulated with metals in the presence (Red bar) and absence (Black bar) of TNCA. The frequency was recorded at the point when more than 50% single cells started to oscillate. Around 40 cells were analyzed and further plotted as a bar chart. FIGS. 5F-5G can demonstrate that TNCA potentiates $[Mg^{2+}]_o$ or $[Ca^{2+}]_o$ evoked $[Ca^{2+}]_i$ response in a population assay in 5001 cells measured by Fura-2 AM in the absence (black square) or presence of Phe (blue triangular) or TNCA (red closed circle). FIG. 5H can demonstrate that maximally active concentration of 0.1-0.5 mM TNCA dramatically reduces the $EC_{50}$ for activation of $[Ca^{2+}]_i$ signaling by $[Mg^{2+}]_o$ in the presence of 0.5 mM $[Ca^{2+}]_o$. Inset: The $EC_{50}$ changes of $[Mg^{2+}]_o$ are shown over a narrow concentration range of TNCA.

FIG. 6 shows a table demonstrating $EC_{50}$ of $[Mg^{2+}]_o$ for elicitation of $[Ca^{2+}]_i$ rise in cell population assay when different concentrations of TNCA co-applied.

(FIG. 7B) Homodimer of hCaSR-ECD. FIG. 7C shows a structural overlap of hCaSR-ECD with rat mGluR1 in the closed conformation (PDB code: 1 EWK).

FIG. 8 shows a table demonstrating crystallographic statistics of hCaSR-ECD and hCaSR-ECD/Gd$^{3+}$. $^{\ddagger}R_{pim}=\Sigma_{hkl}[1/(N-1)]^{1/2}\Sigma_j|I_j(hkl)-<I(hkl)>|\Sigma_{hkl}\Sigma_j I_j(hkl)$, where N is the redundancy of the dataset. $^{\S}CC_{1/2}$ is the correlation coefficient of the half datasets. $||R_{work}=\Sigma_{hkl}||F_{obs}|-|F_{calc}||/\Sigma_{hkl}|F_{obs}|$, where $F_{obs}$ and $F_{calc}$ is the observed and the calculated structure factor, respectively, $R_{free}$ is the cross-validation R factor for the test set of reflections (10% of the total) omitted in model refinement FIG. 9 shows a comparison of CaSR and mGluR2 structures. Structural overlapping of hCaSR-ECD dimer (blue) with mGluR2 dimer ECD (pink) with bound agonist (PDB code: 4XAQ) with a Ca r.m.s.d. of 2.8 Å. The proteins are depicted in ribbon mode, and TNCA (cyan) and the mGluR agonist (yellow) are in stick mode.

FIG. 10C can demonstrate that ERK1/2 activities upon stimulation by series concentrations of [Mg$^{2+}$]$_o$ in the absence or presence of TNCA in CaSR stably expressed HEK293 cells (5001 cells) were plotted against [Mg$^{2+}$]$_o$ and fit with the Hill equation.

FIG. 13A can demonstrate a magnesium titration curve of hCaSR-ECD (squares). Insert, Trp fluorescence spectra of hCaSR ECD in the presence of 0 (---) or 24 mM Mg$^{2+}$ (-). FIG. 13B Tb$^{3+}$-hCaSR-ECD fluorescence intensity in the presence of 0 (white bar) or 91 mM Mg$^{2+}$ (gray bar).

FIG. 15A can demonstrate that TNCA can potentiate [Mg$^{2+}$]$_o$-evoked [Ca$^{2+}$]$_i$ responses in CaSR mutant E228I and the double mutant E228I/E229I analyzed using fluorimetry in cell population assay in 0.5 mM basal [Ca$^{2+}$]$_o$. FIG. 15B shows a graph that can demonstrate that calcium or TNCA can potentiate the [Mg$^{2+}$]$_o$-stimulated intracellular calcium responses in the single cell imaging assay. Where black squares are without [Ca$^{2+}$]$_o$ or TNCA, green triangles are with 0.25 mM TNCA, red circles are with 0.5 mM [Ca$^{2+}$]$_o$ and 0.25 mM TNCA, and blue diamonds are with 1.5 mM [Ca$^{2+}$]$_o$ and 0.25 mM TNCA. Single cell intracellular calcium responses were recorded using a fluorescence microscope and the normalized [Ca$^{2+}$]$_i$ was plotted against [Mg$^{2+}$]$_o$ then further fitted using the Hill equation. FIG. 15C can show a graph that can demonstrate that TNCA can potentiate [Ca$^{2+}$]$_i$ responses of both WT CaSR or mutant E228I to [Mg$^{2+}$]$_o$ stimulation in single cell imaging assay in the absence of basal [Ca$^{2+}$]$_o$. Black squares are the WT without TNCA, black triangles are the WT with 0.25 mM TNCA, red circles are the E228I mutant without TNCA, red diamonds are the E228I mutant with 0.25 mM TNCA. FIGS. 15D-15G show images that can demonstrate membrane expression of CaSR, mutant E228I and double mutant E228I/E229I. Blue: DAPI staining cell nuclei. Green: hCaSR immunoreactivity.

FIG. 16 shows a table that can demonstrate EC$_{50}$ of [Mg$^{2+}$]$_o$ for stimulation of [Ca$^{2+}$]$_i$ signaling in cell population assay with or without TNCA.

FIG. 17 shows a table that can demonstrate EC$_{50}$ of [Mg$^{2+}$]$_o$ for stimulation of [Ca$^{2+}$]$_i$ signaling in single cell assay with or without TNCA.

FIG. 18A demonstrates results from LC-ESI-MS in positive-ion mode. Only the zoomed-in regions are shown. The species eluted at 4.57 min with a M.W. of 215.08 in positive mode is an unidentified compound in the protein sample. A corresponding ion with m/z 213.06 ion is not detected in negative-ion mode. FIG. 18B demonstrates the results of fragmentation of TNCA in positive-ion mode by application of increased collision energy in protein sample (upper two panels) and in standard sample (synthetic compound, lower two panels).

FIG. 24A can demonstrate the involvement of loop 1 (yellow) and loop 2 (gold) in dimerization. FIG. 24B demonstrates a model for how activation can occur via a conformational change induced by the ligand binding at the hinge region between subdomains 1 and 2 as well as bridging interactions provided by metal ions binding at the "acidic patch" at the interface between the two subdomain 2 regions of the respective protomers. Mutations at these key determinants in the ECD of CaSR cause human disorders with abnormal $[Ca^{2+}]_o$ and $[Mg^{2+}]_o$ homeostasis (FIG. 24C).

FIG. 30D can demonstrate Binding of GTH monitored by ANS florescence (FIG. 30D insert).

FIGS. 34A-34B show ECDs of CASR without (FIG. 34A) or with (FIG. 34B) a FLAG-tag. FIG. 34A shows a human wild-type ECD of CaSR with subdomain 1 underlined, subdomain 2 bolded, and subdomain 3 double underlined. Where there is overlapping of the subdomain(s), all identification features are used. For example, where subdomain 1 overlaps subdomain 2, the relevant amino acids are both bolded and underlined. FIG. 34B shows an ECD of CaSR containing a FLAG-tag (DYKDDDDKD) sequence. The FLAG-tag sequence is underlined where the amino-acids are exogenous to the wild-type human ECD. Thus, The N-Terminal "D" of the FLAG-tag is not underlined in FIG. 34B as it is endogenous to the human wild-type ECD polypeptide and was used to generate the FLAG-tag sequence within the recombinant protein.

FIG. 35 shows a sequence alignment of the ECD of CaSR of human and various other species. Amino acids 1-19 of SEQ ID 13 correspond to a leader sequence that is cleaved during protein production in the cell and not present in the mature ECD.

DETAILED DESCRIPTION

Figure 1:
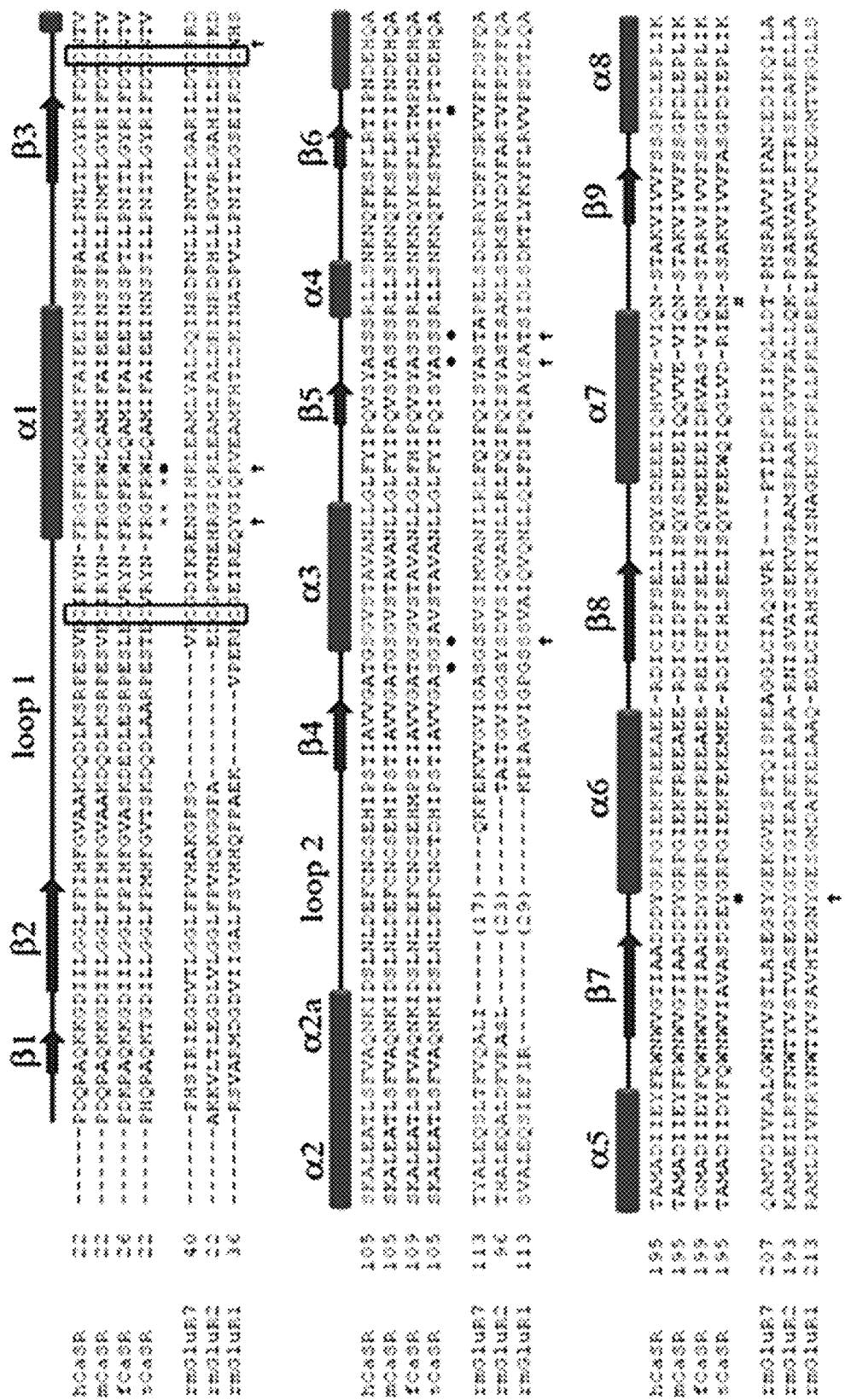
FIG. 1 shows a structure-based sequence alignment of CaSRs and mGluRs (by PROMALS3D). α-helices and β-strands are depicted as cylinders and arrows, respectively. The invariant Cys residues are highlighted in black boxes. The following symbols indicate the residues involved in ligand/ion binding: ● TNCA (also referred to as "CaSRL" or "CaSR ligand"); † Glutamate; × Bicarbonate; # the site of glycosylation. hCaSR: *Homo sapiens* (AAI12237); mCaSR: *Mus musculus* (AAD28371); fCaSR: *Xenopus* (Silurana) *tropicalis* (XP_004919842); sCaSR: *Salmo salar* (NP_001119703); rmGIR7 (PDB code: 2E4Z); rmGluR2 (PDB code: 4XAQ); rmGluR1 (PDB code: 1EWK).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed. As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, and the like, which are within the skill of the art. Such techniques are explained fully in the literature.

Definitions

As used herein, "about," "approximately," and the like, when used in connection with a numerical variable, generally refers to the value of the variable and to all values of the variable that are within the experimental error (e.g., within the 95% confidence interval for the mean) or within +/−10% of the indicated value, whichever is greater.

As used herein, "active agent" or "active ingredient" refers to a component or components of a composition to which the whole or part of the effect of the composition is attributed.

As used herein, "additive effect" refers to an effect arising between two or more molecules, compounds, substances, factors, or compositions that is equal to or the same as the sum of their individual effects.

As used herein, "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

The term "amphiphilic", as used herein, refers to a molecule combining hydrophilic and lipophilic (hydrophobic) properties.

As used herein, "antibody" can refer to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region and a light chain constant region. The VH and VL regions retain the binding specificity to the antigen and can be further subdivided into regions of hypervariability, termed complementarity determining regions (CDR). The CDRs are interspersed with regions that are more conserved, termed framework regions (FR). Each VH and VL is composed of three CDRs and four framework regions, arranged from amino-terminus to carboxy-terminus in the following order: FR1, CDR1, FR2, CDR2, FR3, CDR3, and FR4. The variable regions of the heavy and light chains contain a binding domain that interacts with an antigen.

As used herein, "anti-infectives" can include, but are not limited to, antibiotics, antibacterials, antifungals, antivirals, and anti-protozoals.

The term "biocompatible", as used herein, refers to a material that along with any metabolites or degradation products thereof that are generally non-toxic to the recipient and do not cause any significant adverse effects to the recipient. Generally speaking, biocompatible materials are materials which do not elicit a significant inflammatory or immune response when administered to a patient.

As used herein "biodegradable" generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

As used herein, "composition" or "formulation" can refer to a combination of active agent and at least one other compound or molecule, inert (for example, a detectable agent or label) or active, such as an adjuvant.

As used herein, "concentrated" refers to a molecule, including but not limited to a polynucleotide, peptide, polypeptide, protein, antibody, or fragments thereof, that is distinguishable from its naturally occurring counterpart in that the concentration or number of molecules per volume is greater than that of its naturally occurring counterpart.

As used herein, "control" is an alternative subject or sample used in an experiment for comparison purpose and included to minimize or distinguish the effect of variables other than an independent variable.

As used herein, "diluted" refers to a molecule, including but not limited to a polynucleotide, peptide, polypeptide, protein, antibody, or fragments thereof, that is distinguishable from its naturally occurring counterpart in that the concentration or number of molecules per volume is less than that of its naturally occurring counterpart.

As used herein, "dose," "unit dose," or "dosage" refers to physically discrete units suitable for use in a subject, each unit containing a predetermined quantity of the nanoparticle composition or formulation calculated to produce the desired response or responses in association with its administration.

As used herein, "effective amount" or "amount effective to" can be an amount sufficient to effect beneficial or desired biological, emotional, medical, or clinical response of a cell, tissue, system, animal, or human. An effective amount can be administered in one or more administrations, applications, or dosages. The term also includes within its scope amounts effective to enhance normal physiological function. The effective amount can be an amount of a compound provided herein that can bind to, specifically bind to, activate, stimulate, inhibit activity of, CaSR, an ECD of a CaSR, or inhibit other molecules from binding, activating or otherwise interacting with CaSR. The effective amount can be an amount of a compound provided herein that can treat and/or prevent a disease, disorder, or symptom thereof that is associated with or caused by a mutation of CaSR as provided herein.

The term "hydrophilic", as used herein, can refer to substances that have strongly polar groups that readily interact with water.

The term "hydrophobic", as used herein, can refer to substances that lack an affinity for water; tending to repel and not absorb water as well as not dissolve in or mix with water.

As used herein, "identity," is a relationship between two or more polypeptide or nucleic acid sequence sequences, as determined by comparing the sequences. In the art, "identity" also refers to the degree of sequence relatedness between polypeptide or nucleic acid sequences as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Methods to determine identity are designed to give the largest match between the sequences tested. Methods to determine identity are codified in publicly available computer programs. The percent identity between two sequences can be determined by using analysis software generally known and available in the art (e.g., Sequence Analysis Software Package of the Genetics Computer Group, Madison Ws.) that incorporates the Needleman and Wunsch, (J. Mol. Biol., 1970, 48: 443-453,) algorithm (e.g., NBLAST, and XBLAST). The default parameters are used to determine the identity for the polypeptides of the present disclosure, unless otherwise stated.

As used herein, "isolated" means separated from constituents, cellular and otherwise, in which the polynucleotide, peptide, polypeptide, protein, antibody, or fragments thereof, are normally associated with in nature. A non-naturally occurring polynucleotide, peptide, polypeptide, protein, antibody, or fragments thereof, do not require "isolation" to distinguish it from its naturally occurring counterpart. "Isolated" can refer to a fragment or portion of a protein that is used without the rest of the protein or protein subunits that it is associates with in nature.

As "lipophilic", as used herein, refers to compounds having an affinity for lipids.

As used herein "immunomodulator," refers to an agent, such as a therapeutic agent, which is capable of modulating or regulating one or more immune function or response.

As used herein, "mammal," for the purposes of treatments, refers to any animal classified as a mammal, including human, domestic and farm animals, nonhuman primates, and zoo, sports, or pet animals, such as, but not limited to, dogs, horses, cats, and cows.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "negative control" refers to a "control" that is designed to produce no effect or result, provided that all reagents are functioning properly and that the experiment is properly conducted. Other terms that are interchangeable with "negative control" include "sham," "placebo," and "mock."

As used herein, "pharmaceutical formulation" can refer to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" can refer to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used herein, "positive control" refers to a "control" that is designed to produce the desired result, provided that all reagents are functioning properly and that the experiment is properly conducted.

As used herein, "protein" as used herein can refer to a large molecule composed of one or more chains of amino acids in a specific order. The term protein is used interchangeable with "polypeptide." The order is determined by the base sequence of nucleotides in the gene coding for the protein. Proteins are required for the structure, function, and regulation of the body's cells, tissues, and organs. Each protein has a unique function.

As used herein, the term "recombinant" generally refers to a non-naturally occurring nucleic acid, nucleic acid construct, or polypeptide. Such non-naturally occurring nucleic acids may include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a fusion protein (e.g., a protein or polypeptide formed from the combination of two different proteins or protein fragments), the combination of a nucleic acid encoding a polypeptide to a promoter sequence, where the coding sequence and promoter sequence are from different sources or otherwise do not typically occur together naturally (e.g., a nucleic acid and a constitutive promoter), etc.). Recombinant also refers to the polypeptide encoded by the recombinant nucleic acid. Non-naturally occurring nucleic acids or polypeptides include nucleic acids and polypeptides modified by man.

As used herein, "separated" refers to the state of being physically divided from the original source or population such that the separated compound, agent, particle, or molecule can no longer be considered part of the original source or population.

As used herein, "specifically binds" or "specific binding" refers to binding that occurs between such paired species such as enzyme/substrate, receptor/agonist or antagonist, antibody/antigen, lectin/carbohydrate, oligo DNA primers/DNA, enzyme or protein/DNA, and/or RNA molecule to other nucleic acid (DNA or RNA) or amino acid, which may be mediated by covalent or non-covalent interactions or a combination of covalent and non-covalent interactions. When the interaction of the two species produces a non-covalently bound complex, the binding that occurs is typically electrostatic, hydrogen-bonding, or the result of lipophilic interactions. Accordingly, "specific binding" occurs between a paired species where there is interaction between the two which produces a bound complex having the characteristics of an antibody/antigen, enzyme/substrate, DNA/DNA, DNA/RNA, DNA/protein, RNA/protein, RNA/amino acid, receptor/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

The terms "sufficient" and "effective", as used interchangeably herein, refer to an amount (e.g. mass, volume, dosage, concentration, and/or time period) needed to achieve one or more desired result(s). For example, a therapeutically effective amount refers to an amount needed to achieve one or more therapeutic effects.

As used herein, "synergistic effect," "synergism," or "synergy" refers to an effect arising between two or more molecules, compounds, substances, factors, or compositions that is greater than or different from the sum of their individual effects.

As used interchangeably herein, "subject," "individual," or "patient" refers to a vertebrate organism.

As used herein, "therapeutic" generally can refer to treating, healing, and/or ameliorating a disease, disorder, condition, or side effect, or to decreasing in the rate of advancement of a disease, disorder, condition, or side effect. The term also includes within its scope enhancing normal physiological function, palliative treatment, and partial remediation of a disease, disorder, condition, side effect, or symptom thereof.

The terms "treating" and "treatment" as used herein refer generally to obtaining a desired pharmacological and/or physiological effect. The effect may be prophylactic in terms of preventing or partially preventing a disease, symptom or condition thereof, such as disease or disorders resulting from a mutation in the N-terminal extracellular binding domain of a calcium signaling receptor or abnormal (e.g. great or less) activity (as compared to a suitable control) of a CaSR.

As used herein, "wild-type" is the typical or average of an organism, variety, strain, gene, protein, or characteristic as it occurs in any given or defined population (natural or otherwise designated), as distinguished from mutant forms that may result from selective breeding, spontaneous, or transformation with a transgene.

Unless otherwise defined herein, all technical and scientific terms used herein have the same meaning as commonly understood by one of ordinary skill in the art.

Discussion

The discovery of the parathyroid $Ca^{2+}$-sensing receptor (CaSR) established a new paradigm that extracellular $Ca^{2+}$ ($[Ca^{2+}]_o$) can act as a first messenger for regulation of diverse cellular processes, in addition to its well-known roles as a second messenger. Extracellular divalent cations, particularly $[Ca^{2+}]_o$ and magnesium $[Mg^{2+}]_o$, along with amino acids and neurotransmitters, regulate numerous cellular processes via CaSR and 14 other family C, G protein-coupled receptors (cGPCRs), including metabotropic glutamate (mGluRs) and γ aminobutyric acid (GABA)B receptors. Small changes in $[Ca^{2+}]_o$ or $[Mg^{2+}]_o$ trigger CaSR-mediated intracellular $Ca^{2+}$ signaling and activate ERK1/2[8]. CaSRs play a central role in regulating $[Ca^{2+}]_o$ and $[Mg^{2+}]_o$ homeostasis by activating intracellular $Ca^{2+}$ signaling, in turn, inhibiting PTH release, stimulating calcitonin secretion and promoting renal $Ca^{2+}$ excretion. L-amino acids, especially those with aromatic side chains, potentiate high $[Ca^{2+}]_o$-elicited activation of CaSR via positive heterotropic functional cooperativity[5]. Like other cGP-CRs, CaSR functions as a dimer with a long (about 600 amino acids) N-terminal ECD playing an important role in the receptor's cooperative responses to its agonists. Over 400 mutations in CaSR cause human disorders with abnormal $[Ca^{2+}]_o$ and $[Mg^{2+}]_o$ homeostasis, including familial hypocalciuric hypercalcemia (FHH), neonatal severe hyperparathyroidism (NSHPT) and autosomal dominant hypocalcemia (ADH); 225 of the mutations map to the ECD, highlighting its critical role. To clarify the mechanism for cooperative activation of CaSR by $[Ca^{2+}]_o$, $[Mg^{2+}]_o$, and amino acids, this Example demonstrates, inter alia, the solution of the first crystal structure of human CaSR-ECD bound with $Mg^{2+}$ ions and a high-affinity tryptophan derivative. As such, there exists a need for improved therapeutics that for diseases affected by mutations in the ECD and improved tools for screening potential drugs that can modulate the CaSR.

With that said, described herein are methods of modulating ECD and/or CaSR activity by administering an amount of L-1,2,3,4-tetrahydronorharman-3-carboxylic acid (TNCA) to a subject in need thereof, methods for screening for ligands, inhibitors, and or activators of a CaSR and/or ECD, antibodies that can bind a CaSR ECD and/or subdomain, and isolated and/or recombinant ECD polypeptides. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

ECD Polypeptides

Described herein are ECD polypeptides corresponding to the N-terminal ECD of a normal or diseased (such as a mutated) CaSR. The ECD polypeptides can be generated using recombinant technology such that they do not include the other portions of a CaSR protein. In embodiments, the ECD can have an amino acid sequence selected from SEQ ID NOs.: 1-18. In embodiments, the ECD can have an amino acid sequence that is about 50%-100%, about 50%-60%, about 60%-70%, about 70%-80%, about 80%-90%, about 90-95%, about 95%-99%, or about 99% to about 100% identical with any one of SEQ ID NOs.: 1-18. In embodiments, the ECD is a polypeptide that is the functional equivalent to any one of SEQ ID NOs.: 1-18. In some embodiments, the ECD polypeptide only contains an amino acid sequence that is about 90% to 100% identical to any one of SEQ ID NOs.: 1-18.

The ECD can be a recombinant polypeptide having a sequence that is about 50% to 100% identical to an amino acid sequence selected from the group of: SEQ ID NOS.: 1-18. The ECD can be a recombinant polypeptide consisting of a sequence that is about 50% to 100% identical to an amino acid sequence selected from the group of: SEQ ID NOS.: 1-18. The ECD can be an isolated polypeptide comprising a sequence that is about 50% to 100% identical to an amino acid sequence selected from the group of: SEQ ID NOS.: 1-18. The ECD can be an isolated polypeptide consisting of a sequence that is about 50% to 100% identical to an amino acid sequence selected from the group consisting of: SEQ ID NOS.: 1-18. In embodiments, the ECD at least contains a binding pocket with a 3D coordination as described in relation to FIGS. 33A-33B. In some embodiments, the binding pocket includes the following residues (specified in relation to SEQ ID NO.: 13: S147, A168, S170, and Y218 W70, A298, I416 and E297. In embodiments, the binding pocket can include the functionally homologues residues to S147, A168, S170, and Y218 W70, A298, I416 and E297 (specified in relation to SEQ ID NO.: 13).

The ECD can be a mutant polypeptide having an N-terminal ECD of a CaSR, wherein the ECD contains at least one mutation as compared to a wild-type N-terminal extracellular domain of the CaSR. The wild-type ECD can be a sequence that is 100% identical to an amino acid sequence selected from the group consisting of: SEQ ID NOS.: 1-18. The ECD can be a mutant polypeptide, where the mutation (relative to SEQ ID NO.: 13) can be selected from the group of: R25X, T138M, N118K, E127K/G/A, C129Y/F/S/R, L125P/F, P55L, C60F, R185Q, Q245R, R220W/P/Q, E250K, R227L, P221L/S, W208S, R172R/K, E297K/D, T151M/R/K, Q164X, F351V, wherein the mutations are described in relation to SEQ ID NO.: 13. In embodiments, the mutation corresponds to and/or results in FHH, ADH, neonatal severe hyperparathyroidism (NSHPT) or some cases of primary hyperparathyroidism (PHPT).

Serum concentrations of ionized calcium and magnesium are clinically important because low or high levels can directly cause symptoms or even disorders. Hypocalcemia, hypercalcemia and hypomagnesemia are clinically important disorders. Hypermagnesemia is usually observed in the context of acute or chronic kidney disease (CKD). The most important complications of hypercalcemia, hypocalcemia, and hypomagnesemia are electrocardiogram (ECG) changes and arrhythmias, neuropsychiatric symptoms, neuromuscular symptoms and polyuria (hypercalcemia). Hypomagnesemia is often asymptomatic but can cause complications because of secondary hypocalcemia and hypokalemia and is also associated with kaliuresis. Chronic hypercalcemia may predispose to vascular calcifications and nephrocalcinosis, while chronic hypocalcemia may cause rickets. Magnesium deficiency has been linked to diabetes mellitus and hypertension (Hoorn and Zietse, Pediatr Nephrol (2013) 28:1195-1206 DOI 10.1007/s00467-012-2350-2). Additionally, several cancers such as breast cancer, prostate cancer and colon cancer have altered expression of CaSR and mutations as reported in COSMIC and TGCA data bank. These disorders may be treatable with drugs or antibodies that increase or decrease the activity of the CaSR, such as those described herein.

Antibodies Capable of Binding the ECD

Also described herein are antibodies capable of specifically binding an N-terminal ECD of a CaSR. The antibody can be a polyclonal or monoclonal antibody or a fragment there of. Methods of making polyclonal and monoclonal antibodies are generally known in the art. The antibody can be humanized. The antibody can be capable of specifically binding an ECD having a polypeptide sequence that is about 90% to 100% identical to any one of SEQ ID NOs. 1-18 or a fragment thereof of at least 5 contiguous amino acids. The antibody can be capable of specifically binding a subdomain of an ECD described herein. In embodiments the subdomain has a sequence that is about 90% to 100% identical to any one of SEQ ID NOs. 3, 4, or 5 or a fragment thereof of at least 5 contiguous amino acids.

TNCA and Pharmaceutical Formulations Thereof

As described elsewhere herein, TNCA is a compound capable of binding the ECD of CaSR. In some embodiments, the TNCA can be labeled with a suitable label. Suitable labels include, but are not limited to, a radioisotopes, a NMR label, and fluorescent labels, which are commercially available. Suitable radioisotopes can include, but are not limited to $^{13}C$, $^{18}F$, $^{2}H$, $^{15}N$, $^{15}O$, $^{11}C$, and $^{123}I$. Suitable fluorescent labels include, but are not limited to fluorescein and its derivatives, rhodamine and its derivatives, Atto labels, CF™ dyes, fluorescent red and orange labels, and others that will instantly be appreciated by those of skill in the art. NMR labels, are labels (radioisotope or otherwise) that can produce a distinguishable NMR signal. The TNCA can be labeled at any suitable position and by techniques that will be known to one of ordinary skill in the art. Such labeled TNCA compounds are considered to be included when TNCA is generally referenced herein.

Also provided herein are pharmaceutical formulations that can include an amount of TNCA described herein and a pharmaceutical carrier appropriate for administration to an individual in need thereof. The individual in need thereof can have or can be suspected of having a disease or condition associated with a CaSR and/or an ECD of a CaSR. The disease or condition can be the result of a mutation in the CaSR and/or ECD of a CaSR. The disease can be a disease or condition that is the result of a mutation in the ECD or result from dysfunction of the CaSR of another cause. In embodiments, the disease or condition can be familial hypocalciuric hypercalcemia (FHH), autosomal dominant hypocalcemia (ADH), neonatal severe hyperparathyroidism (NSHPT), primary hyperparathyroidism (PHPT), severe secondary hyperparathyroidism in patients receiving dialysis treatment for kidney failure, tertiary hyperparathyroidism, persistent or recurrent hyperparathyroidism, hyperparathyroidism occurring after renal transplantation, lithium-induced hyperparathyroidism, hypoparathyroidism, kidney stones, hypomagnesemia, hypermagnesemia, the condition of calciphylaxis (severe calcification of the skin that can be fatal), osteoporosis, and dysfunction of the CaSR arising from activating or inactivating autoantibodies. The mutation of the ECD can be at least one of the amino acid mutations can be selected from the group of: R25X, T138M, N118K, E127K/G/A, C129Y/F/S/R, L125P/F, P55L, C60F, R185Q, Q245R, R220W/P/Q, E250K, R227L, P221L/S, W208S, R172R/K, E297K/D, T151M/R/K, Q164X, F351V, wherein the mutations are described in relation to SEQ ID NO.: 13.

The pharmaceutical formulations described herein can include an amount of TNCA that can be an amount effective to treat and/or prevent disease, condition, or symptom thereof of a mutation or otherwise dysfunction of a CaSR protein in the subject in need thereof. Such diseases and conditions can include, but are not limited to, familial hypocalciuric hypercalcemia (FHH), autosomal dominant hypocalcemia (ADH), neonatal severe hyperparathyroidism (NSHPT), primary hyperparathyroidism (PHPT), severe secondary hyperparathyroidism in patients receiving dialysis treatment for kidney failure, tertiary hyperparathyroidism, persistent or recurrent hyperparathyroidism, hyperparathyroidism occurring after renal transplantation, lithium-induced hyperparathyroidism, hypoparathyroidism, kidney stones, hypomagnesemia, hypermagnesemia, the condition of calciphylaxis (severe calcification of the skin that can be fatal), osteoporosis, and dysfunction of the CaSR arising from activating or inactivating autoantibodies.

TNCA can be included in the manufacture of a medicament for treating or preventing a disease or condition associated with a CaSR and/or an ECD of a CaSR. The disease or condition can be the result of a mutation in the CaSR and/or ECD of a CaSR. The disease can be a disease or condition that is the result of a mutation in the ECD or result from dysfunction of the CaSR of another cause. In embodiments, the disease or condition can be familial hypocalciuric hypercalcemia (FHH), autosomal dominant hypocalcemia (ADH), neonatal severe hyperparathyroidism (NSHPT), primary hyperparathyroidism (PHPT), severe secondary hyperparathyroidism in patients receiving dialysis treatment for kidney failure, tertiary hyperparathyroidism, persistent or recurrent hyperparathyroidism, hyperparathyroidism occurring after renal transplantation, lithium-induced hyperparathyroidism, hypoparathyroidism, kidney stones, hypomagnesemia, hypermagnesemia, the condition of calciphylaxis (severe calcification of the skin that can be fatal), osteoporosis, and dysfunction of the CaSR arising from activating or inactivating autoantibodies.

The formulations provided herein can be administered via any suitable administration route. For example, the formulations (and/or compositions) can be administered to the subject in need thereof orally, intravenously, intramuscularly, intravaginally, intraperitoneally, rectally, parenterally, topically, intranasally, or subcutaneously. Other suitable routes are described herein.

Parenteral Formulations

The TNCA can be formulated for parenteral delivery, such as injection or infusion, in the form of a solution or suspension. Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the TNCA as described herein can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants can be anionic, cationic, amphoteric or nonionic surface active agents. Suitable anionic surfactants include, but are not limited to, those containing carboxylate, sulfonate and sulfate ions. Suitable anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Suitable cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Suitable nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine, and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation can also contain an antioxidant to prevent degradation of the TNCA.

The formulation can be buffered to a pH of 3-8 for parenteral administration upon reconstitution. Suitable buffers include, but are not limited to, phosphate buffers, acetate buffers, and citrate buffers.

Water-soluble polymers can be used in the formulations for parenteral administration. Suitable water-soluble polymers include, but are not limited to, polyvinylpyrrolidone, dextran, carboxymethylcellulose, and polyethylene glycol. Sterile injectable solutions can be prepared by incorporating TNCA in the needed amount in the appropriate solvent or dispersion medium with one or more of the excipients listed above, as required, followed by filtered sterilization. Dispersions can be prepared by incorporating the sterilized TNCA into a sterile vehicle which contains the basic dispersion medium and the required other ingredients from those listed above. Sterile powders for the preparation of sterile injectable solutions can be prepared by vacuum-drying and freeze-drying techniques, which yields a powder of the TNCA plus any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for parenteral administration can be in the form of a sterile aqueous solution or suspension of particles formed from TNCA. Acceptable solvents include, for example, water, Ringer's solution, phosphate buffered saline (PBS), and isotonic sodium chloride solution. The formulation can also be a sterile solution, suspension, or emulsion in a nontoxic, parenterally acceptable diluent or solvent such as 1,3-butanediol.

In some instances, the formulation can be distributed or packaged in a liquid form. In other embodiments, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration can be buffered with an effective amount of buffer necessary to maintain a pH suitable for ocular administration. Suitable buffers include, but are not limited to, acetate, borate, carbonate, citrate, and phosphate buffers.

Solutions, suspensions, or emulsions for parenteral administration can also contain one or more tonicity agents to adjust the isotonic range of the formulation. Suitable tonicity agents include, but are not limited to, glycerin, mannitol, sorbitol, sodium chloride, and other electrolytes.

Solutions, suspensions, or emulsions for parenteral administration can also contain one or more preservatives to prevent bacterial contamination of the ophthalmic preparations. Suitable preservatives include, but are not limited to, polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions, use of nanotechnology including nanoformulations for parenteral administration can also contain one or more excipients, such as dispersing agents, wetting agents, and suspending agents.

Topical Formulations

TNCA can be formulated for topical administration. Suitable dosage forms for topical administration include creams, ointments, salves, sprays, gels, lotions, emulsions, liquids, and transdermal patches. The formulation can be formulated for transmucosal, transepithelial, transendothelial, or transdermal administration. The topical formulations can contain one or more chemical penetration enhancers, membrane permeability agents, membrane transport agents, emollients, surfactants, stabilizers, and combination thereof.

In some embodiments, the TNCA can be administered as a liquid formulation, such as a solution or suspension, a semi-solid formulation, such as a lotion or ointment, or a solid formulation. In some embodiments, the TNCA can be formulated as liquids, including solutions and suspensions, such as eye drops or as a semi-solid formulation, such as ointment or lotion for topical application to the skin, to the mucosa, such as the eye, to the vagina, or to the rectum.

The formulation can contain one or more excipients, such as emollients, surfactants, emulsifiers, penetration enhancers, and the like.

Suitable emollients include, without limitation, almond oil, castor oil, *ceratonia* extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In some embodiments, the emollients can be ethylhexylstearate and ethylhexyl palmitate.

Suitable surfactants include, but are not limited to, emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In some embodiments, the surfactant can be stearyl alcohol.

Suitable emulsifiers include, but are not limited to, acacia, metallic soaps, certain animal and vegetable oils, and various polar compounds, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In some embodiments, the emulsifier can be glycerol stearate.

Suitable classes of penetration enhancers include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols).

Suitable emulsions include, but are not limited to, oil-in-water and water-in-oil emulsions. Either or both phases of the emulsions can include a surfactant, an emulsifying agent, and/or a liquid non-volatile non-aqueous material. In some embodiments, the surfactant can be a non-ionic surfactant.

In other embodiments, the emulsifying agent is an emulsifying wax. In further embodiments, the liquid non-volatile non-aqueous material is a glycol. In some embodiments, the glycol is propylene glycol. The oil phase can contain other suitable oily pharmaceutically acceptable excipients. Suitable oily pharmaceutically acceptable excipients include, but are not limited to, hydroxylated castor oil or sesame oil can be used in the oil phase as surfactants or emulsifiers.

Lotions containing TNCA are also provided. In some embodiments, the lotion can be in the form of an emulsion having a viscosity of between 100 and 1000 centistokes. The fluidity of lotions can permit rapid and uniform application over a wide surface area. Lotions can be formulated to dry on the skin leaving a thin coat of their medicinal components on the skin's surface.

Creams containing TNCA are also provided. The cream can contain emulsifying agents and/or other stabilizing agents. In some embodiments, the cream is in the form of a cream having a viscosity of greater than 1000 centistokes, typically in the range of 20,000-50,000 centistokes. Creams, as compared to ointments, can be easier to spread and easier to remove.

One difference between a cream and a lotion is the viscosity, which is dependent on the amount/use of various oils and the percentage of water used to prepare the formulations. Creams can be thicker than lotions, can have various uses, and can have more varied oils/butters, depending upon the desired effect upon the skin. In some embodiments of a cream formulation, the water-base percentage can be about 60% to about 75% and the oil-base can be about 20% to about 30% of the total, with the other percentages being the emulsifier agent, preservatives and additives for a total of 100%.

Ointments containing TNCA and a suitable ointment base are also provided. Suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

Also described herein are gels containing TNCA as described herein, a gelling agent, and a liquid vehicle. Suitable gelling agents include, but are not limited to, modified celluloses, such as hydroxypropyl cellulose and hydroxyethyl cellulose; carbopol homopolymers and copolymers; thermoreversible gels and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents can be selected for their ability to dissolve the drug. Other additives, which can improve the skin feel and/or emolliency of the formulation, can also be incorporated. Such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Also described herein are foams that can include TNCA. Foams can be an emulsion in combination with a gaseous propellant. The gaseous propellant can include hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or can become approved for medical use are suitable. The propellants can be devoid of hydrocarbon propellant gases, which can produce flammable or explosive vapors during spraying. Furthermore, the foams can contain no volatile alcohols, which can produce flammable or explosive vapors during use.

Buffers can be used to control pH of a composition. The buffers can buffer the composition from a pH of about 4 to a pH of about 7.5, from a pH of about 4 to a pH of about 7, or from a pH of about 5 to a pH of about 7. In some embodiments, the buffer can be triethanolamine.

Preservatives can be included to prevent the growth of fungi and microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

In certain embodiments, the formulations can be provided via continuous delivery of one or more formulations to a patient in need thereof. For topical applications, repeated application can be done or a patch can be used to provide continuous administration of the noscapine analogs over an extended period of time.

Enteral Formulations

TNCA or pharmaceutical salt thereof as described herein can be prepared in enteral formulations, such as for oral administration. Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations containing TNCA can be prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include, but are not limited to, suitable hydrophobic or hydrophilic polymers and suitable pH dependent or independent polymers. Suitable hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins. "Carrier" also includes all components of the coating composition which can include plasticizers, pigments, colorants, stabilizing agents, and glidants.

Formulations containing TNCA can be prepared using one or more pharmaceutically acceptable excipients, including diluents, preservatives, binders, lubricants, disintegrators, swelling agents, fillers, stabilizers, and combinations thereof.

Delayed release dosage formulations containing TNCA can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

The formulations containing TNCA can be coated with a suitable coating material, for example, to delay release once the particles have passed through the acidic environment of the stomach. Suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings can be formed with a different ratio of water soluble polymer, water insoluble polymers and/or pH dependent polymers, with or without water insoluble/water soluble non polymeric excipient, to produce the desired release profile. The coating can be performed on a dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Additionally, the coating material can contain conventional carriers such as plasticizers, pigments, colorants, glidants, stabilization agents, pore formers and surfactants. Optional pharmaceutically acceptable excipients include, but are not limited to, diluents, binders, lubricants, disintegrants, colorants, stabilizers, and surfactants.

Diluents, also referred to as "fillers," can be used to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful.

Binders can impart cohesive qualities to a solid dosage formulation, and thus can ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders.

Lubricants can be included to facilitate tablet manufacture. Suitable lubricants include, but are not limited to, magnesium stearate, calcium stearate, stearic acid, glycerol behenate, polyethylene glycol, talc, and mineral oil. A lubricant can be included in a tablet formulation to prevent the tablet and punches from sticking in the die. The lubricant can be chosen from such slippery solids as talc, magnesium and calcium stearate, stearic acid and hydrogenated vegetable oils.

Disintegrants can be used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers can be used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Additional Active Agents

In some embodiments, an amount of one or more additional active agents are included in the pharmaceutical formulation containing TNCA or pharmaceutical salt thereof. Suitable additional active agents include, but are not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics.

Screening Assays

Also provided herein are methods of evaluating compounds on their ability to bind and/or modulate activity of an ECD of a CaSR and thus the activity of the CaSR. In embodiments, the method contains the steps of contacting an ECD, with a compound and measuring activity of the ECD and/or CaSR by a suitable method. Suitable methods of measuring activity of the ECD and/or CaSR include, but are not limited to, intracellular calcium oscillation, cell population assay, IP production, ERK1/2 assay, production of PTH, scillation frequency changes, FACS, and/or oocytes assay. In embodiments, the activity can be measured by quantitatively or qualitatively measuring calcium and/or magnesium binding to the ECD and/or CaSR.

Techniques to measure calcium and/or magnesium binding to the ECD can include, but are not limited to, Tb-FRET, measuring tryptophan florescence changes, measuring ANS florescence changes, nuclear magnetic resonance spectroscopy, measuring thermal stability, Biacore, mass spectrometry, isothermal titration calorimetry, and any combination thereof. The step of contacting the ECD and/or CaSR with the compound(s) can occur in vitro, ex vivo, in situ, or in vivo.

In some aspects, a candidate compound that can interact with the CaSR and/or ECD can be identified in a screening assay in which displacement of and/or competition with TNCA, which can be labeled, for the ECD of CaSR is measured. The ability for the candidate compound to compete for and/or displace TNCA can be directly correlated to the strength of the ability of the compound to bind the ECD of the CaSR. In these embodiments, displacement of the TNCA can be measured by detecting TNCA or its label by a suitable method. Such detection methods and techniques will be appreciated by those of ordinary skill in the art.

The ECD can be any ECD as described elsewhere herein. The CaSR can be a CaSR that contains an ECD as described elsewhere herein. The compound can be any compound including, but not limited to, small molecules, biologics, and other macromolecules. In some embodiments the compound is L-1,2,3,4-tetrahydonorharman-3-carboxylic acid (TNCA). The compound can be a candidate compound. As used herein, a candidate compound is a compound that is tested to determine its ability to bind and/or modulate the activity of an ECD and/or CaSR as described elsewhere herein.

The screening assay can be used to identify agonists, antagonists, inverse agonists, allosteric activators, allosteric antagonists, or allosteric inactivators of an ECD and/or a CaSR. The screening assay can be formatted as desired and can be single run or high-throughput. Techniques, equipment, and design of single-run and high-throughput assays will be appreciated by those of ordinary skill in the art in view of this disclosure.

Methods of Modulating ECD and/or CaSR Activity

Also provided herein are methods of modulating ECD and/or CaSR activity. In embodiments, the method can include the step of contacting a CaSR and/or ECD of a CaSR with an amount of a compound. The compound can be any compound. In some embodiments the compound is L-1,2,3,4-tetrahydonorharman-3-carboxylic acid (TNCA) or a formulation thereof. The compound can be a candidate compound. In embodiments, the amount of the compound is effective to increase or decrease the amount of CaSR and/or ECD activity. The step of contacting the ECD and/or CaSR with the compound(s) can occur in vitro, ex vivo, in situ, or in vivo. The ECD can be any ECD as described elsewhere herein. The CaSR can be a CaSR that contains an ECD as described elsewhere herein.

In some embodiments the method further includes the step of administering the compound to a subject in need thereof. The subject in need thereof can have a mutation in the ECD polypeptide corresponds to familial hypocalciuric hypercalcemia (FHH), autosomal dominant hypocalcemia (ADH), neonatal severe hyperparathyroidism or primary hyperparathyroidism (NSH PT), primary hyperparathyroidism and/or have dysfunction of the ECD due to another cause, such as that due to over- or under expression of CaSR corresponding to conditions that include (PHPT), severe secondary hyperparathyroidism in patients dialyzed for kidney failure, tertiary hyperparathyroidism, persistent or recurrent hyperparathyroidism, hyperparathyroidism occurring after renal transplantation, lithium-induced hyperparathyroidism, hypoparathyroidism, kidney stones, hypomagnesemia, hypermagnesemia, the condition of calciphylaxis (severe calcification of the skin that can be fatal), osteoporosis, and dysfunction of the CaSR arising from activating or inactivating autoantibodies. Modulating the activity of the CaSR might also be the basis for treatment of cancers arising from mutations in and/or abnormalities in the activity of the CaSR. Other diseases include hypocalcemia, hypercalcemia and hypomagnesemia related diseases discussed above (Hoorn and Zietse, Pediatr Nephrol (2013) 28:1195-1206 DOI 10.1007/s00467-012-2350-2) and several cancers such as breast cancer, prostate cancer and colon cancer with altered expression of CaSR and mutations as reported in COSMIC and TGCA data bank. These disorders may be treatable with drugs or antibodies that increase or decrease the activity of the CaSR.

Methods of Treating a Disease or Conditions Associated with CaSRs

Also provided herein are methods that can be used to treat a disease or condition associated with a CaSR and/or an ECD of a CaSR. The disease or condition can be the result of a mutation in the CaSR and/or ECD of a CaSR. In embodiments the method of treating a disease associated with a mutation of the extracellular calcium binding domain (ECD) of a calcium sensing receptor protein (CaSR) and/or a disease where the symptom is abnormal CaSR expression and/or activity, or a symptom thereof in a subject in need thereof can include the step of administering an amount of L-1,2,3,4-tetrahydonorharman-3-carboxylic acid (TNCA), and/or an antibody as described herein to the subject in need thereof. The amount can be an amount effective to modulate the activity of a CaSR. The amount can be an amount effective to increase the activity of CaSR. The amount can be an amount effective to decrease the activity of CaSR. The disease can be a disease or condition that is the result of a mutation in the ECD or result from dysfunction of the CaSR of another cause. In embodiments the disease or condition can be familial hypocalciuric hypercalcemia (FHH), autosomal dominant hypocalcemia (ADH), neonatal severe hyperparathyroidism (NSHPT), primary hyperparathyroidism (PHPT), severe secondary hyperparathyroidism in patients receiving dialysis treatment for kidney failure, tertiary hyperparathyroidism, persistent or recurrent hyperparathyroidism, hyperparathyroidism occurring after renal transplantation, lithium-induced hyperparathyroidism, hypoparathyroidism, kidney stones, hypomagnesemia, hypermagnesemia, the condition of calciphylaxis (severe calcification of the skin that can be fatal), osteoporosis, and dysfunction of the CaSR arising from activating or inactivating autoantibodies. Modulating the activity of the CaSR might also be the basis for treatment of cancers arising from mutations in and/or abnormalities in the activity of the CaSR. The mutation of the ECD is at least one of the amino acid mutations can be selected from the group of: R25X, T138M, N118K, E127K/G/A, C129Y/F/S/R, L125P/F, P55L, C60F, R185Q, Q245R, R220W/P/Q, E250K, R227L, P221L/S, W208S, R172R/K, E297K/D, T151M/R/K, Q164X, F351V, wherein the mutations are described in relation to SEQ ID NO.: 13. The TNCA, and/or antibody as described herein can be contained in a pharmaceutical formulation comprising the amount of TNCA, and/or antibody and a pharmaceutically acceptable carrier.

The amount can be an amount effective to modulate the activity of a CaSR. The amount can be an amount effective increase or decrease the activity of CaSR. The amount can be an amount effective to potentiate $Ca^{2+}$ activation of the CaSR. The amount can be an amount effective to potentiate $Mg^{2+}$ activation of the CaSR. In some embodiments the method can include administering an antibody according as described herein to a subject in need thereof, wherein the subject in need thereof has a disease associated with a mutation of the extracellular calcium binding domain (ECD) of a calcium sensing receptor protein (CaSR) and/or a disease where the symptom is abnormal CaSR expression and/or activity, or a symptom thereof.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

The discovery of the parathyroid $Ca^{2+}$-sensing receptor (CaSR) established a new paradigm that extracellular $Ca^{2+}$ ($[Ca^{2+}]_o$) can act as a first messenger for regulation of diverse cellular processes, including regulating the secretion of parathyroid hormone (PTH), modulating calcium reabsorption by the kidney, etc., in addition to its well-known roles as a second messenger[1,2]. Extracellular divalent cations, particularly $[Ca^{2+}]_o$ and magnesium $[Mg^{2+}]_o$, along with amino acids and neurotransmitters, regulate numerous cellular processes via CaSR and 14 other family C, G protein-coupled receptors (cGPCRs), including metabotropic glutamate (mGluRs) and γ aminobutyric acid (GABA)B receptors[3-7]. Small changes in $[Ca^{2+}]_o$ or $[Mg^{2+}]_o$ trigger CaSR-mediated intracellular $Ca^{2+}$ signaling and activate MAP kinase ERK1/2[8]. CaSRs play a central role in regulating $[Ca^{2+}]_o$ and $[Mg^{2+}]_o$ by stimulating phospholipase C to generate inositol 1,4,5-trisphosphate, which triggers release of calcium from its intracellular calcium stores to increase the intracellular free calcium concentration ($[Ca^{2+}]_i$) and activate $[Ca^{2+}]_i$ signaling[9-11], in turn, inhibits PTH release, stimulates calcitonin secretion and promotes renal $Ca^{2+}$ excretion[12-15]. ERK1/2[8]. CaSRs play a central role in regulating $[Ca^{2+}]_o$ and $[Mg^{2+}]_o$ homeostasis by activating intracellular $Ca^{2+}$ signaling[9], in turn, inhibiting PTH release, stimulating calcitonin secretion and promoting renal $Ca^{2+}$ excretion[10]. L-amino acids, especially those with aromatic side chains, potentiate high $[Ca^{2+}]_o$-elicited activation of CaSR via positive heterotropic functional cooperativity[5]. Like other cGPCRs, CaSR functions as a dimer[11,12] with a long (~600 amino acids) N-terminal ECD playing an important role in the receptor's cooperative responses to its agonists[7]. Over 400 mutations in CaSR cause human disorders with abnormal $[Ca^{2+}]_o$ and $[Mg^{2+}]_o$ homeostasis, including familial hypocalciuric hypercalcemia (FHH), neonatal severe hyperparathyroidism (NSHPT) and autosomal dominant hypocalcemia (ADH); 225 of the mutations map to the ECD, highlighting its critical role[13]. To clarify the mechanism for cooperative activation of CaSR by $[Ca^{2+}]_o$, $[Mg^{2+}]_o$, and amino acids, this Example demonstrates, inter alia, the solution of the first crystal structure of human CaSR-ECD bound with $Mg^{2+}$ ions and a high-affinity tryptophan derivative, which can play a role in potentiating the function of CaSR.

Figure 2A:
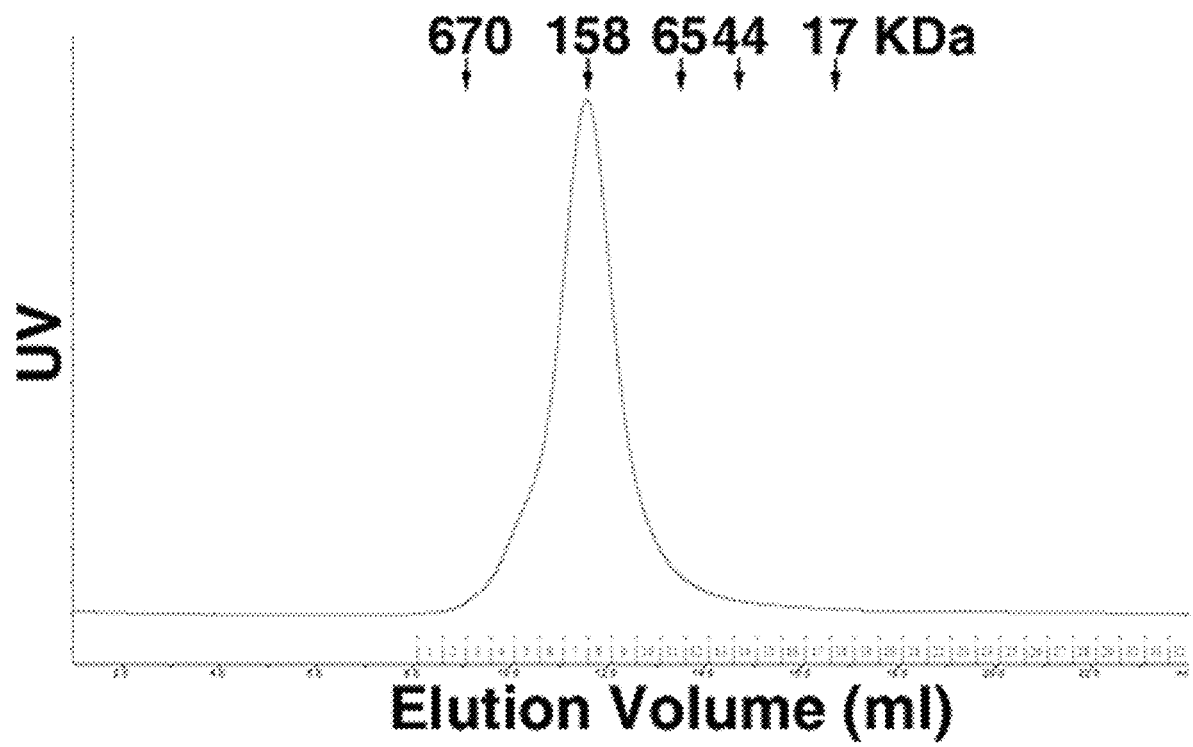
FIGS. 2A-2B shows a graph and representative image of a gel demonstrating size exclusion chromatography of purified hCaSR-ECD. The elution volumes of the standard proteins are indicated by arrows.
Figure 2B:
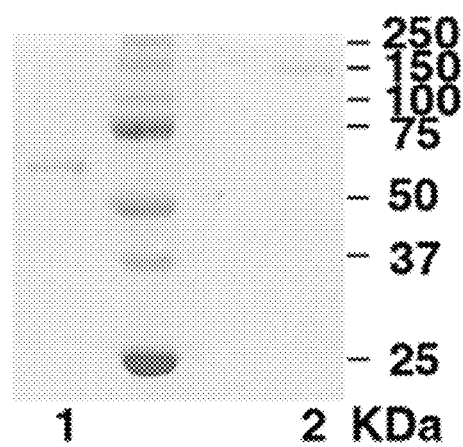

Materials and Methods
Purification of the Extracellular Domain of the Human CaSR (hCaSR-ECD) Secreted from Hek293S Gnti-Cells hCaSR-ECD (from residue $Tyr^{20}$ to $Phe^{612}$) (FIG. 1) was expressed in suspension culture of HEK293S (GnTI-) cells and purified from the culture medium by $Ni^{2+}$-NTA chromatography as previously described. To deglycosylate the purified protein, hCaSR-ECD was incubated with recombinant endoglycosidase F1 (Endo F1) at a 1:100 mass ratio of Endo F1 to hCaSR-ECD[26] overnight at 4° C. in 10 mM Tris buffer, pH 7.4. Further separation of hCaSR-ECD from Endo F1 was achieved by size exclusion chromatography (SEC) in 10 mM HEPES (pH 7.3) buffer. hCaSR-ECD forms a homodimer, as determined by the elution volume observed in SEC. The electrophoretic mobility in reducing/non-reducing SDS-PAGE indicates that intermolecular disulfide bonds contribute to dimerization (FIG. 2).

Crystallization, Data Collection and Structure Determination.

The dimeric hCaSR-ECD was concentrated to 10 mg/mL and crystallized in 10% PEG 8000, 200 mM $MgCl_2$, 10 mM $CaCl_2$ and 100 mM Tris-HCl, pH 7.0, using a sitting drop approach at 21° C. No crystals were formed in the absence of $Ca^{2+}$ or $Mg^{2+}$. The plate-shaped crystals were cryo-protected using 25% glycerol and flash-frozen in liquid nitrogen. Dehydration by soaking the crystal in 12% PEG 8000 overnight improved the resolution from 3.5~4 Å to 2-3 Å. The diffraction data of the crystals were collected on the beamline of 21-ID-D at LS-CAT in APS, and indexed, integrated and scaled in HKL2000[27]. The structure was solved at 2.1 Å by molecular replacement using Auto-MR in PHENIX[28]. The structure of chain A of mGluR2 with a bound agonist (PDB code: 4XAQ) was used as the search template[29]. The electron density map after molecular replacement is clear enough to identify the unique features of hCaSR-ECD, and iterative model building and refinement were performed using COOT[30] and Refmac5 in the CCP4[31] suite, respectively. The restraints of TNCA (also referred to in this Example as "TNCA") were generated by JLigand in COOT.

To generate the $Gd^{3+}$ derivative, the native crystals were soaked with a solution containing 12% PEG 8000, 200 mM $MgCl_2$, 10 mM $CaCl_2$, 100 mM Tris-HCl pH 7.0, and 0.5 mM $GdCl_3$ overnight at 21° C. The anomalous signals of a dataset at 2.7 Å collected at the wavelength of 1.6985 Å were used to locate $Gd^{3+}$ in the structure. The structure was solved by molecular replacement using the previously determined structure as the search template. All the figures of protein structures were generated by PyMOL v1.3 (Schrodinger LLC).

Figures 3A, 3B, 3C, 3D, 3E, 3F, 3G:
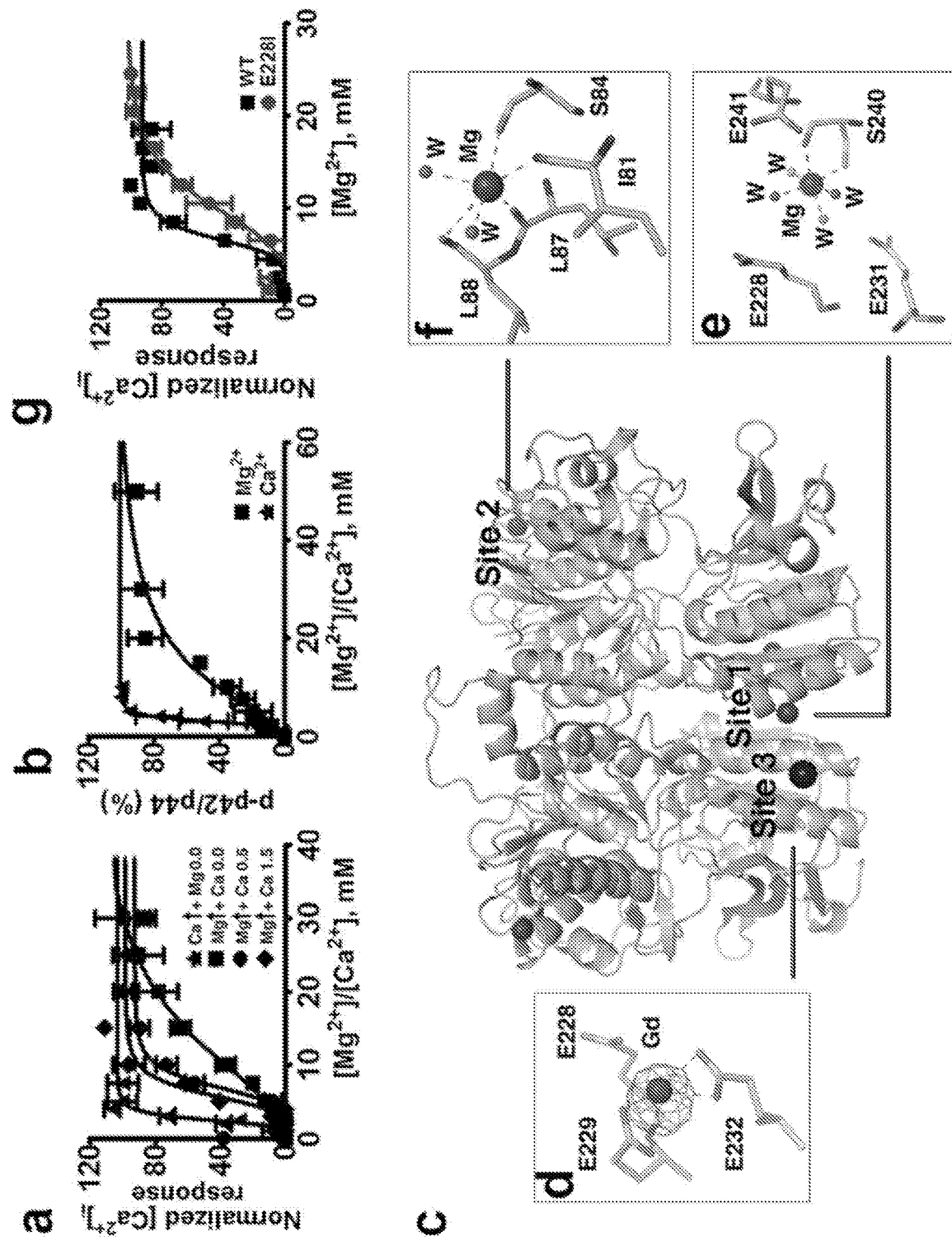
FIGS. 3A-3G can demonstrate a structural basis for $Mg^{2+}/Ca^{2+}$ modulated CaSR activities.
Figure 4A:
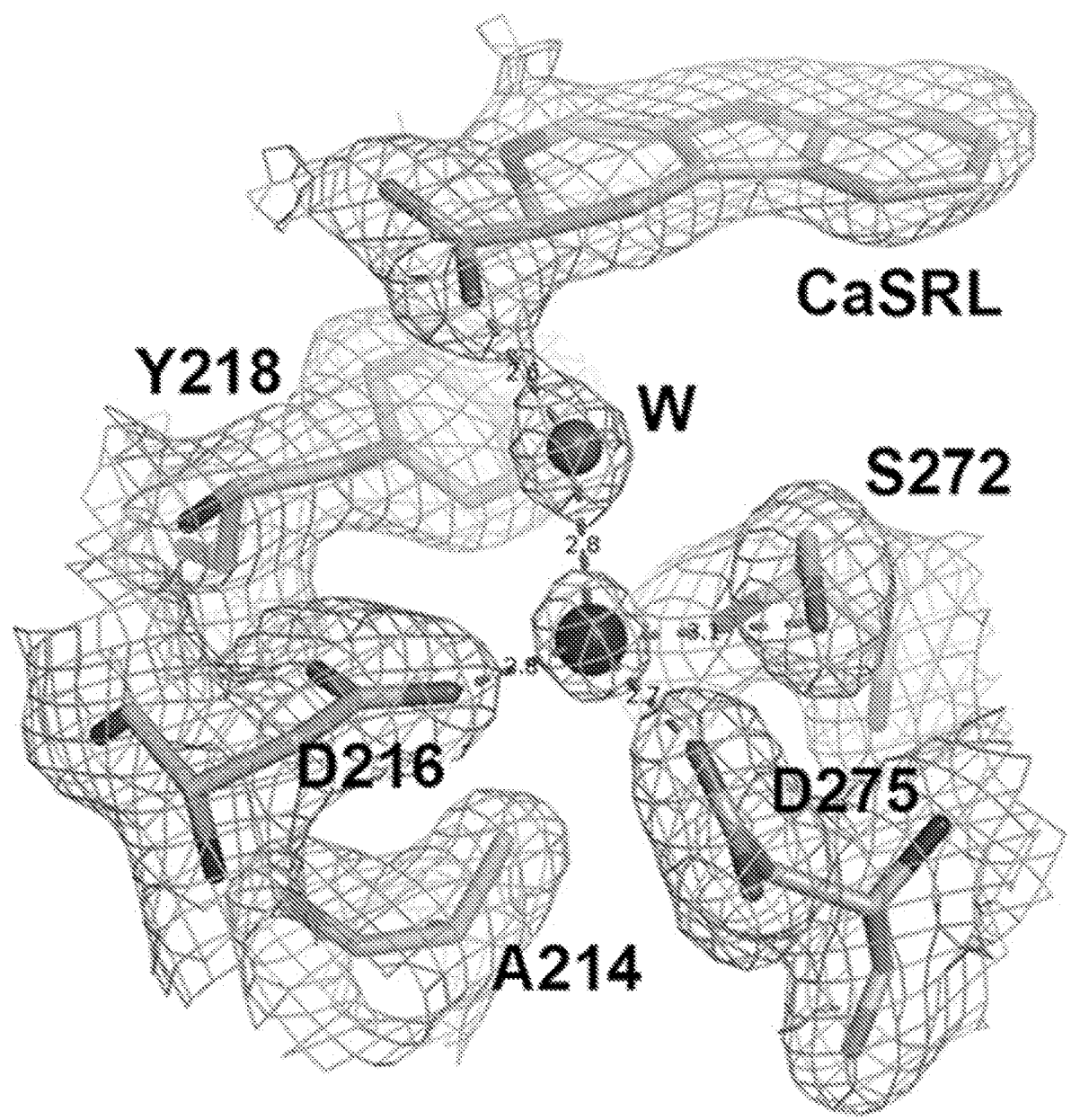
FIGS. 4A-4E demonstrate identification of a potential $Mg^{2+}$ binding site at the hinge region. (4A) Putative $Mg^{2+}$ ion (large hot pink sphere) is coordinated by the side chains of D216, D275, S272 and a water molecule (amino acid positions here and throughout the disclosure are numbered according to SEQ ID NO. 13). The 2Fo-Fc electron density map ($\sigma=1$) is shown in light blue. W indicates the water molecule (small sphere) bridging the putative $Mg^{2+}$ and TNCA (CaSR ligand, CaSRL"). The dashed lines in grey indicates the potential Mg—O interaction. The distances (in Å) between $Mg^{2+}$ and oxygen atoms are shown on the dashed lines.
Figure 4B:
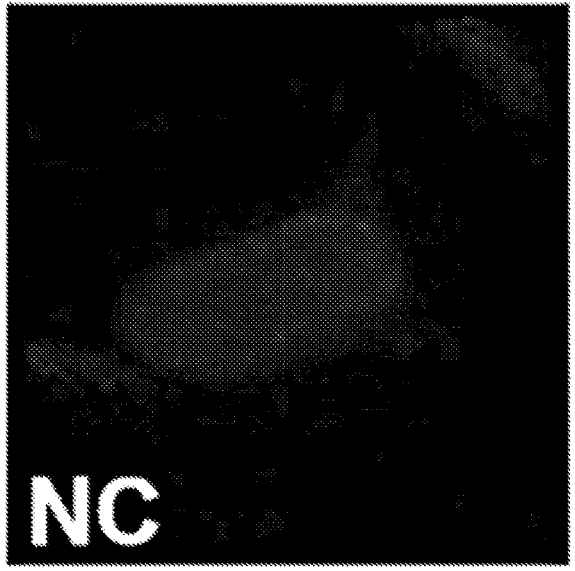
Figure 4C:
Figure 4D:
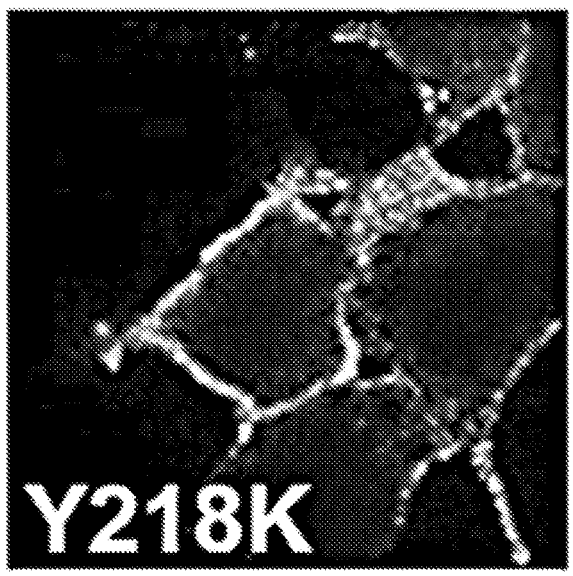
Figure 4E:
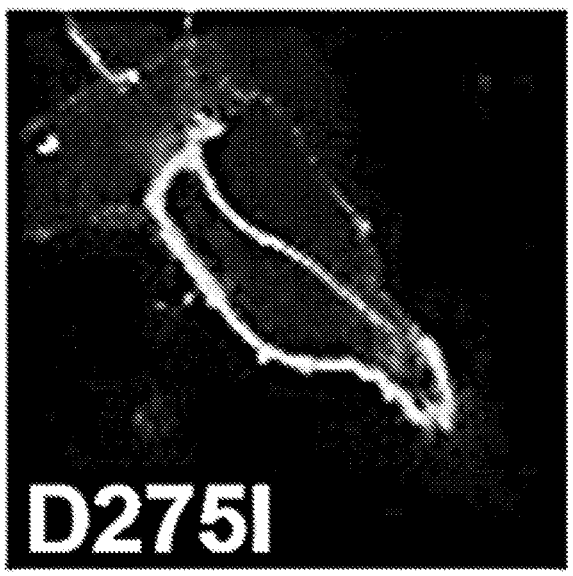

Using local geometric constraints and electron density intensity as major criteria, $Mg^{2+}$ bound at site 1 and site 2 (FIG. 3B) were unambiguously identified. Evidence also suggests a potential $Mg^{2+}$ binding site at the hinge region in the proximity of the bound TNCA (FIGS. 4A-B). Modeling a water molecule at this position led to a B factor (26-32 $Å^2$) substantially smaller than the coordinating atoms (35-40 $Å^2$), suggestive of a slightly heavier atom occupying this position. Considering the negatively charged coordination sphere (A214, D216, Y218, S272, D275 and water), it is possible that this density corresponds to a bound $Mg^{2+}$. Mutations such as Y218K and D2751 results in diminished intracellular calcium responses using both the cell population assay and single cell calcium imaging assays, although these mutations retain their surface expression (FIG. 4B). Alternatively, it may be a highly ordered water molecule trapped at the hinge region, as the distances to the coordinating oxygen atoms (2.5-2.8 Å) are significantly greater than typically observed Mg—O distance in biomolecules (2.1 Å)[32]. Nevertheless, the distorted geometry does not exclude the possibility that it could be a weak $Mg^{2+}$ binding site with a low occupancy. At this stage, we placed a water molecule in the model; however, given the importance of the hinge region in CaSR function and regulation, more functional and structural studies are warranted to further investigate this potential $Mg^{2+}$ binding site identified in this Example.

High Resolution Liquid Chromatography-Electrospray Ionization-Mass Spectrometry (LC-ESI-MS) and Identification of TNCA.

Figure 5A:
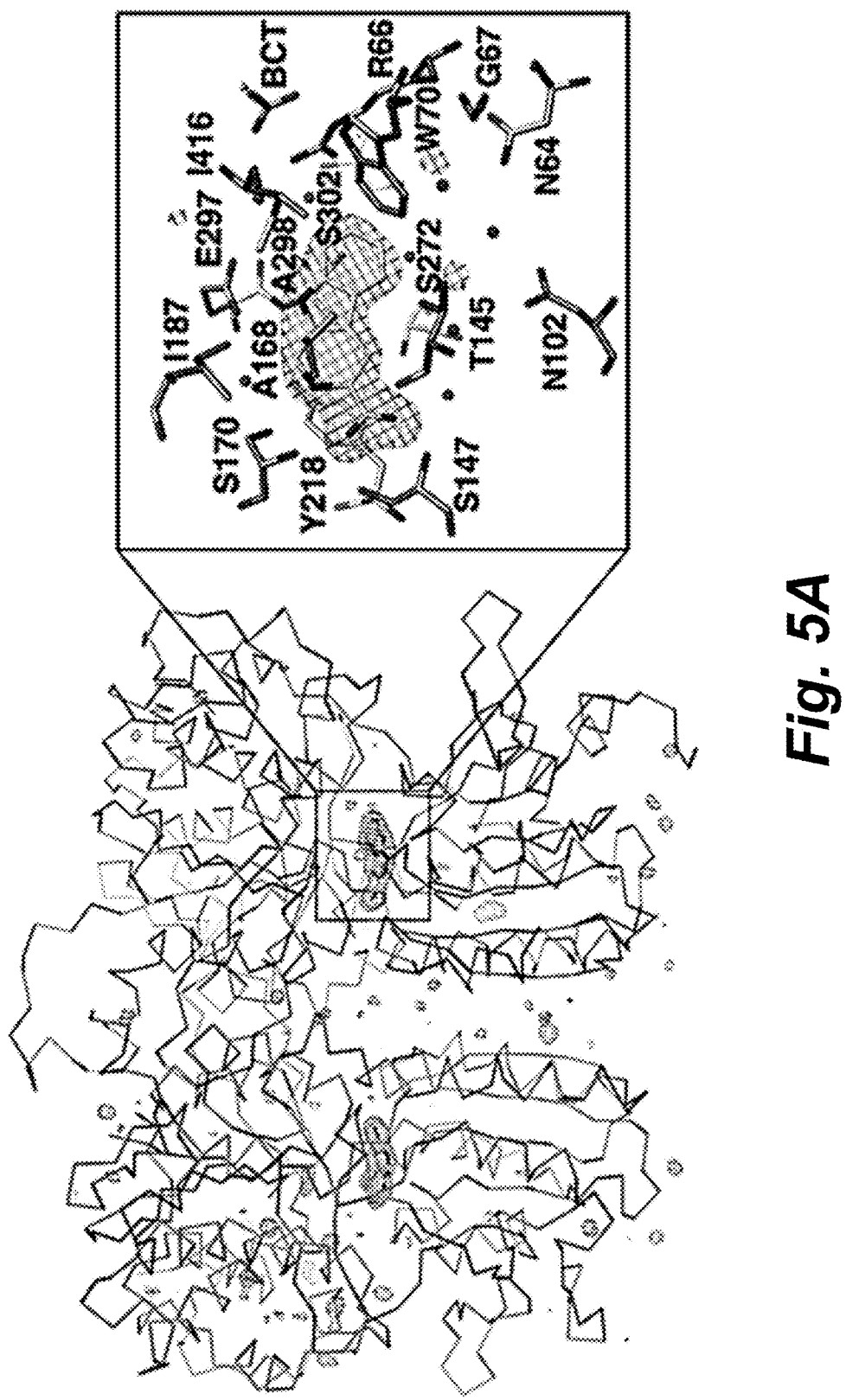
FIGS. 5A-5H can demonstrate the identification and characterization of a tryptophan derivative bound to hCaSR-ECD as a high-affinity co-agonist of CaSR.

As shown in FIG. 5A, there is an unidentified ligand (CaSR ligand) bound at the putative orthosteric ligand binding site of CaSR-ECD. We examined the known CaSR ligands, including phenylalanine, tryptophan, glutathione (GSH), and polyamines, as well as the reagents used in sample preparation and crystallization, but none of them fit the density well. Among these initial trials, tryptophan appeared to be the best fit to the electron density of the unknown ligand, but an additional density was unaccounted for when tryptophan was used fit the electron density. The size of the density suggests that CaSR ligand contains 14-18 heavy atoms (C/N/O/S/P), and the absence of anomalous signal indicates that it does not contain sulfur or phosphate. Accordingly, the $M_r$ of CaSR ligand can be within the range of ~180-250 Da.

Considering CaSR ligand is tightly bound with hCaSR-ECD, it is conceivable that hCaSR-ECD has to be denatured to release CaSR ligand. To extract CaSR ligand, 50 µL of purified hCaSR-ECD (10 mg/mL) was mixed with 120 µL acetonitrile and vortexed. After high speed centrifugation, 10 µL of the CaSR ligand extract was injected onto a reverse-phase ACQUITY UPLC BEH C18 column (2.1 mm×100 mm, 1.7-µm particle size; Waters). Column temperature was maintained at 40° C. The flow rate was 0.3 mL/min with starting conditions at 99% solvent A (water+ 0.1% formic acid) and 1% solvent B (acetonitrile). The 15-min gradient profile for elution was as follows: starting at 1% solvent B and hold for 1 min, then ramping to 98% B at 10 min, hold at 98% B to 12 min, at 12.01 min return to 99% A/1% B and maintain until 15 min. The samples were analyzed by using a Waters Xevo G2-XS QToF LC-MS interfaced to a Waters Acquity UPLC system. The MS settings were as follows: electrospray ionization in negative-ion mode, 2.00 kV capillary voltage, 100° C. source temperature, 350° C. desolvation temperature, 600 liters/h desolvation nitrogen gas flow rate, 35 V cone voltage, and mass range of m/z 50 to 1500 with spectra accumulated at 0.1 seconds/function. Three separate acquisition functions were performed to generate spectra at different collision energies (5, 25, and 60 eV) providing both non-fragmenting and fragmenting conditions. Analyses of samples by electrospray ionization in positive-ion mode were performed under the same conditions as negative-ion mode except the collision energies (5, 20, and 40 eV). Fragmentation, formula, and abundances were analyzed with Waters MassLynx Software.

Using the above approach, we identified a species eluting at ~4.65 min, detected by MS in both positive-ion mode (m/z=217.0990) and negative-ion mode (m/z=215.0824), exclusively present in protein samples from several different batches, but not in sample buffer. The predicted elemental compositions based on mass are $C_{12}H_{13}N_2O_2$ (calculated mass=217.0977) for positive-ion mode and $C_{12}H_{11}N_2O_2$ (calculated mass=215.0824 Da) for negative-ion mode. A thorough search in the PubChem database led to a list of candidates containing of up to 200 compounds with the same $M_r$ and formula. By manually fitting the density map with these compounds, only L-1,2,3,4-tetrahydronorharman-3-carboxylic acid (TNCA) fit the density perfectly. The synthetic TNCA dissolved in the SEC buffer was treated in the same way as the protein samples in the LC-ESI-MS experiment and resulted in a peak detected at the same retention time and having the same mass spectrum. In LC-ESI-MS experiment, we also noticed a minor species eluted at ~4.57 min (FIG. 19), which is detectable only in the positive-ion mode (m/z=215.0836) and having a predicted elemental formula of $C_{12}H_{11}N_2O_2$. The 2 Da smaller $M_r$ for this related compound suggests that it is a derivative of TNCA, likely due to a double bond formation between the backbone N and a neighboring C. As it is also likely to be a tryptophan derivative, we cannot exclude the possibility that it binds hCaSR-ECD with high affinity. This compound may also form during CaSR ligand extraction. Nevertheless, TNCA perfectly fits the electron density at 2.1 Å and any extra double bonds in the TNCA structure would likely be detrimental to fitting the density.

A phenylalanine replacement experiment was carried out by mixing purified hCaSR-ECD protein (0.26 mg/mL) with phenylalanine (final concentrations are 0, 50 and 150 mM, respectively). After overnight incubation at room temperature, hCaSR-ECD in each sample was re-purified with Ni-NTA beads. The protein samples were adjusted to the same concentration using SEC buffer and analyzed by LC-ESI-MS.

Monitoring $Mg^{2+}$-Binding to CaSR-ECD by Fluorescence Spectroscopy.

The imidazole in fractions of hCaSR-ECD eluted from the $Ni^{2+}$-NTA column was removed by passing the protein through desalting columns in HEPES buffer (10 mM HEPES, pH 7.2). The Trp fluorescence spectra of hCaSR-ECD were recorded on a QM1 fluorescence spectrophotometer (PTI) in a 1-cm-pathlength cell with a xenon short-arc lamp at ambient temperature. The emission between 300-400 nm was acquired during excitation at 282 nm. A solution containing 2 µM hCaSR-ECD in 10 mM HEPES (pH 7.2), 120 mM NaCl, and 10 mM KCl was gradually titrated by addition of $Ca^{2+}$ prepared in the same HEPES buffer. The binding constants of $Mg^{2+}$ to CaSR-ECD were calculated by fitting the titration curve with the Hill equation. The $Ca^{2+}$—$Tb^{3+}$ competition experiments were performed in solutions containing 35 µM $Tb^{3+}$ and 2 µM hCaSR-ECD as the starting point. $MgCl_2$ was added to the mixture from a 1 M stock solution while maintaining a constant $Tb^{3+}$ concentration in the solution. The $Mg^{2+}$-binding affinity of the protein was calculated by fitting normalized fluorescence intensity data using the Hill equation: (Eq. 1)

$$\Delta S = \frac{[M]^n}{K_d^n + [M]^n} \quad \text{Eq. 1}$$

where $\Delta S$ is the total signal change in the equation, $K_d$ is the apparent binding affinity, n is the Hill coefficient, and [M] is the free metal concentration.

CaSR ligand and $Mg^{2+}$ binding site mutation design. All of the full length CaSR mutants were generated by site-directed mutagenesis based on the sequence of the human CaSR in the pcDNA3.1(+) expression vector (provided by Dr. Edward Brown). Site-directed mutagenesis was performed using the QuikChange® kit (Stratagene, Cedar Creek, Tex.) according to the manufacturer's instructions. Briefly, a pair of complementary primers of 27-35 bases was designed for generating each mutant with the mutation placed at the middle of the primers. The template human CaSR in pcDNA3.1(+) was amplified using Pfu DNA polymerase (Stratagene) with these primers for 16 cycles in a PCR instrument (TECHNE). After digestion of the template DNA with DpnI (New England Biolabs), the amplified mutant DNA was transformed into XL10-Gold Ultracompetent cells. All the DNA sequences were verified by Genewiz (www.genewiz.com).

Cell Culture and Transfection.

Monolayer cultures of human embryonic kidney cells (HEK293) were purchased from ATCC (ATCC® CRL-1573™) and maintained in DMEM supplemented with 10% FBS and high glucose (4.5 g/L) at 37° C. Wild type CaSR or its mutants were transfected into HEK293 cells using Lipofectamine 2000 (Life Technology) by following the manufacturer's instructions.

Immunostaining.

Cells transfected with hCaSR-pcDNA3.1(+) were used in the immunostaining experiments, and this construct contains a FLAG-tag between $Asp^{371}$ and $Thr^{372}$. After 48 h post transfection, cells were fixed with 3.7% formaldehyde for 15 minutes at room temperature, followed by washing 3 times with PBS. Mouse anti-FLAG monoclonal antibody was diluted 500 times and incubated with cell overnight at 4° C. to stain the cell surface CaSR. The cells were subsequently washed with PBS and stained with goat anti-mouse Alexa488-conjugated secondary antibody for 1 hour at room temperature. Nuclei were stained with DAPI. Fluorescence was visualized using a Zeiss LSM780 confocal microscope.

Measurement of $[Ca^{2+}]_i$ Changes Triggered by $[Mg^{2+}]_o$ in Single CaSR-Transfected Cells.

Measurement of intracellular free $Ca^{2+}$ was assessed as described by Huang, et al[33]. Briefly, wild type CaSR, or its mutants, were transiently transfected into HEK293 cells grown on coverslips and cultured for 48 h. The cells were subsequently loaded for 15 min using 2 µM Fura-2 AM in 2 mL physiological saline buffer (10 mM HEPES, 140 mM NaCl, 5 mM KCl, 1.0 mM $MgCl_2$ and pH 7.4). The coverslips were mounted in a bath chamber on the stage of a Leica DM6000 fluorescence microscope. The cells were alternately illuminated with 340 or 380 nm light, and the fluorescence at an emission wavelength 510 nm was recorded in real time as the $[Ca^{2+}]_o$ and/or $[Mg^{2+}]_o$ was increased in a stepwise manner in the presence or absence of 0.25 mM TNCA in buffer (10 mM HEPES, 155 mM NaCl, 5 mM KCl, 2 mM $NaH_2PO_4$, 0.5 mM $MgCl_2$ and pH 7.4). The ratio of the emitted fluorescence intensities resulting from excitation at both wavelengths was utilized as a surrogate for changes in $[Ca^{2+}]_i$ and was further plotted and analyzed as a function of $[Ca^{2+}]_o$. All experiments were performed at room temperature. The signals from 20 to 100 single cells were recorded for each measurement. Oscillations were identified as three successive fluctuations in $[Ca^{2+}]_i$ after the initial peak.

Determination of the Effect of TNCA on $Mg^{2+}$-Evoked $[Ca^{2+}]_i$ Signaling by Stimulation of CaSR in Cell Populations.

Changes in the intracellular $Ca^{2+}$ concentration $[Ca^{2+}]_i$ elicited by extracellular $Mg^{2+}$ ($[Mg^{2+}]_o$) in a population of cells were measured by fluorimetry as described previously[33]. A cell line stably expressing CaSR (designated the "5001 cell line") was seeded on 13.5×20-mm coverslips and cultured in DMEM. After reaching 95% confluence, cells were washed three times using loading buffer (20 mM HEPES [pH 7.4], 125 mM NaCl, 5 mM KCl, 1.25 mM $CaCl_2$, 1 mM $MgCl_2$, 1 mM $NaH_2PO_4$, 1% glucose, and 1% BSA) and subsequently incubated with 4 µM Fura-2 and 4 µM pluronic F127 for 20 minutes at 37° C. to enable sufficient dye loading in the same buffer. After removing the excess Fura-2, coverslips with cells were diagonally positioned in a quartz cuvette filled with 3 ml of experimental buffer (125 mM NaCl, 5 mM KCl, 0.5 mM $CaCl_2$, 0.5 mM $MgCl_2$, 1% glucose, and 1% BSA). Measurements of Fura-2 fluorescence at 510 nm when excited at 340 or 380 nm were performed on a QM1 fluorescence spectrophotometer (PTI).

The emission ratio of 340/380 was calculated and used to reflect the changes in $[Ca^{2+}]_i$ when different concentrations of $[Mg^{2+}]_o$ were applied to the cells.

To examine the co-activation of CaSR by TNCA and $[Mg^{2+}]_o$ or $[Ca^{2+}]_o$, different concentrations of TNCA were placed in the experimental buffer with a fixed concentration of $[Ca^{2+}]_o$ and varying concentrations of $[Mg^{2+}]_o$, or vice versa, as described in the results section. The effects of other ligands were analyzed by comparing the changes in $[Ca^{2+}]_i$ produced by $[Mg^{2+}]_o$ alone or by co-application of $Mg^{2+}$ with other ligands. The $EC_{50}$ of $[Mg^{2+}]_o$ obtained during incubation with various concentrations of TNCA is compared with that observed in the presence of $[Mg^{2+}]_o$ alone. The $EC_{50}$ changes were plotted as a function of TNCA concentration and the curve was fit to the Hill equation. The activation of CaSR by the TNCA, functioning as a co-agonist with $[Mg^{2+}]_o$, is indicated by the increasingly leftward-shifted $EC_{50}$ for $[Mg^{2+}]_o$ as the concentration of TNCA increases (FIG. 6).

Determination of ERK1/2 Phosphorylation.

The 5001 cell line stably expressing hCaSR was starved in serum-free DMEM medium supplemented with 0.2% (w/v) BSA overnight, followed by washing 3-times with HBSS and a subsequent 10 minute HBSS incubation after 12 hours. To induce ERK1/2 phosphorylation, varying concentrations of $[Mg^{2+}]_o$ (0-50 mM) or $[Ca^{2+}]_o$ (0-30 mM) with or without 0.5 mM TNCA were added to cells and incubated for 10 minutes at 37° C. The cells were then lysed with Pierce RIPA buffer (ThermoFisher Scientific). Total protein concentration was measured using the BioRad assay. Lysates containing 100 µg of total protein were loaded onto 4-20% gradient SDS-PAGE gels for separation. After electrophoresis, proteins on the gel were transferred to nitrocellulose membranes and further analyzed by western blotting. Anti-phospho-p44/42 ERK (1:1000 dilution) and anti-p44/42 (1:2000) polyclonal antibodies were utilized as probes to detect the phosphorylated ERK1/2 and total ERK1/2 respectively. A chemiluminescent detection method (AP Conjugate Substrate Kit, Bio-Rad) was applied to detect phosphor-ERK1/2 and total-ERK1/2. The respective bands on western blots were evaluated by densitometry. The $EC_{50}$ of $[Mg^{2+}]_o$- or $[Ca^{2+}]_o$-dependent responses were obtained by fitting the $[Mg^{2+}]_o$ or $[Ca^{2+}]_o$ concentration-response curves with the Hill equation (Eq.1).

Results

Figures 7A, 7B, 7C:
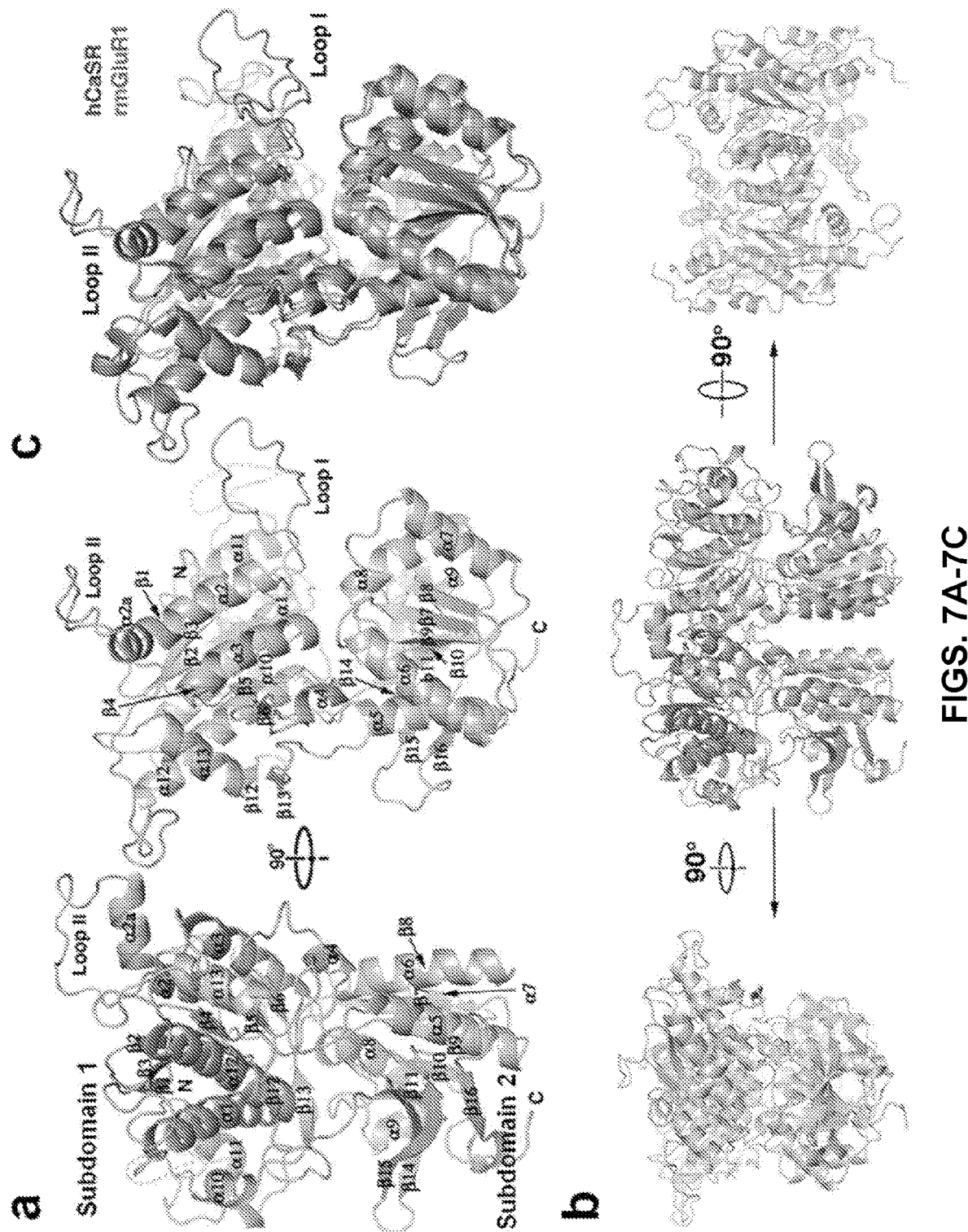
FIGS. 7A-7C show (FIG. 7A) Monomeric hCaSR-ECD with labeled secondary structural elements.
Figure 10A:
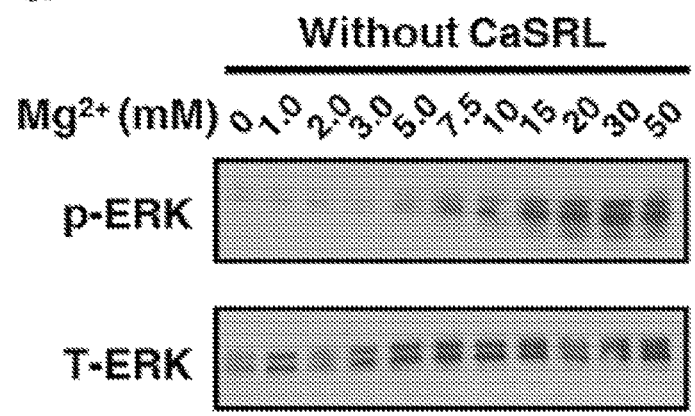
FIGS. 10A-10C show gel images (FIGS. 10A-10B) and a graph (FIG. 10C) demonstrating CaSR mediated ERK1/2 activation. [Mg$^{2+}$]$_o$-activated ERK1/2 signaling in HEK293 cells stably transfected with CaSR (10A) in the absence or (10B) in the presence of 0.5 mM TNCA.
Figure 10B:
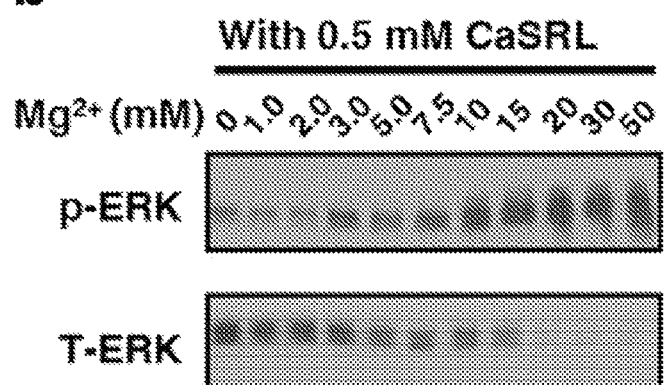
Figure 10C:
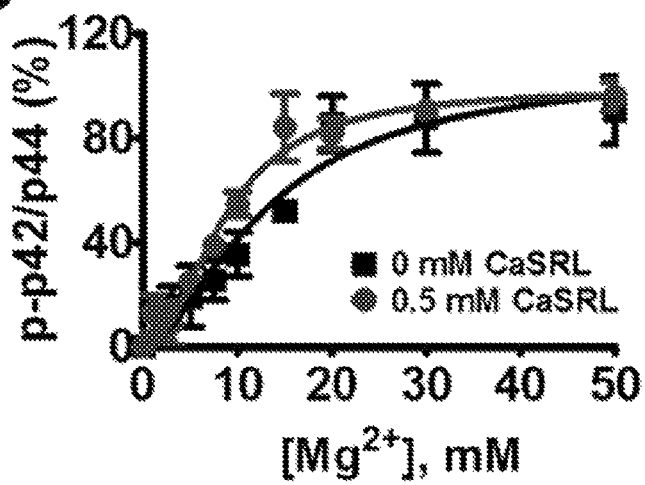

The Venus fly trap (VFT) domain of the human calcium-sensing receptor ECD (hCaSR-ECD, residues 20-541) expressed in HEK293S (GnT1-) cells was crystallized in the presence of 200 mM $Mg^{2+}$ and 10 mM $Ca^{2+}$. The structure was solved by molecular replacement using the structure of mGluR2 (PDB ID 4XAQ) as the search template (FIGS. 7A and 8). hCaSR-ECD contains two globular lobes with an overall structure similar to other cGPCR family members, despite a low sequence similarity between these cGPCR family members (about 20-30%) (FIG. 1)[14]. Both the large lobe (subdomain 1) and the small lobe (subdomain 2) are typical α/β folds where the central parallel β-strands are sandwiched by α-helices. hCaSR-ECD forms a homodimer in solution (FIG. 2) and in the crystal structure, with both protomers in a closed conformation (FIG. 7B) similar to the equivalent closed conformation of mGluR1 bound with glutamate (r.m.s.d. of 1.24 Å for C (FIG. 7C). In addition, the direct and extensive homodimeric subdomain 2 interactions in the hCaSR-ECD are analogous to those observed in the mGluR2 dimer with a bound agonist (PDB code: 4XAQ), strongly suggesting that the hCaSR-ECD crystal structure represents an active conformation (FIG. 9)[15].

Figures 11, 12:
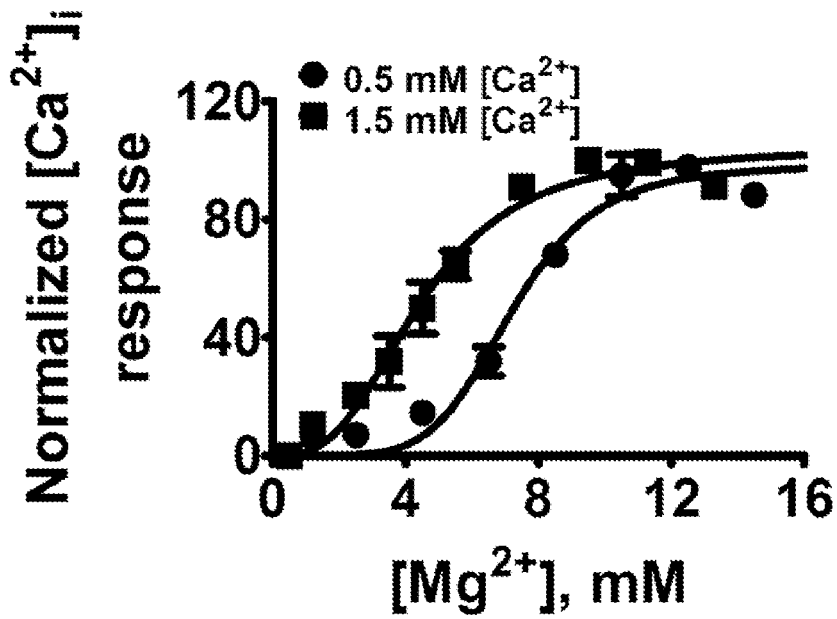
FIG. 11 shows a graph demonstrating [Ca$^{2+}$]$_i$ responses of CaSR stimulated by increasing [Mg$^{2+}$]$_o$. In the presence of 0.5 mM (circles) or 1.5 mM (squares) [Ca$^{2+}$]$_o$, [Ca$^{2+}$]$_i$ was monitored using Fura-2 during stepwise increases of [Mg$^{2+}$]$_o$. The ratio of the intensity of light emitted at 510 nm upon excitation with 340 or 380 nm was normalized to its maximum response. The [Mg$^{2+}$]$_o$ concentration response curves were fitted using the Hill equation (Eq. 1).
FIG. 12 shows a table demonstrating EC$_{50}$ of [Mg$^{2+}$]$_o$ for stimulation of [Ca$^{2+}$]$_i$ signaling in the presence of different co-activators.
Figures 13A, 13B:
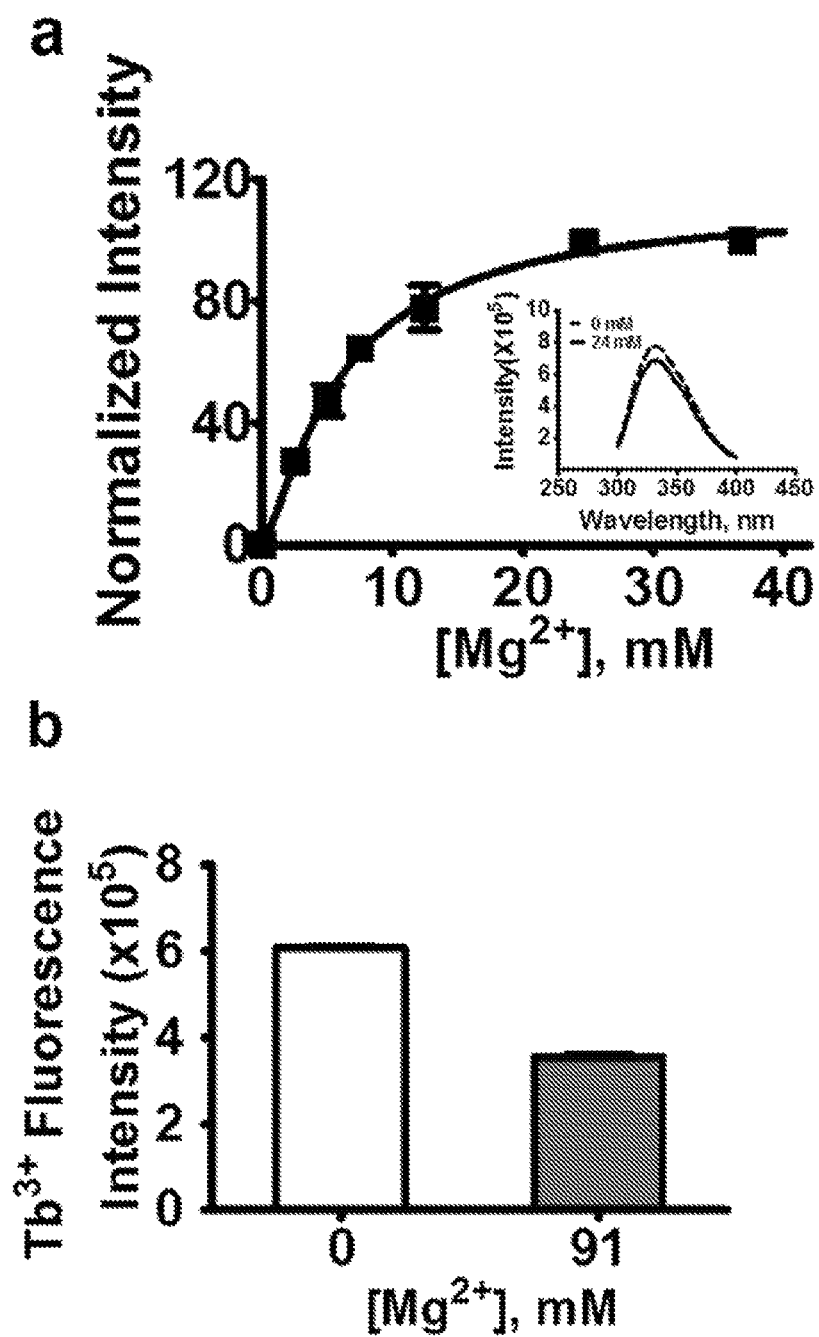
FIGS. 13A-13B show graphs demonstrating Mg$^{2+}$ binding to hCaSR-ECD. The magnesium titration was performed in HEPES buffer (10 mM HEPES, 120 mM NaCl and 10 mM KCl, pH 7.2) with a protein concentration of 2.0 μM.
Figure 14:
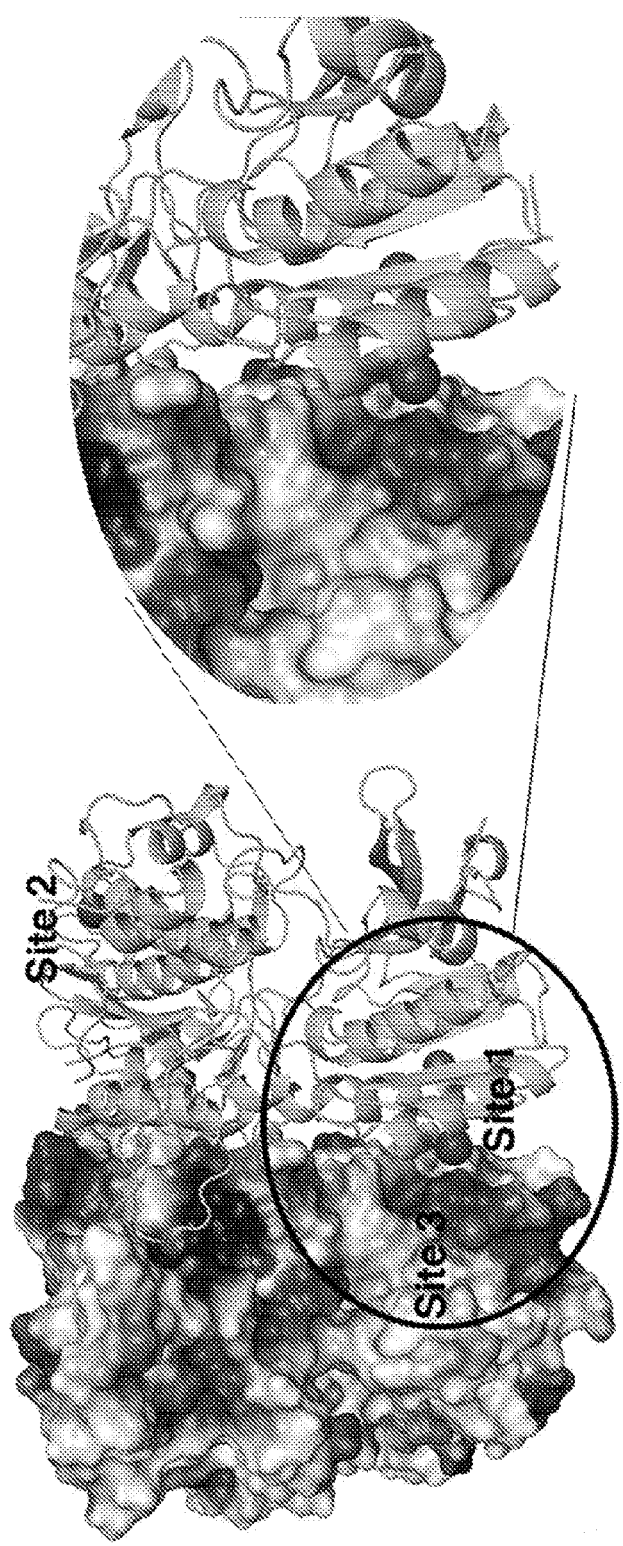
FIG. 14 can demonstrate metal binding at the "acidic patch." The electrostatic potential map of hCaSR-ECD is colored in accordance to electrostatic potential-red indicates negative potential, and blue positive potential. Mg$^{2+}$ is represented by hot pink spheres, while Gd$^{3+}$ is shown as blue spheres. The large surface with negative potential at the dimerization interface of subdomain 2 is referred as to "acidic patch", where both Mg$^{2+}$ and Gd$^{3+}$ bind.
Figure 15A:
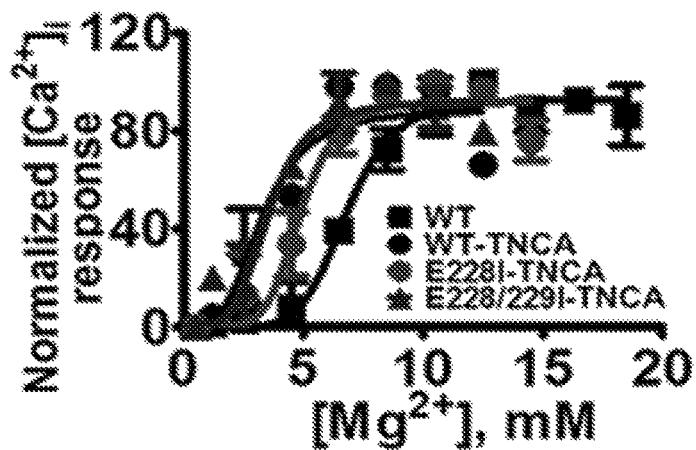
FIGS. 15A-15D show graphs (15A-15C) and images (FIGS. 15D-15G) demonstrating the TNCA (also denoted as TNCA) binding capability to hCaSR-ECD.
Figure 15B:
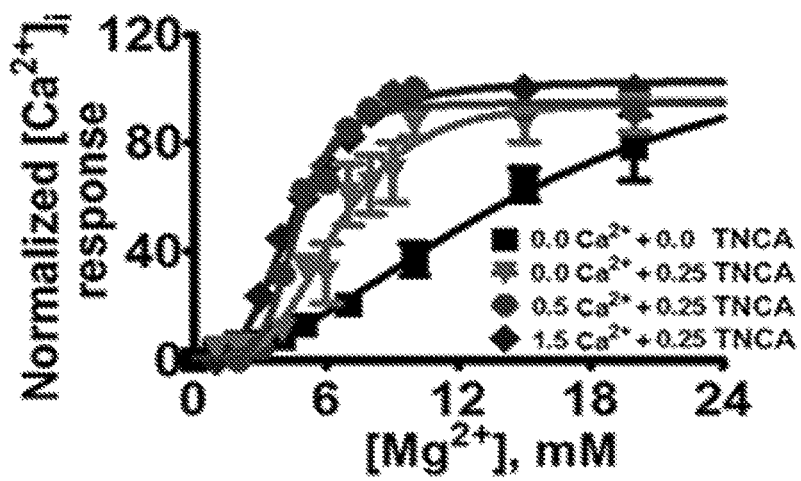
Figure 15C:
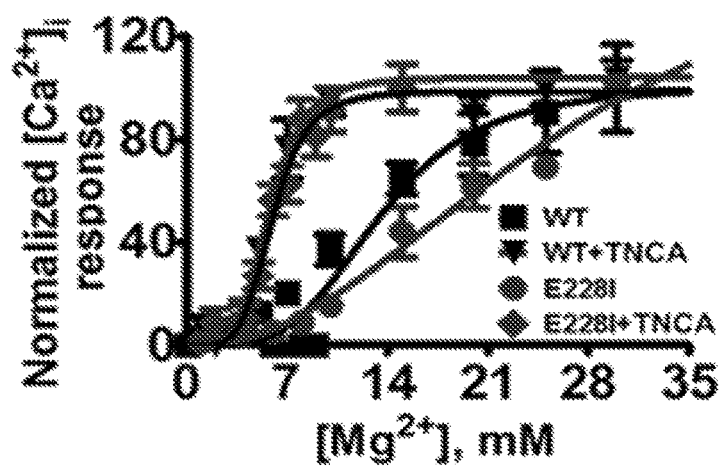
Figure 15D:
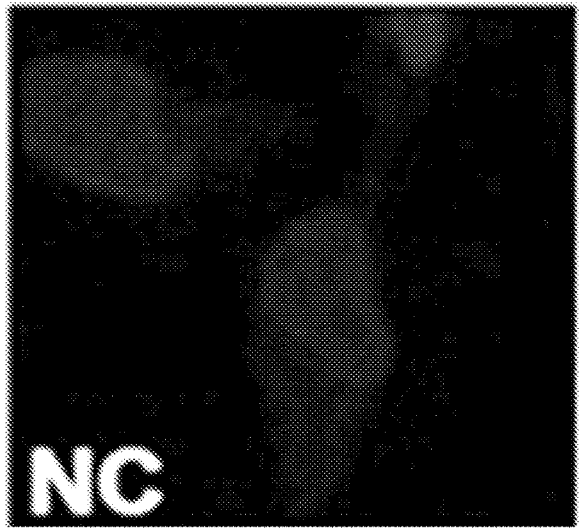
Figure 15E:
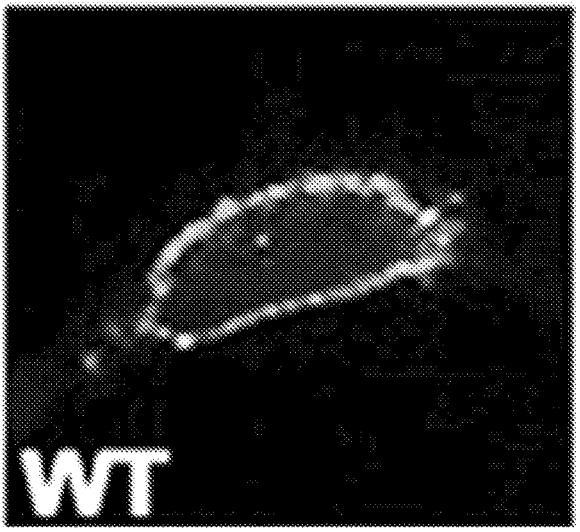
Figure 15F:
Figure 15G:
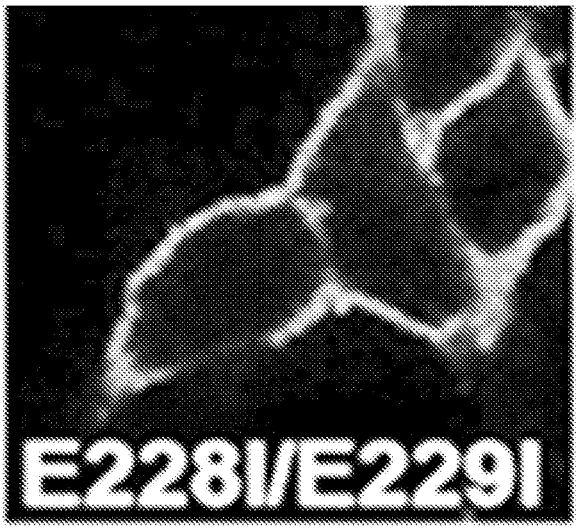

The data indicate that $Mg^{2+}$ binds to hCaSR-ECD and elicits CaSR-mediated $[Ca^{2+}]_i$ signaling and ERK1/2 phosphorylation in CaSR-expressing cells with a lower potency than $Ca^{2+}$ (FIGS. 3A, 3B, 5C, and 10A-10C)[16]. Similar to $[Ca^{2+}]_o$ activation, $[Mg^{2+}]_o$ activation is further potentiated by the known CaSR co-agonist, L-Phe (FIG. 5F)[5,7]. Importantly, $[Ca^{2+}]_o$ potentiates $[Mg^{2+}]_o$-stimulated intracellular responses mediated by CaSR, as the increase of $[Ca^{2+}]_o$ from about 0.5 to about 1.5 nM results in reduction of the $EC_{50}$ of $[Mg^{2+}]_o$ from 7.2±0.4 mM to 4.5±0.3 mM for stimulation of $[Ca^{2+}]_i$ signaling. These results suggest that there is an additive effect of both $Ca^{2+}$ and $Mg^{2+}$, and that they share a similar activation mechanism (FIGS. 3A, 11, and 12)[16,17]. The binding of $Mg^{2+}$ can be visualized by the reduction of intrinsic Trp fluorescence upon addition of $Mg^{2+}$ to the purified ECD and a reduction of $Tb^{3+}$-sensitized energy transfer by $Mg^{2+}$ competition (FIGS. 13A-13B). In the crystal structure, two $Mg^{2+}$-binding sites were identified at positions designated site 1 and site 2 (FIG. 3B). Site 1 is located at the dimerization interface of subdomain 2 and the bound $Mg^{2+}$ coordinates with S240 and four water molecules with an ideal geometry for a $Mg^{2+}$ ion. Notably, site 1 is surrounded by highly conserved residues (E228, E231 and E241*) ("*" means from the other protomer) within 5 Å from the "acidic patch" composed of negatively charged residues on subdomain 2 (FIG. 14). Site 2 is found on the periphery of subdomain 1, coordinated by S84 and backbone interactions with I81, L87, L88 as well as two water molecules. An equivalent cation binding site has been observed in mGluR [20]. Site 2 is found on the periphery of subdomain 1 and an equivalent cation-binding site has been observed in mGluR[14] and, without being bound to theory, likely plays a structural role. To locate additional high off-rate metal binding sites, we $Gd^{3+}$-derived crystals were generated and identified another metal-binding site (site 3) on the "acidic patch" in the proximity of subdomain 2 dimerization interface (FIG. 3C) and adjacent to the $Mg^{2+}$-binding site 1. Site 3 largely overlaps with a previously predicted $Ca^{2+}$-binding site III[18]. Mutation of site 3 coordinating residue (E228I or E228I/E229I double mutant) reduced $Ca^{2+}/Mg^{2+}$-sensing as well as $Mg^{2+}$-evoked intracellular $Ca^{2+}$ mobilization. These results suggest a role of these metal-binding sites at the "acidic patch" in both metal-sensing[18] and in regulation of CaSR function (FIGS. 3G, 14, and 15A-15D, and 16-17).

Figure 5B:
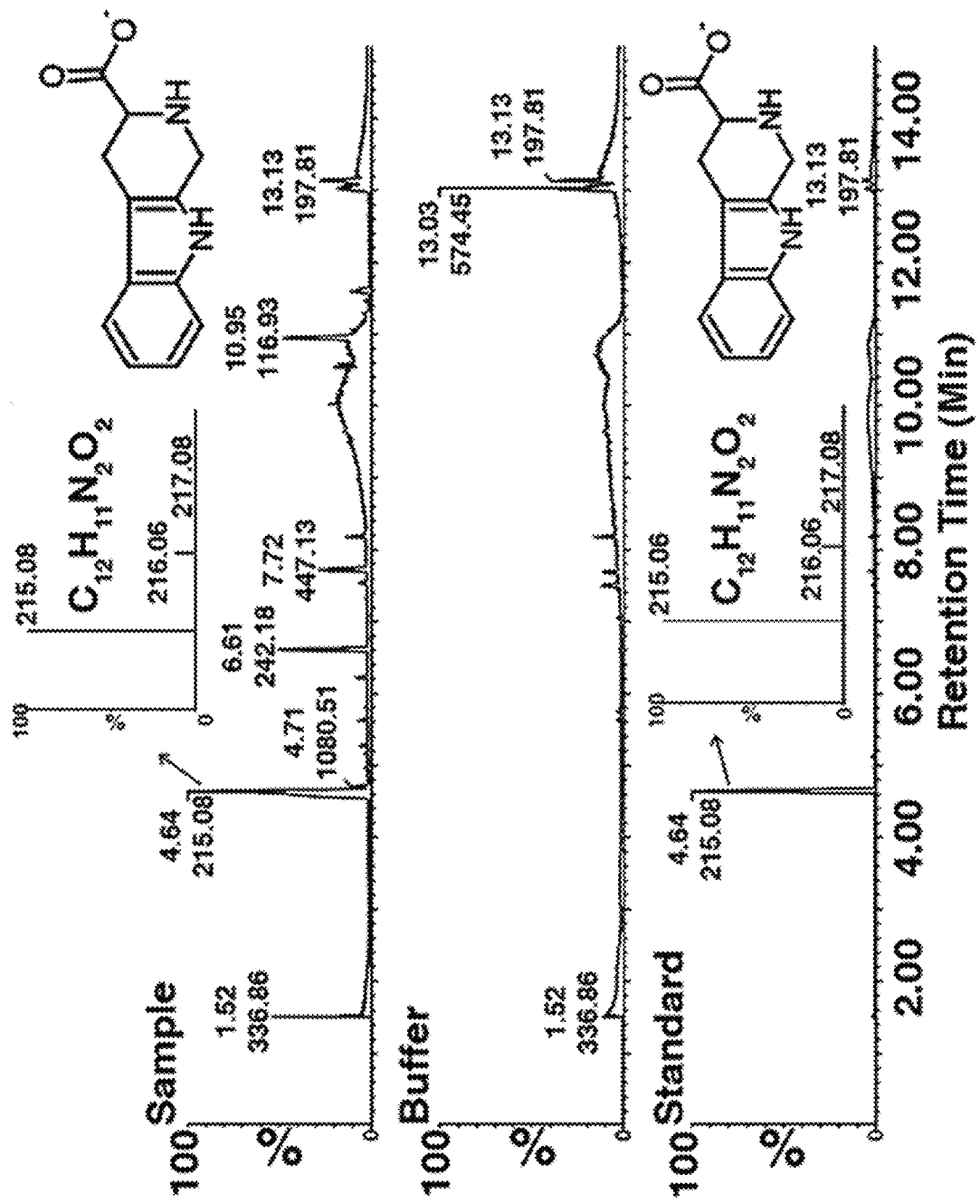
Figures 18A, 18B:
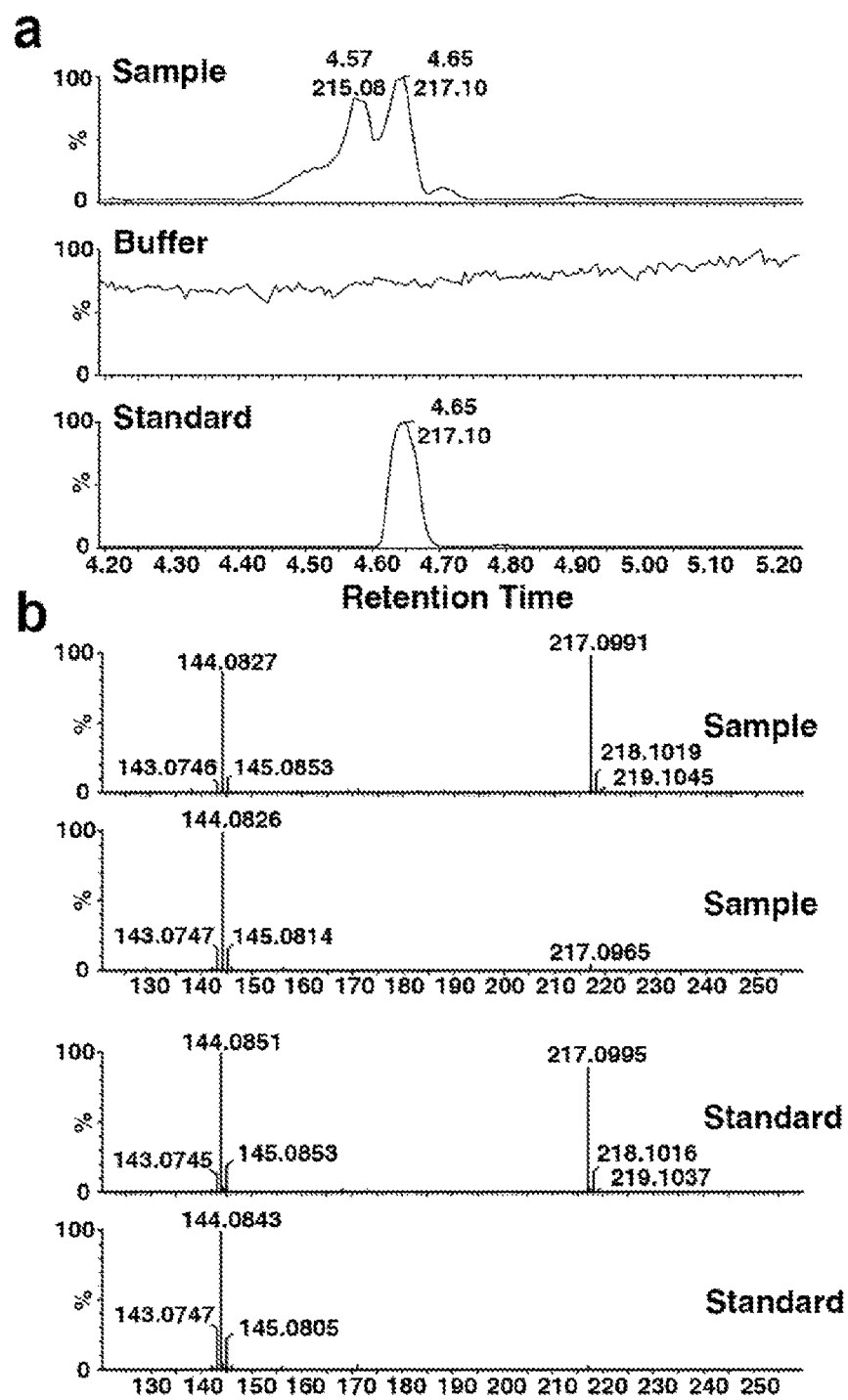
FIGS. 18A-18B show graphs demonstrating the identification of TNCA. The structure of TNCA is shown in FIGS. 5A-5B.

Unexpectedly, an elongated planar electron density was observed at the hinge between the two subdomains where orthosteric ligand binding is thought to occur (FIG. 5A). No naturally occurring CaSR ligands or reagents that were used in sample preparation, crystallization or any currently known CaSR ligands fit the density well, suggesting a novel CaSR ligand (High-resolution liquid chromatography-electrospray ionization-mass spectrometry (LC-ESI-MS) of the purified protein preparation (FIG. 5B) identified a species eluting at ~4.65 min with m/z 215.0824 in negative-ion mode. The predicted elemental formula based on the observed mass corresponds to $C_{12}H_{11}N_2O_2$ (calculated mass=215.0821, m=1.4 ppm) (FIGS. 5B and 18A-18B). A search of PubChem identified a tryptophan derivative, L-1,2,3,4-tetrahydronorharman-3-carboxylic acid (hereinafter "TNCA") with the predicted $M_r$ and a shape of the observed density. When compared to tryptophan, TNCA contains one extra carbon atom linking the amine nitrogen atom and the C2 atom of the indole ring. TNCA can be detected in a various foods and biological systems and is likely produced by tryptophan reacting with formaldehyde in humans, and as such, is perhaps generated during production of the recombinant protein in human embryonic kidney cells. Elution time, molecular weight and MS fragmentation of synthetic TNCA matched those of CaSR ligand, confirming the identity of the CaSR ligand (FIGS. 5B and 18A-18B).

Figures 5C, 5D, 5E, 5F, 5G, 5H:
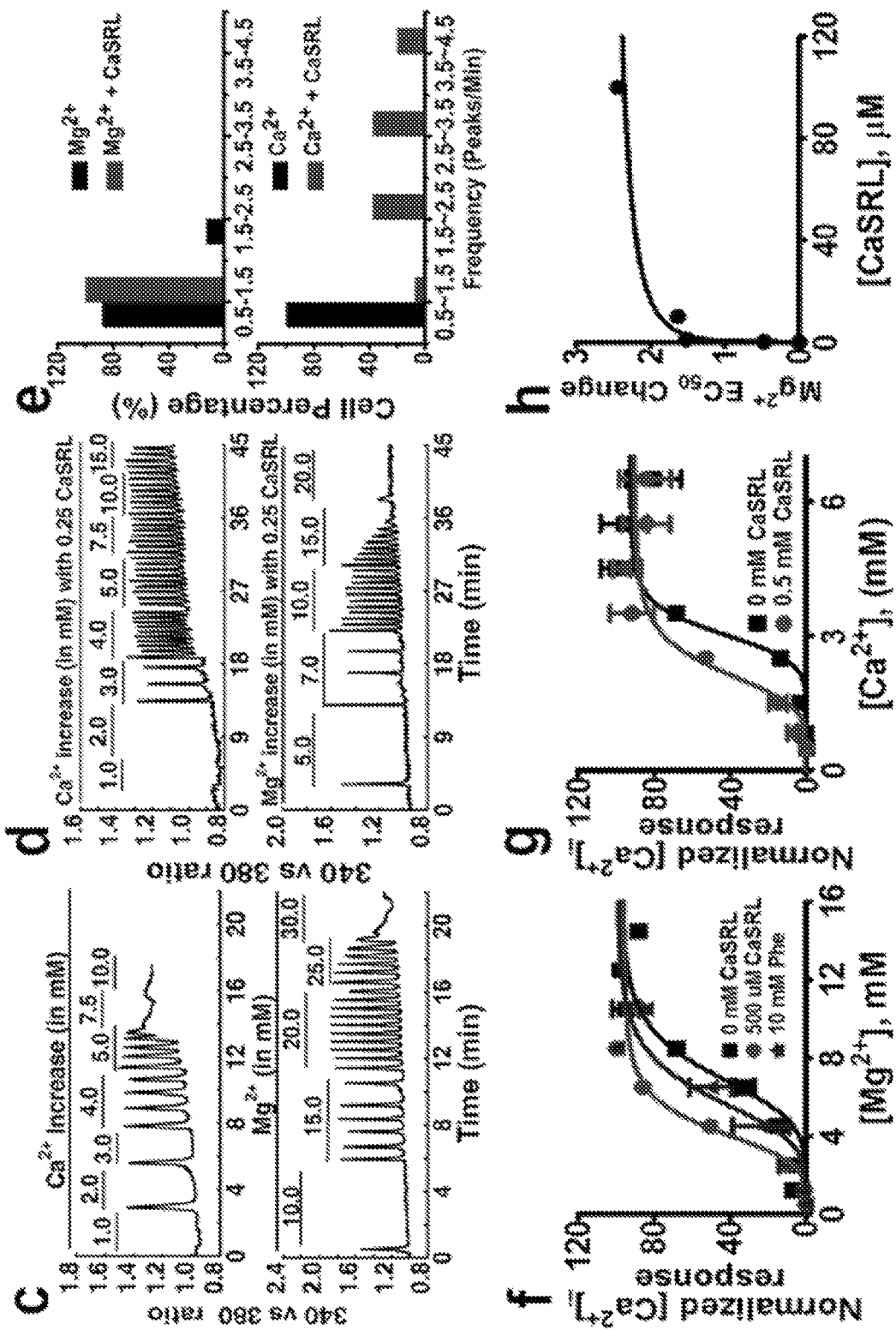

TNCA is a strong co-agonist with $[Mg^{2+}]_o$ in activating $[Ca^{2+}]_i$ oscillations and ERK1/2 phosphorylation (FIGS. 5D-5F and 15A-15D). Similar to Trp and other amino acids, addition of exogenous TNCA alone cannot activate the receptor. However, TNCA is greater than 1000-fold more potent than Phe in reducing the $EC_{50}$ for $[Mg^{2+}]_o$ or $[Ca^{2+}]_o$ activation of $[Ca^{2+}]_i$ signaling both in WT (wild-type) and mutant CaSRs (FIGS. 5F-5G), with an apparent $EC_{50}$ of ≥2 µM (FIG. 5H). The apparent $EC_{50}$ of TNCA was determined indirectly through the $EC_{50}$ change of $[Mg^{2+}]_o$ when incubated with different concentrations of TNCA (FIGS. 5F-5H). As the bound TNCA can be partially replaced by incubation with 150 mM Phe as assessed by MS (FIG. 19), TNCA and Phe likely share the same binding site in the CaSR-ECD. Taken together, TNCA is a novel, high affinity co-agonist of CaSR in activation of both $[Ca^{2+}]_i$ signaling and ERK activity.

Figures 20A, 20B:
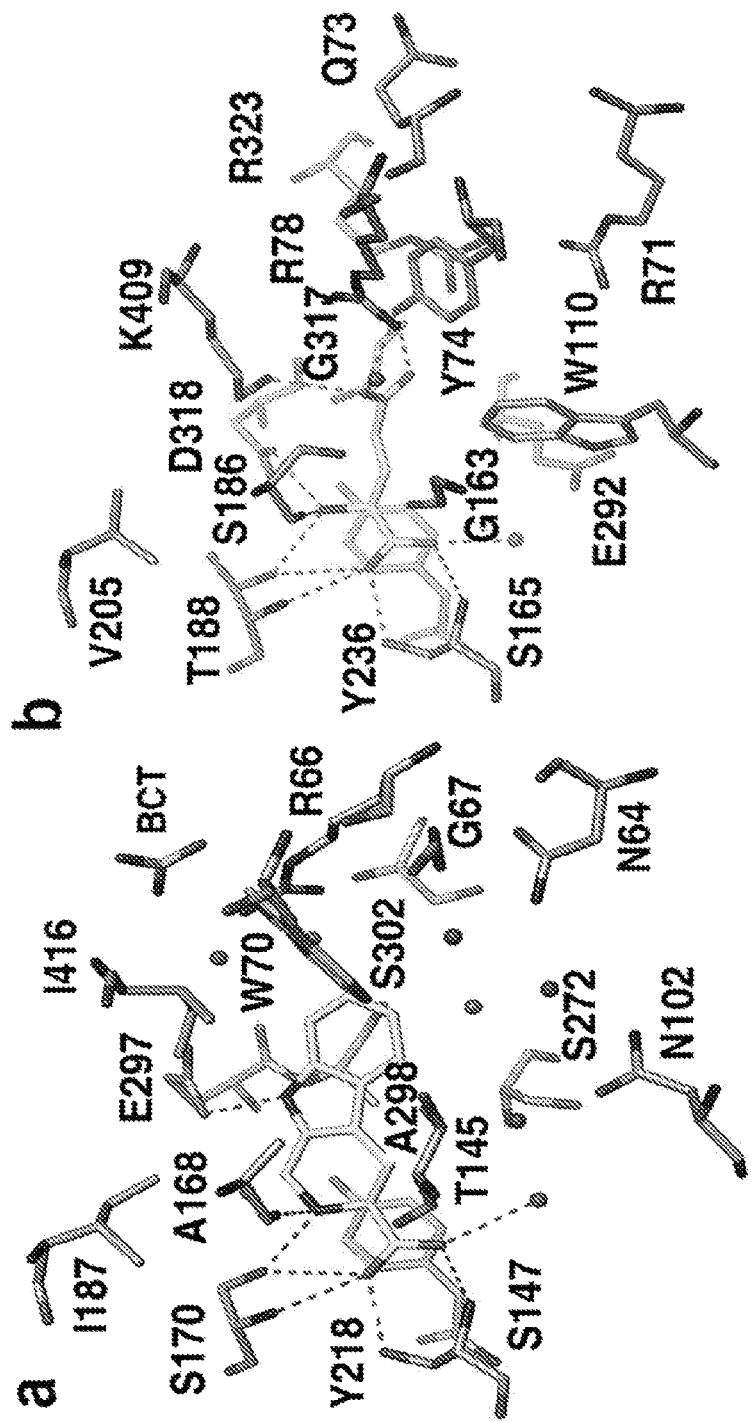
FIG. 20A-20B demonstrates a structural comparison of CaSR ligand binding site with that of mGluR1. The amino acid backbone of TNCA adopts a similar conformation as Glu in mGluR1 through extensive interactions with S147, A168, S170, and Y218 (S156, S186, T188 and Y236 in mGluR1). However, hCaSR and mGluR1 recognize the side chains of their preferred ligands differently: (1) Two positively charged residues in mGluR1 (R78 and K409) that associate with the carboxylate group of the Glu ligand are replaced in hCaSR by W70 and I416 interacting with the indole ring of TNCA. (2) Bulky residues (Y74, W110 and R323) limiting the mobility of the Glu side chain are replaced by smaller residues in hCaSR (G67, N102 and S302). As a result, the size of the ligand binding pocket of hCaSR is significantly greater than that of mGluR1, consistent with the preference of CaSR for larger ligands. The ligands (20A) TNCA in hCaSR-ECD and (20B) Glu in mGluR1 are highlighted in yellow. The red balls represent water molecules. Note that a bicarbonate anion (BCT) is in close proximity to TNCA. The hydrogen bonds are depicted by dashed lines. (B, PDB code: 1 EWK).

CaSR strongly prefers aromatic amino acid ligands, such as Phe and Trp, over negatively charged Glu, the ligand for mGluRs. Structural comparison of the ligand-binding pocket in the hinge region between subdomains 1 and 2 of the hCaSR-ECD with that of mGluR1 reveals the structural basis of ligand selectivity (FIGS. 20A-20B). Although the amino acid backbone of TNCA adopts a similar conformation as Glu in mGluR1[14], through extensive interactions with S147, A168, S170 and Y218 (S156, S186, T188 and Y236 in mGluR1)[20,14] hCaSR and mGluR1 recognize the side chains of their preferred ligands differently. Two positively charged residues in mGluR1 (R78 and K409) that associate with the carboxylate group of the Glu ligand are replaced in hCaSR by W70 and I416, which interact with the indole ring of TNCA. Bulky residues (Y74, W110 and R323) limiting the mobility of the Glu side chain are replaced by smaller residues in hCaSR (G67, N102 and S302). As a result, the size of the ligand-binding pocket of hCaSR is significantly larger than that of mGluR1, consistent with the preference of CaSR for larger ligands. Unlike Trp, TNCA is in a fixed and presumably preferred conformation, accounting for the higher binding affinity than Trp.

Figures 19A, 19B, 19C:
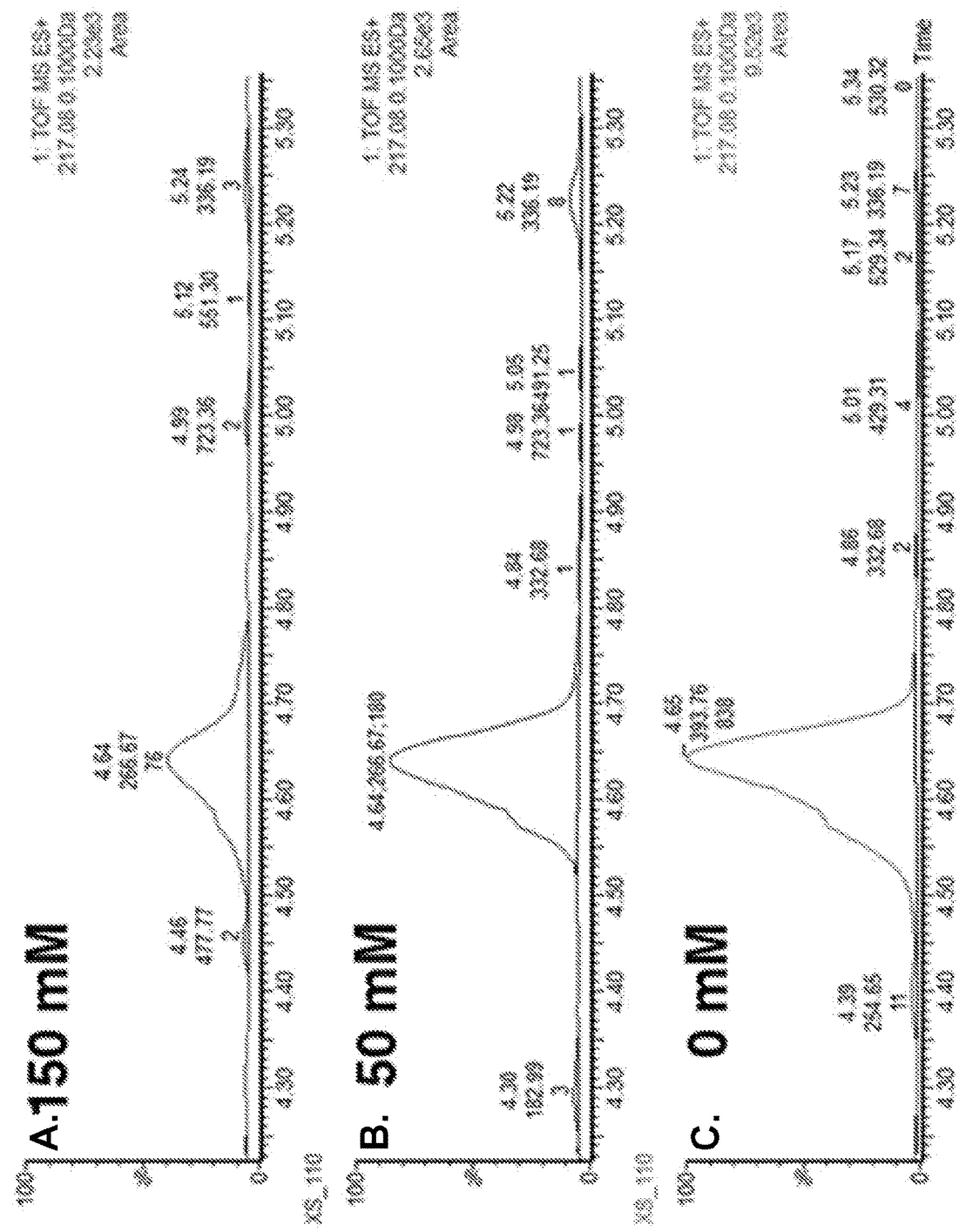
FIGS. 19A-19C shows graphs demonstrating replacement of TNCA by phenylalanine. With the increase of phenylalanine concentration (from 0 to 150 mM), the signal of TNCA (the peak eluted at 4.64 min) detected by MS decreases correspondingly, indicating that the binding site of Phe and that of TNCA are overlapping. The areas under the peaks are 838, 180 and 76, respectively.
Figure 21:
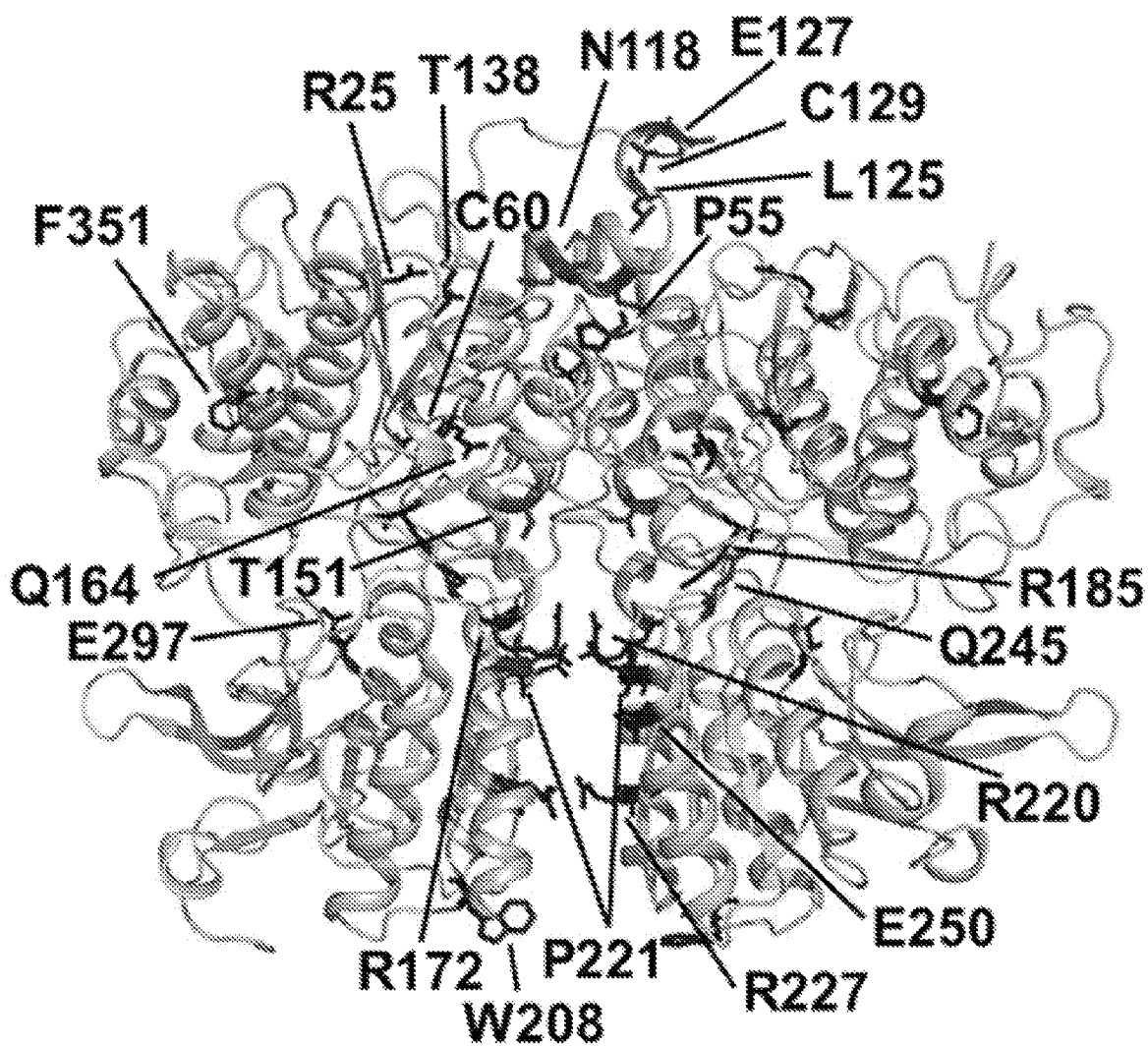
FIG. 21 demonstrates disease related mutations on CaSR ECD. Blue: Loss-of-function mutations associated with familial hypocalciuric hypercalcemia (FHH), Red: Gain-of-function mutations associated with autosomal dominant hypocalcemia (ADH).
Figure 22:
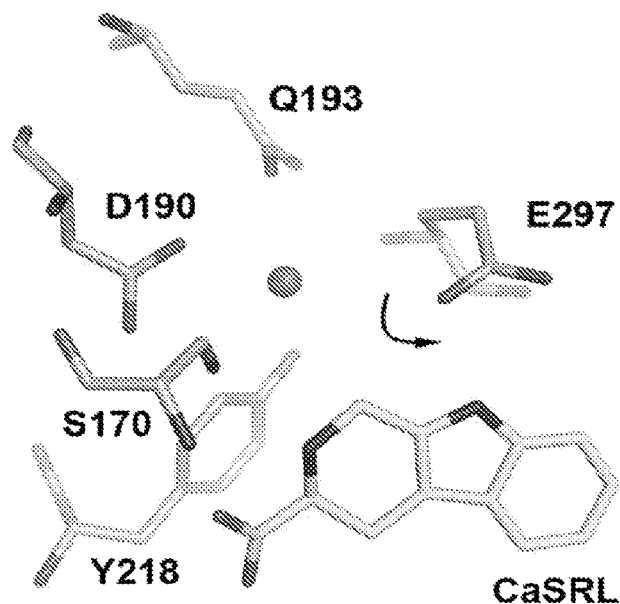
FIG. 22 can demonstrate a structure of the calcium binding "Site 1". A close inspection of the structure reveals that the side chain of E297, a residue predicted for $Ca^{2+}$ binding in the proposed "site 1", swings away from the other residues in "site 1" (S170, D190, Q193 and Y218), probably due to the extra carbon atom and the rigid structure of TNCA, ultimately resulting in its failure to capture $Ca^{2+}$ ion together with other "site 1" residues. Instead, E297 forms a hydrogen bond with the nitrogen atom on the indole ring of TNCA. In the crystal structure, the calcium-binding "site 1" is occupied by a water molecule (red sphere). The residues of the "site 1" and TNCA are depicted in stick mode. The arrow indicates that the side chain of E297 swings away from the proposed calcium binding site.
Figure 23:
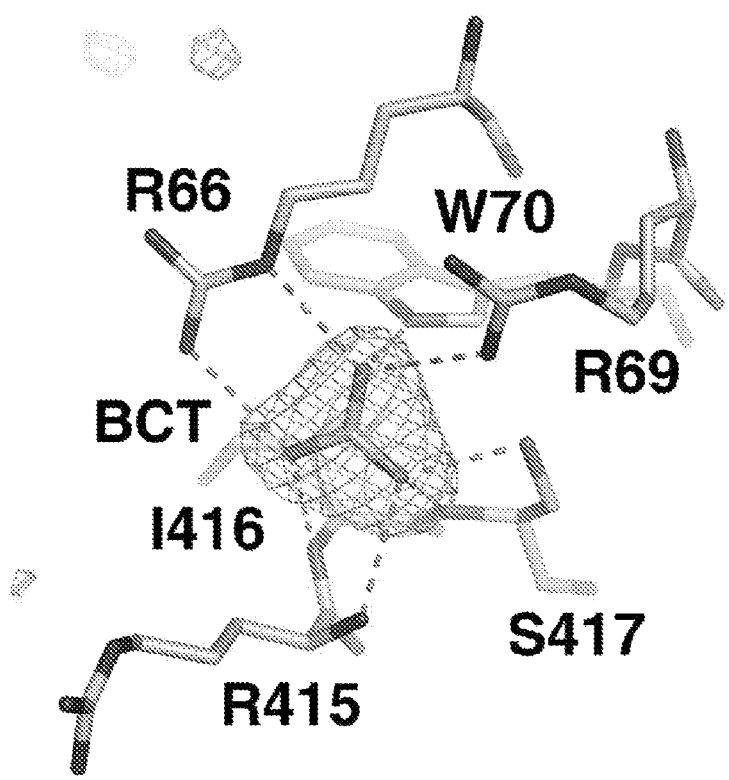
FIG. 23 can demonstrate a bicarbonate anion near the ligand binding site. The triangular planar-shaped electron density (Fo-Fc map at σ=4) is a bicarbonate anion, as there is no nitrate in the crystallization solution and the pH in the crystallization drop is 7.0. The bicarbonate anion is coordinated by the side chains of R66 (mutated in FHH and ovarian cancer), R69 (mutated in lung and endometrial cancer), W70 and S417, and the backbone amide nitrogen atoms of I416 and S417. Remarkably, R66, R69 and W70 are highly conserved in CaSR across species, but replaced by other residues in mGluRs. R66 and R69 are disease related residues. Alterations in pH over the range of 5.5-6.0 to 9 are known to modulate the activity of the CaSR, and the bound bicarbonate identified here could potentially contribute to the pH sensitivity of the CaSR.

Mapping of disease-associated mutations on the structure of hCaSR-ECD shows that the mutations are clustered in two regions: the hinge region between subdomains 1 and 2, and the dimerization interface (FIG. 21)[20]. Indeed, our structural and functional data strongly support the pivotal roles of these two regions in CaSR function. The hinge region between subdomains 1 and 2 harbors the binding site of TNCA, which supports its role as a co-agonist of CaSR. Two other co-agonists, Phe and Trp, likely bind in the same position (FIG. 19). Metal-binding at the previously proposed "site 1" for $Ca^{2+}$ was not observed[6,4,28]. A close inspection of the structure reveals that the side chain of E297, a critical residue predicted for $Ca^{2+}$ binding in the proposed "site 1", swings away from the other residues in "site 1" (S170, D190, Q193 and Y218), probably[6,18,21]. Without being bound to theory, it is postulated that this is due to the extra carbon atom and the rigid structure of TNCA, ultimately resulting in its failure to capture $Ca^{2+}$ ion together with other "site 1" residues (CaSR ligand, which affects the conformation of E297 and blocks the binding of $Ca^{2+}$) (FIG. 22). Nevertheless, the role of E297 in $Ca^{2+}$-sensing has been supported by previous mutational studies[7,24] and in abrogated $Mg^{2+}$-sensing of the E297I mutant (FIGS. 16-17). Interestingly, a bicarbonate anion was also identified at the hinge region in proximity to TNCA, coordinated by the side chains of R66, R69, W70, and S417 and the backbone amide nitrogen atoms of I416 and S417 (FIGS. 20A-20B and 23), potentially contributing to the known pH sensitivity of CaSR[29].

Figures 24A, 24B, 24C:
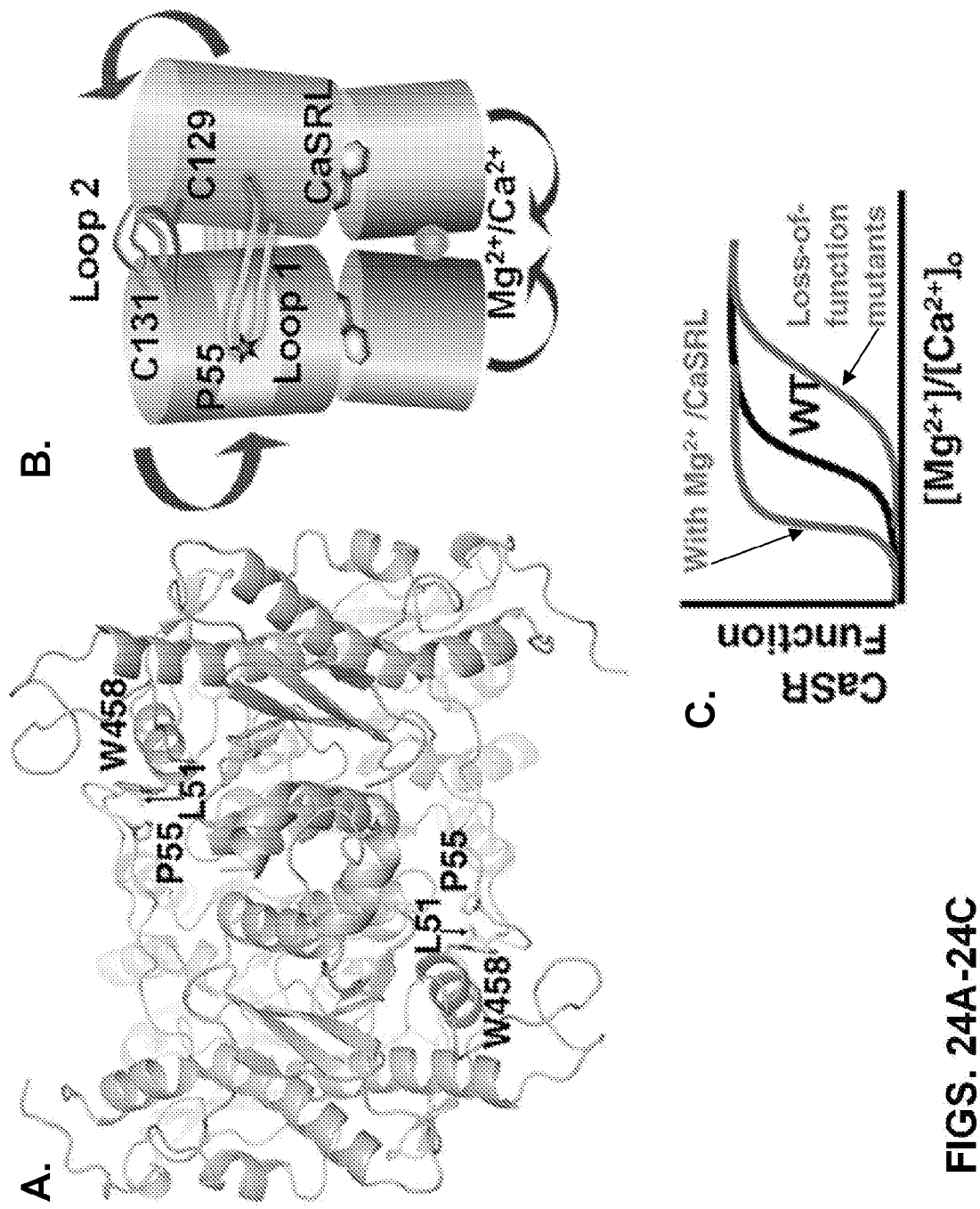
FIGS. 24A-24C can demonstrate key determinants for the molecular basis of disease-associated mutations and regulation.

Several lines of evidence indicate a critical role of CaSR-ECD dimerization in CaSR function (FIGS. 7A-7C and 24A-24B). First, two metal-binding sites (site 1 and site 3) are identified within the "acidic patch" at the dimerization interface of subdomain 2 (FIGS. 3A-3G and 14). A double mutant of CaSR (E228I/E229I) in site 3 showed a significantly decreased responsiveness to $[Ca^{2+}]_o$, and the single E228I mutation also reduced activation of $[Ca^{2+}]_i$ oscillations induced by $[Mg^{2+}]_o$ as well as $Mg^{2+}$-binding, despite a similar level of membrane expression as WT CaSR (FIGS. 3A-3G, 10A-10B, 15A-15B, and 16-17)[6]. Without being bound to theory, these data strongly suggest a role of metal binding at the "acidic patch" in metal-sensing and signal transduction. Second, loop 1 and loop 2, both of which mediate subdomain 1 dimerization, are functionally important (FIG. 24A). Loop 2 following α2, which is largely disordered in mGluR, participates in two intermolecular disulfide bonds in CaSR through two conserved cysteine residues (C129 and C131)[11,23] (FIG. 24B). The N-terminal part of loop 2 forms a short α-helix (α2a) extended from α2 with a kink at N118. The α2a segments from each protomer embrace each other, likely stabilizing dimerization (FIG. 24A). As several activating ADH mutations (L125P/F, E127G/A/K, C129Y/F/S/R, and N118K) and one inactivating FHH mutation are present on loop 2, subdomain 1 dimerization that is facilitated by loop 2 appears involved in regulating the function of CaSR. Moreover, the highly conserved loop 1, which is significantly longer than the corresponding loop in mGluRs (FIG. 25A-25B), reaches across the dimerization interface to a hydrophobic surface on α13*. The hydrophobic interaction, primarily mediated by P55, L51 and W458* stabilizes an extended conformation of loop 1, and a conserved positively charged patch also appears to contributive to dimerization of subdomain 1 (FIG. 24A). Notably, mutation of P55 can result in FHH, indicative of this role of loop 1.

Figures 25A, 25B:
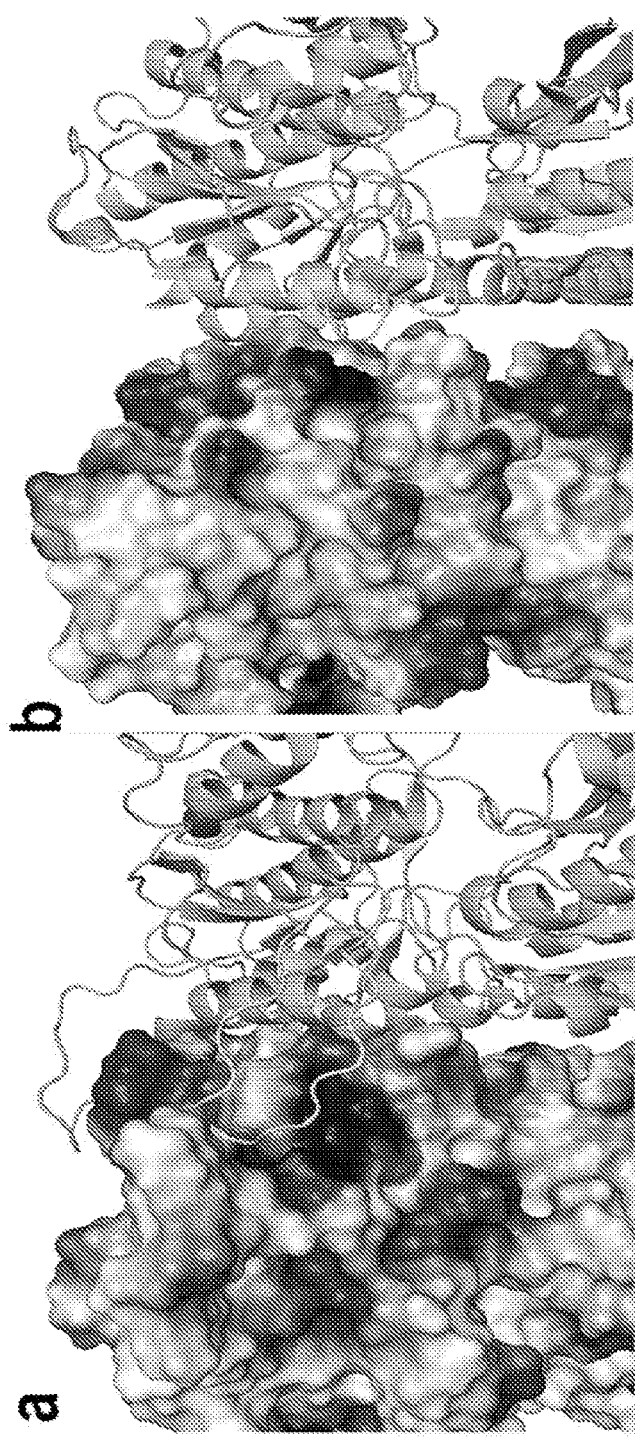
FIGS. 25A-25B can demonstrate a positively charged pocket for loop 1 association. Loop 1 for CaSR (FIG. 25A) and the corresponding loop in mGluR1 (FIG. 25B, PDB code 1 EWK) are highlighted. The electrostatic potential map is colored in accordance to charge, with red representing negative potential, and blue positive potential. Loop 1 in CaSR is significantly longer than the counterpart in mGluR1, reaching across the dimer interface to nestle itself into a positively charged pocket which is absent in mGluR1.

FIG. 24A summarizes the present model for receptor activation supported by this Example. The presumed conformational change induced by ligand/metal-binding at the hinge region between subdomains 1 and 2, together with homodimerization of protomer subdomains 1 facilitated by loops 1 and loop 2, promotes the approach of the subdomains 2 from the respective protomers. By neutralizing the repulsive effects of the conserved and negatively charged "acidic patch", metal-binding would stabilize subdomain 2 interactions (FIG. 25A-25B). Dimerization of subdomain 2 is also critical for activation of mGluRs and GABAB receptors[24,25], and therefore it appears to be a common activation mechanism among cGPCRs that presumably leads to conformational changes of the transmembrane domain, through which the intracellular signal cascades are initiated.

References for Example 1

1. E. M. Brown et al., *Nature* 366, 575 (1993).
2. M. P. Grant, A. Stepanchick, A. Cavanaugh, G. E. Breitwieser, *Sci. Signal* 4, 78 (2011).
3. E. A. Permyakov, R. H. Kretsinger, *J. Inorg. Biochem.* 103, 77 (2009).
4. Y. Kubo, T. Miyashita, Y. Murata, *Science.* 279, 1722 (1998).
5. A. D. Conigrave, S. J. Quinn, E. M. Brown, *Proc. Natl. Acad. Sci. U.S.A.* 97, 4814 (2000).
6. Y. Huang et al., *J. Biol. Chem.* 282, 19000 (2007).
7. C. Zhang et al., *J. Biol. Chem.* 289, 5296 (2014).
8. B. W. Bapty et al., *Kidney Int.* 53, 583 (1998).
9. A. L. Magno, B. K. Ward, T. Ratajczak, *Endocr. Rev.* 32, 3 (2011).
10. E. M. Brown, R. J. MacLeod, *Physiol. Rev.* 81, 239 (2001).
11. W. Chang, D. Shoback, Cell Calcium 35, 183 (2004).
12. N. J. Fudge, C. S. Kovacs, *BMC Physiol.* 4, 5 (2004).
13. S. C. Hebert, *Kidney Int.* 50, 2129 (1996).
14. C. Ho et al., *Nat. Genet.* 11, 389 (1995).
15. A. M. Hofer, E. M. Brown, *Nat. Rev. Mol. Cell Biol.* 4, 530 (2003).
16. M. Bai, *Int. J. Mol. Med.* 4, 115 (1999).
17. K. Ray et al., *J. Biol. Chem.* 274, 27642 (1999).
18. Y. Suzuki, E. Moriyoshi, D. Tsuchiya, H. Jingami, *J. Biol. Chem.* 279, 35526 (2004).
19. S. Pidasheva, L. D'Souza-Li, L. Canaff, D. E. Cole, G. N. Hendy, *Hum. Mutat.* 24, 107 (2004).
20. N. Kunishima et al., *Nature* 407, 971 (2000).
21. J. A. Monn et al., *J. Med. Chem.* 58, 1776 (2015).
22. S. J. Quinn et al., *Am. J. Physiol. Endocrinol. Metab.* 304, E724 (2013).
23. S. Ferre, J. G. Hoenderop, R. J. Bindels, *Kidney Int.* 82, 1157 (2012).
24. Y. Huang et al., *Biochemistry* 48, 388 (2009).
25. T. Herraiz, J. Galisteo, C. Chamorro, *J. Agric. Food Chem.* 51, 2168 (2003).
26. F. M. Hannan et al., *Hum. Mol. Genet.* 21, 2768 (2012).
27. F. M. Hannan, R. V. Thakker, *Best Pract. Res. Clin. Endocrinol. Metab.* 27, 359 (2013).
28. C. Silve et al., *J. Biol. Chem.* 280, 37917 (2005).
29. S. J. Quinn, M. Bai, E. M. Brown, *J. Biol. Chem.* 279, 37241 (2004).
30. H. Minami et al., *Fresenius' journal of analytical chemistry* 370, 855 (2001).
31. D. Tsuchiya, N. Kunishima, N. Kamiya, H. Jingami, K. Morikawa, *Proc. Natl. Acad. Sci. U.S.A.* 99, 2660 (2002). *Nature* 504, 254 (2013).
33. E. F. Nemeth, W. G. Goodman, *Calcif. Tissue Int.*,
32. Y. Geng, M. Bush, L. Mosyak, F. Wang, Q. R. Fan, (2015).
34. C. Zhang et al., *J Biol Chem* 289, 33529 (2014).
35. L. Meng et al., *J. Biol. Chem.* 288, 34680 (2013).
36. Z. Otwinowski, W. Minor, *Methods Enzymol.* 276, 307 (1997).
37. P. D. Adams et al., *Acta Crystallogr.* 66, 213 (2010).
38. P. Emsley, B. Lohkamp, W. G. Scott, K. Cowtan, *Acta Crystallogr.* 66, 486 (2010).
39. M. D. Winn et al., *Acta Crystallogr.* 67, 235 (2011).
40. W. Yang, H. W. Lee, H. Hellinga, J. J. Yang, Proteins 47, 344 (2002).

Example 2

The discovery of the parathyroid $Ca^{2+}$-sensing receptor (CaSR) by Dr. Ed Brown (Collaborator) et al. in 1993 has established a new paradigm of $Ca^{2+}$ signaling [10]. Extracellular $Ca^{2+}$ $[Ca^{2+}_o]$ has been proposed to be a first messenger that regulates diverse cellular processes via CaSR and 14 other family C, G protein-coupled receptors (cGP-CRs), including metabotropic Glutamate receptors (mGluRs) and gamma-aminobutyric acid (GABA)B receptors. CaSRs have been reported to be present not only in the key tissues involved in extracellular $Ca^{2+}$ and $Mg^{2+}$ homeostasis (e.g., parathyroid, thyroid, kidney, bone) but also in diverse other, non-homeostatic tissues (e.g., brain, skin, etc.)[8, 11-23]. Functional cooperativity of CaSR (i.e., based on biological activity determined using functional assays), particularly the functional positive homotropic cooperative response to $[Ca^{2+}]_o$, is essential for the receptor's ability to respond over a narrow physiological range of $[Ca^{2+}]_o$ (1.1-1.3 mM)[24]. CaSR has an estimated Hill coefficient of 3-4 for its regulation of biological processes such as activating intracellular $Ca^{2+}$ signaling, inhibiting PTH release in parathyroid cells and stimulating calcitonin secretion in C-cells (FIGS. 26 and 27A-27B)[25].

Other extracellular mineral cations such as $Mg^{2+}$ as well as amino acids are able to function as agonists and co-agonists of CaSR to regulate/potentiate the $[Ca^{2+}]_o$-induced activation of the CaSR. L-amino acids, especially aromatics, under physiological conditions potentiate the high $[Ca^{2+}]_o$-elicited activation of the CaSR by altering the EC50 values for $[Ca^{2+}]_o$-evoked $[Ca^{2+}]_i$ responses via positive heterotropic functional cooperativity [26-28]. This capability of CaSRs in integration of both divalent cations and other different extracellular stimuli such as amino acids [29] are also shared by all other cGPCRs [30-34].

Figure 26:
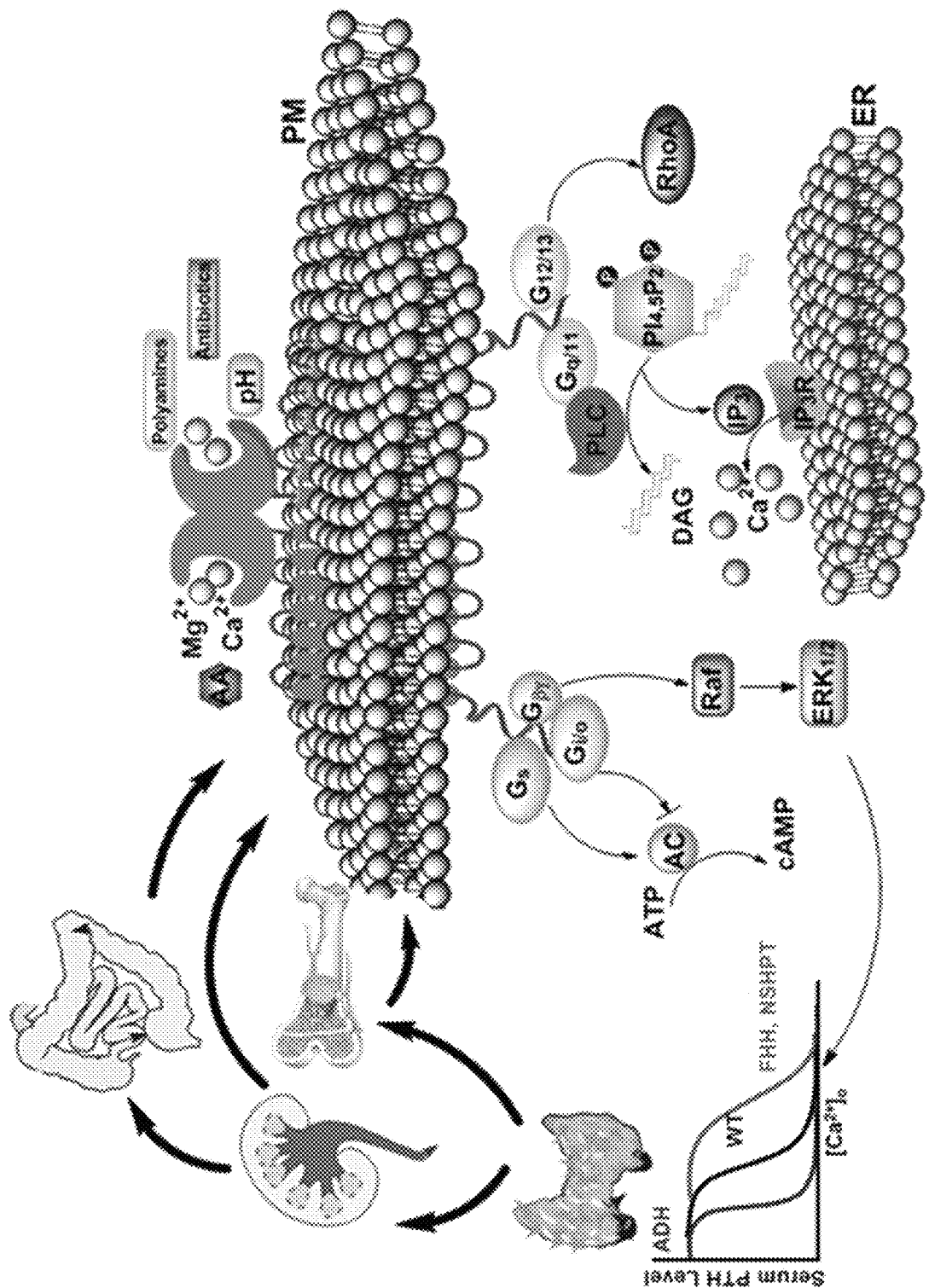
FIG. 26 demonstrates that CaR is a pleiotropic receptor for four G protein-mediated intracellular signaling pathways (Gq/11, Gi/o, Gs, and G12/13).
Figure 27A:
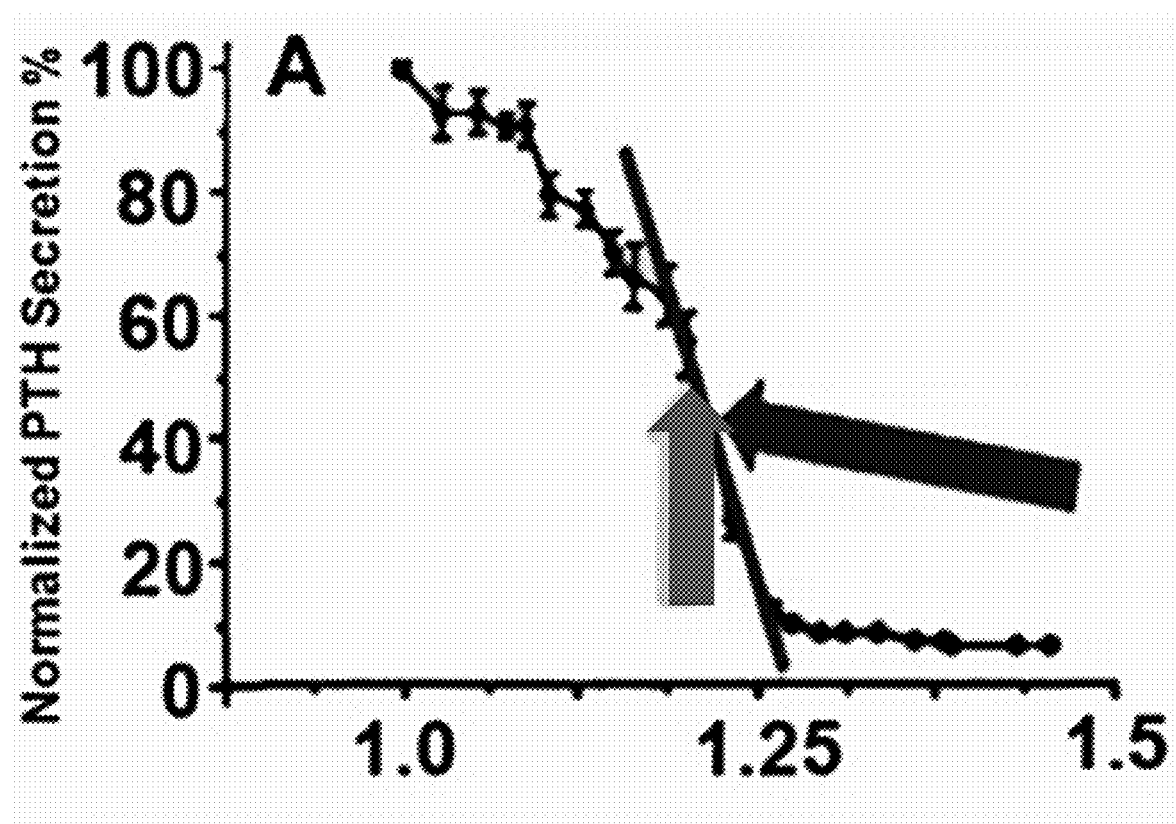
FIGS. 27A-27B show graphs demonstrating cooperative responses of PTH (FIG. 27A) and intracellular calcium responses (FIG. 27B) to extracellular calcium. Arrow: $Ca^{2+}$ set point. L-Phe potentiated $[Ca^{2+}]_o$ induced $[Ca^{2+}]_i$ oscillations by change functional cooperativity. Disease mutations around calcium binding sites alters functional cooperativity.
Figure 27B:
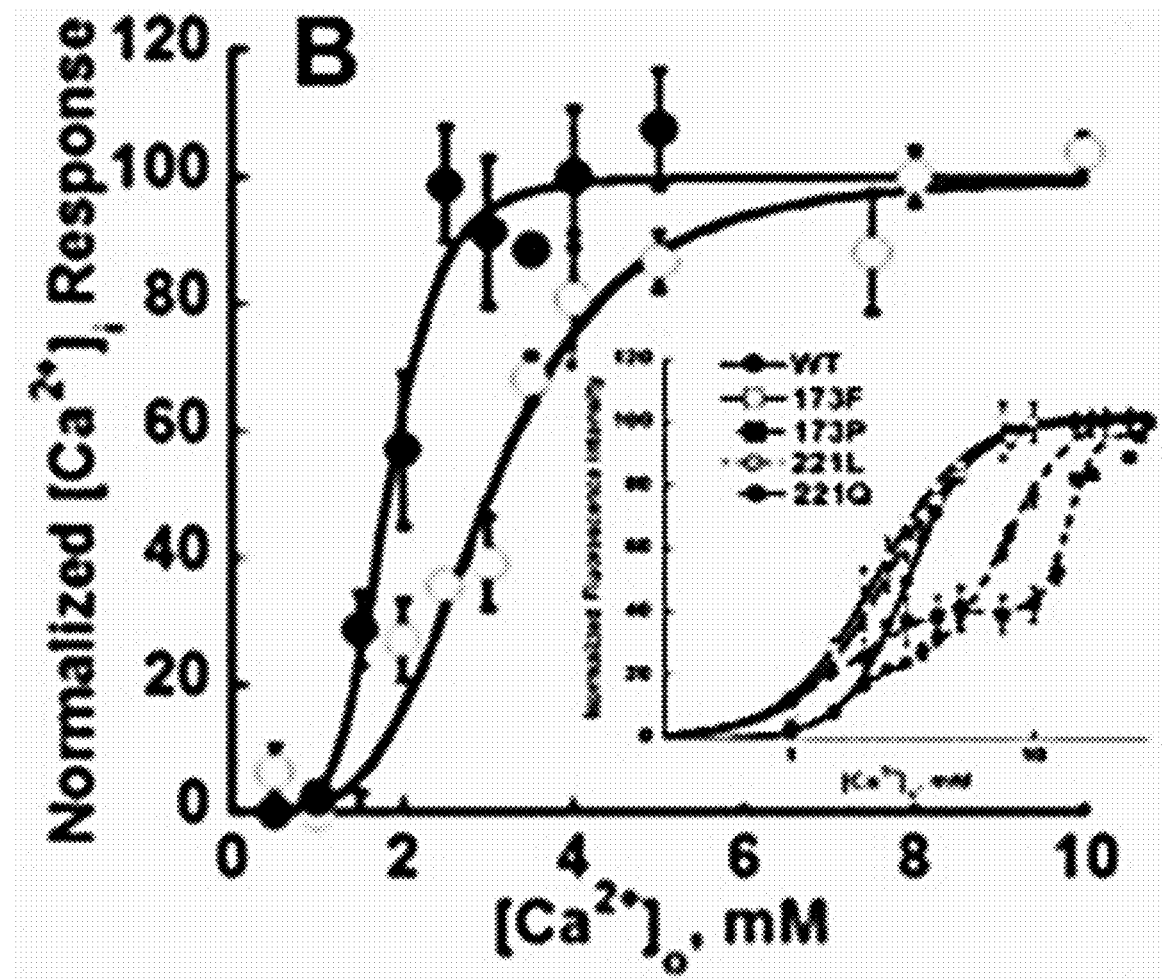

CaSR and other family C of GPCRs are able to trigger multiple intracellular signaling pathways includes Gq/11 signaling, Gi/o signaling, Gs signaling, extracellular signal-regulated kinases 1 and 2 (ERK1/2) signaling, and intracellular calcium ($[Ca^{2+}]i$) mobilization (FIGS. 26 and 27A-27B). Such capability to process a variety of extracellular signals and to relay this information to multiple intracellular signaling pathways is defined as functional selectivity or biased agonism (ligand biased signaling) [35]. However, the molecular basis for the functional cooperativity and selectivity conducted by CaSR and other family C GPCRs is largely unclear despite their critical roles in numerous (patho)physiological processes.

Figure 28A:
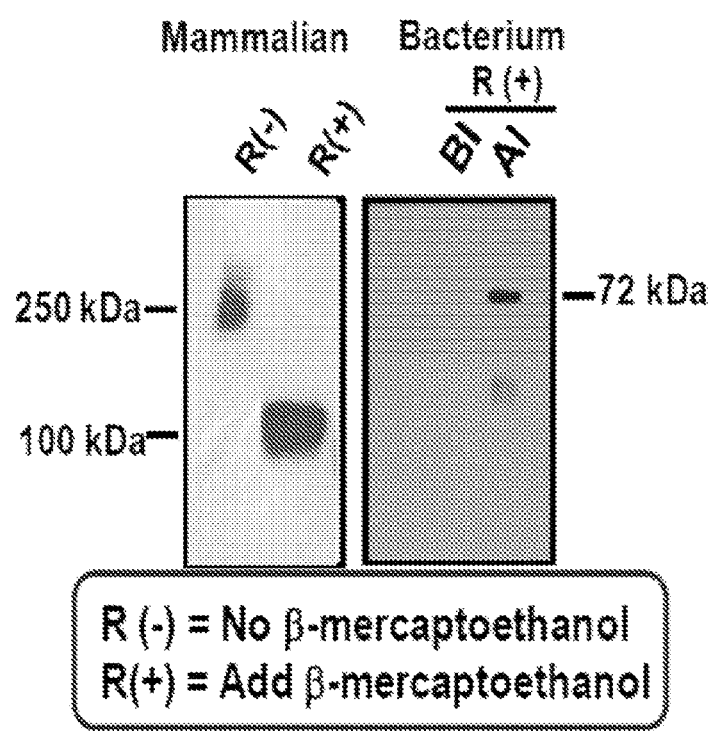
FIGS. 28A-28D show (FIG. 28A) SDS Page of mammalian and bacterial monomer) expressed ECD domain of CaSR (dimer). The expression and purification of the glycosylated extracellular domain of CaSR (ECD) (residues 20-612) using two mammalian expression systems that generate distinct glycosylated products, wild type 293-F cells or the HEK293S (GnTI-) cell line. The former wild type cell line generates recombinant products harboring heterogeneous complex-type N-glycans. In contrast, the second HEK293S (GnTI-) cell line lacks the enzyme Glc-NAc transferase I (GnTI), an enzyme required for the first step in the conversion of high mannose N-glycans into complex and hybrid structures. The HEK293S (GnTI-) cells are unable to synthesize complex and hybrid N-glycans and instead produce oligosaccharides containing a more homogeneous collection of structures based on Man5GlcNAc2-Asn. Both glycosylated forms of the CaSR ECD were purified as dimers (FIG. 28B) HSQC spectra of 15NPhe labeled by HER293 expression with chemical shift changes upon addition of $Ca^{2+}$. HEK293S (GnTI-) expression without complex glycosylation sharpens resonance (FIGS. 28C-28D). Deuterated 15N, 13C, labeled CaSR-ECD from *E. coli.* exhibited dispersion and $Ca^{2+}$ changes in chemical shifts.
Figure 28B:
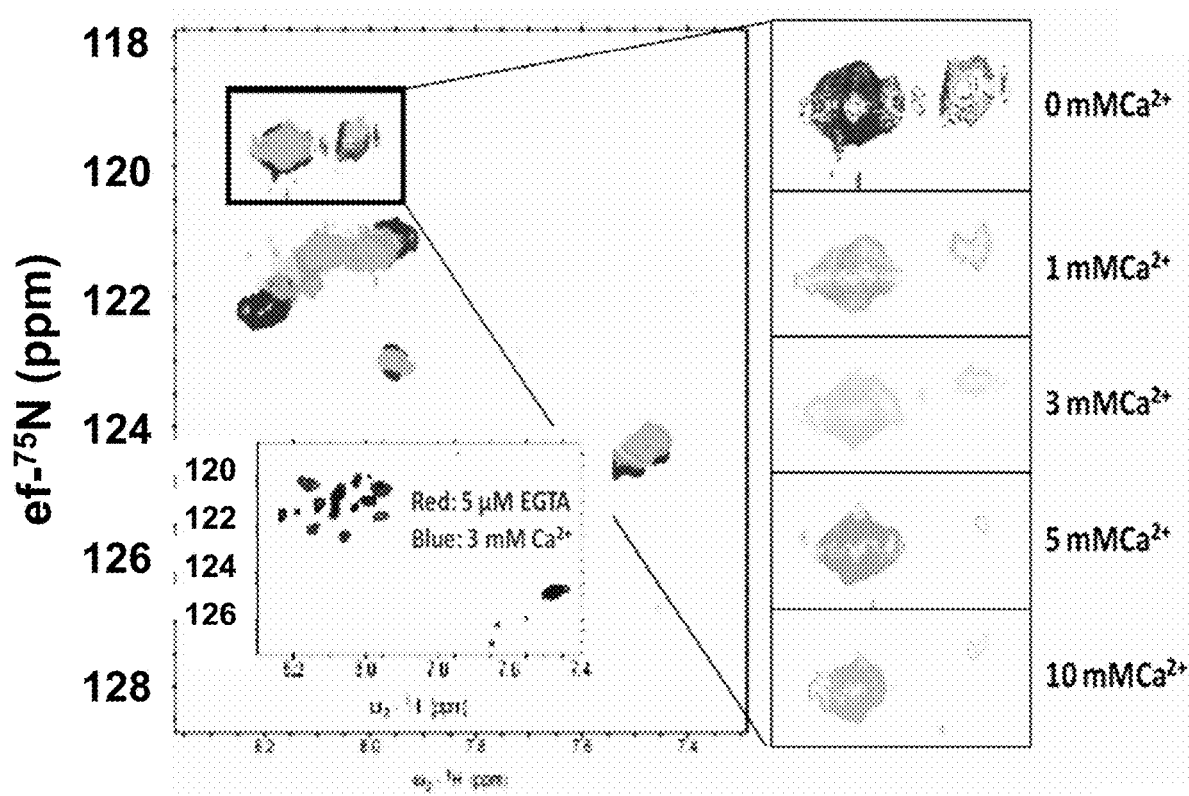
Figure 28C:
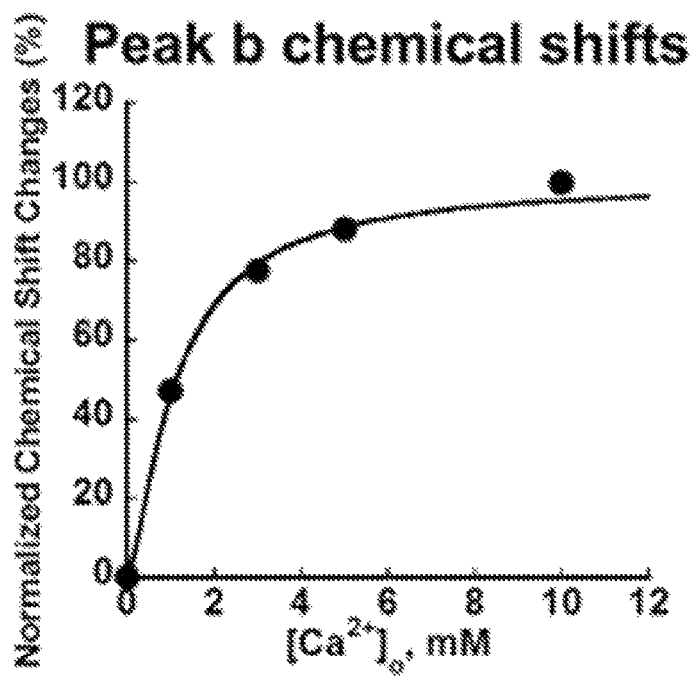
Figure 28D:
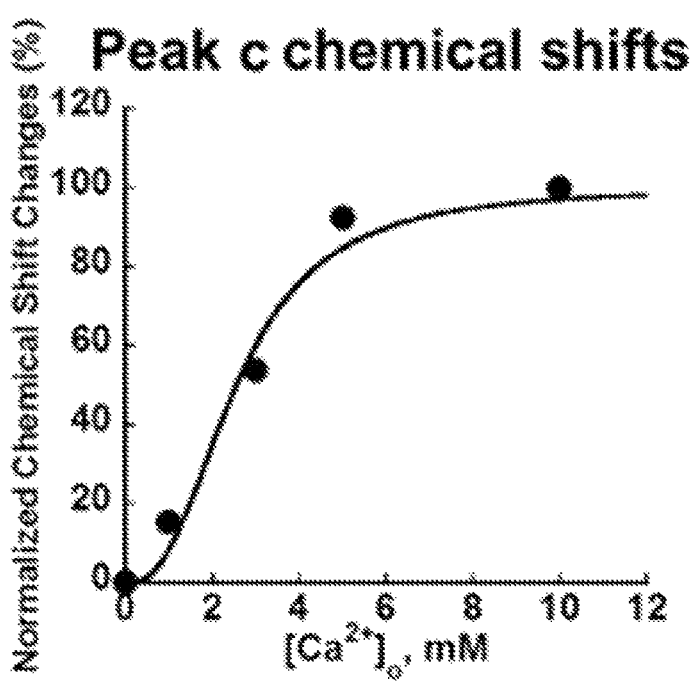

Nearly 200 mutations and polymorphisms have been found in the CaSR. FIGS. 28A-28C shows that inactivating and activating mutations are largely distributed around the hinge region and dimerization interface of our recently determined structure of the ECD. Inactivating CaSR mutations in patients with familial hypocalciuric hypercalcemia (FHH) and neonatal severe hyperparathyroidism (NSHPT) reduce the CaSR's sensitivity to $[Ca^{2+}]_o$, whereas activating mutations in patients with autosomal dominant hypocalcemia (ADH) lead to enhanced sensitivity toward $[Ca^{2+}]_o$ and $[Mg^{2+}]_o$ [36, 37]. It has been demonstrated that these disease associated mutations alter either the CaSR's responses to $[Ca^{2+}]_o$ and $[Mg^{2+}]_o$ (EC50), and/or change its homotropic cooperativity (FIGS. 26 and 27A-27B) [38]. Clearly, integration of Ca2+ signaling from changes in $[Ca^{2+}]_o$ to intracellular signaling networks is critically important for many (patho)physiological processes. Understanding key determinants for regulating extracellular signaling will provide important insights into the molecular basis of the clinical disorders associated with this receptor. Further, the CaSR is being reassessed as a potential target of aromatic L-amino acids under certain toxic metabolic conditions. The CaSR expressed in the CNS might be pathologically activated by the elevated levels of L-Phe in phenylketonuria or in hepatic encephalopathy [26]. Understanding the capacity of L-Phe to rescue disease-linked mutations suggests the possibility of rescuing such mutated receptors using calcimimetics as pharmacotherapy and of designing novel drugs with the capacity to tune functional cooperativity. Further, extracellular calcium potentiates the inhibitory effect of $Mg^{2+}$ on parathyroid function in dispersed bovine parathyroid cells [39]. Conversely, serum $Mg^{2+}$ concentration are also perturbed in clinical conditions affecting the CaSR [40]. More importantly, the functional activity of CaSR was recently reported to participate in determining the serum $Mg^{2+}$ and the clinical presentations in patients with autosomal dominant hypocalcemia [37].

To date, how extracellular $Ca^{2+}$, $Mg^{2+}$ and amino acids cooperatively modulate intracellular $Ca^{2+}$ signaling is a long-standing unanswered question. Unfortunately, there are no determined CaSR structures reported thus far despite of extensive effort since the receptor was first cloned 22 years ago. Like other cGPCRs, CaSR functions as a dimer [41-47] with a very long N-terminus that is predicted to be folded into a bilobed extracellular domain (ECD) [8, 10, 12, 48-52].

The ECD has been shown to play an important role in the cooperative responses of the receptor to changes of $[Ca^{2+}]_o$, amino acids, metabolites, and neurotransmitters [19, 46, 53-57]. Determination of the X-ray structure of the ECD of CaSR is largely hampered by difficulty in crystallization due to heterogeneous and extensive glycosylation (11 N-glycosylation sites) as well as challenges associated with membrane proteins [58]. Further, $Ca^{2+}$ and ligand-binding sites with weak binding affinities and rapid off rates are often not occupied in a determined X-ray structure. For example, no bound $Ca^{2+}$ has been observed in >30 x-ray structures of the ECD of mGluRs[44, 59, 60],[61], despite the clear modulatory effect of $[Ca^{2+}]_o$ on this receptor. Furthermore, additional challenges result from lack of direct binding assays for weak $Ca^{2+}$-binding and amino acid-binding (Kd about mM) based on the use of purified membrane proteins with native-like conformations [50, 62, 63]. The quantification of functional cooperativity with binding cooperativity and visualization of the molecular connectivity in tuning cooperativity are yet to be achieved.

Figures 29A, 29B:
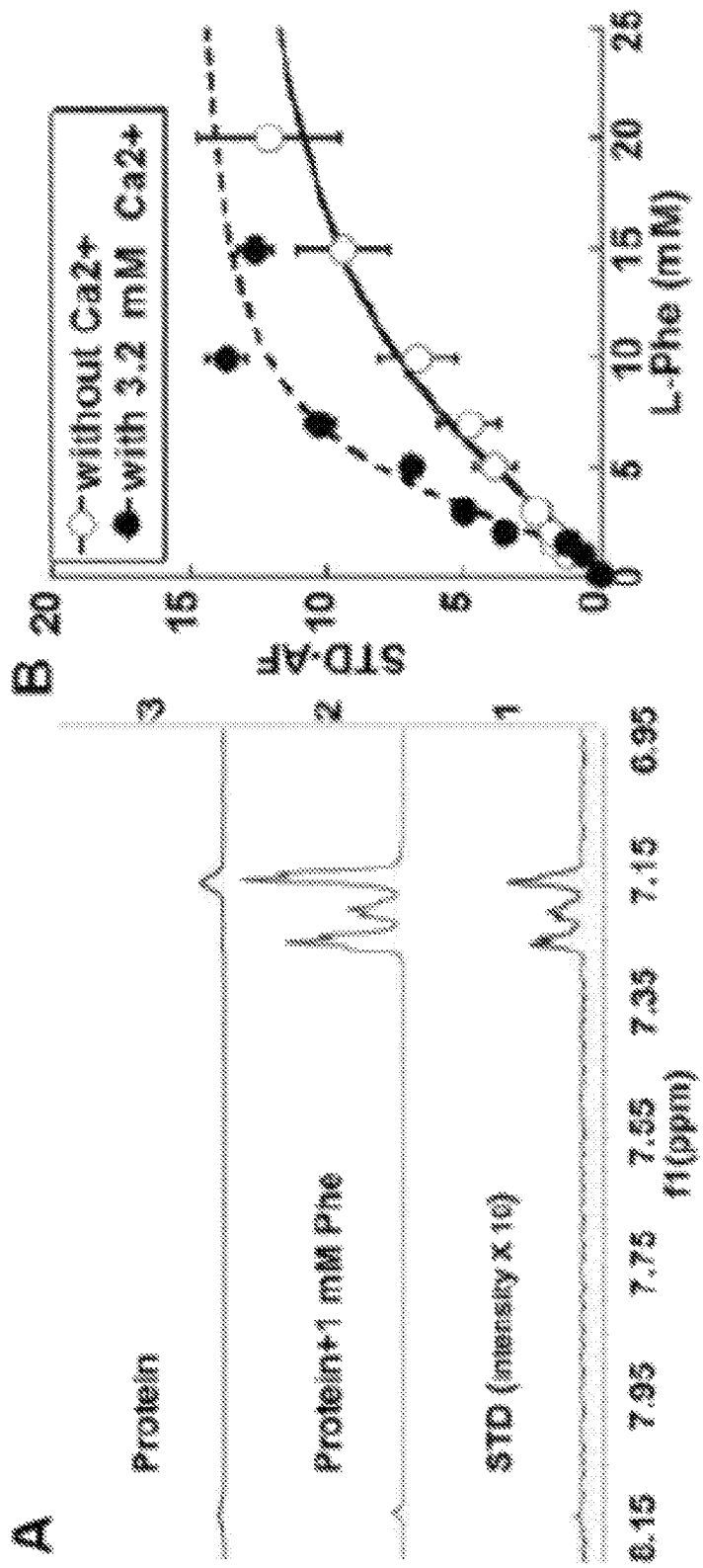
FIGS. 29A-29B show graphs demonstrating monitoring of the ligand-protein interaction via STD NMR. (29A)$^1$H NMR spectra of a solution of 20 μM CaSR ECD from HEK293S (GnTI-) cells without (blue line) or with (green line) 1 mM of L-Phe. The difference between spectra at on and off resonance (STD) was shown in red line. (29B) The average STD-AF from the integrated signal of three major peaks during L-Phe titration, plotted against increasing L-Phe concentration and further fitted using Hill equation with (closed circle) and without (open circle) $Ca^{2+}$. The ECD of CaSR binds to L-Phe, and its affinity is enhanced in the presence of calcium

Based on the determined X-ray structures of the ECD of mGluRs, activation of cGPCRs is currently viewed as involving an agonist-induced change of the conformational state of the GPCR from the inactive open (or open-open) (inactive) state to open-close and close-close states [44, 61, 64-66]. However, such a conversion from the inactive to the active forms cannot provide a direct answer to the basis for ligand-induced biased signaling pathways. It also cannot explain the effect of disease mutations at the ECD domain on functional selectivity even under the same cellular conditions (FIGS. 29A-29B). In contrast to this current view, we have shown that the ECD domain of CaSR exhibits a conformational ensemble of several key conformational states based on the newly determined crystal structure of the ECD of CaSR (FIGS. 30A-30B) and studies using site-directed mutagenesis, molecular dynamic (MD) simulations, and biochemical and functional studies [38]. Here we hypothesize that $Ca^{2+}$-binding at the predicted calcium-binding sites, especially at the hinge region of the ECD and the dimer interface, selectively and cooperatively stabilizes active conformation(s) tailored to the Gq/11 pathway. The binding of an amino acid such as Phe adjacent to the $Ca^{2+}$-binding site at the hinge region globally tailors the activity of the receptor with co-activation of ERK pathways. Disease-associated mutations around our predicted binding sites for extracellular $Ca^{2+}$ and amino acids at the ECD stabilize different conformational states via altering molecular connectivity. These effects, in turn, largely bias downstream signaling pathways (biased agonism)[38]. Our studies will represent a new paradigm for our understanding the molecular basis of functional selectivity especially for a cGPCR that is very different from reported effort currently mainly conducted for family A and B of GPCR with a focus on the transmembrane regions [67-69].

Cooperative binding of calcium and other agonists at the ECD domain of CaSR can stabilize required conformations that in turn tailor/bias intracellular signaling pathways required for physiological responses, and disease-associated mutations can lead to biased signaling by either altering the ECD structure or affecting the equilibrium among the different conformers. The data and studies in Example 2 can identify the key determinants that contribute to (1) cooperative $[Ca^{2+}]o$ activation orchestrated by multiple $Ca^{2+}$- and $Mg^{2+}$-binding sites and (2) interaction between ligands/drug and $Ca^{2+}$.

Determination of the Molecular Basis for Cooperative $[Ca^{2+}]_o$ Activation Orchestrated by Multiple $Ca^{2+}$ and $Mg^{2+}$-Binding Sites.

Cooperative binding of $Ca^{2+}$ at the multiple $Ca^{2+}$-binding sites stabilizes active dimer form that is critical for CaSR's response over a narrow physiological range of $[Ca^{2+}]_o$ independent of other agonists. Example 2 further examines (1) the X-structures of apo-, $Ca^{2+}$- and $Mg^{2+}$-loaded forms of the ECD and ECD-cysteine domains, (2) metal-induced conformational changes, (3) binding affinity for $Ca^{2+}$ and $Mg^{2+}$ and cooperativity using purified ECD and naturally occurring disease and engineered variants, and (4) examines CaSR-mediated functionally cooperativity in Gq/11 $Ca^{2+}$ signaling (i.e., $[Ca^2]i$, oscillations and ER $Ca^{2+}$ release).

CaSR has an estimated Hill coefficient of 3-4 for its regulation of biological processes such as activating intracellular $Ca^{2+}$ signaling, inhibiting PTH release in parathyroid cells and stimulating calcitonin secretion in C-cells (FIGS. 26 and 27A-27B)[25]. This functional positive homotropic cooperative response of CaSR to $[Ca^{2+}]_o$, is needed for the receptor's ability to respond over a narrow physiological range of $[Ca^{2+}]_o$ (1.1-1.3 mM)[24]. We have also shown that $Ca^{2+}_o$-evoked, CaSR-mediated $[Ca^{2+}]_i$ oscillations, IP production and ERK1/2 activities also exhibit cooperative changes in their responses to altering of $[Ca^{2+}]_o$ in CaSR-transfected HEK cells[214]. Disease-associated mutations around calcium-binding sites largely alter calcium cooperativity (FIGS. 26 and 27A-27B) [215]. $Mg^{2+}$ homeostasis shares common regulatory hormones including parathyroid hormone (PTH) and vitamin D to calcium homeostasis [216]. As another essential divalent cation, the level of extracellular $Mg^{2+}$ is maintained within a relatively narrow range of ~0.75-1.05 mmol/L. CaSR is highly expressed in kidney and regulates the urinary excretion of $Ca^{2+}$ and $Mg^{2+}$ [217]. Localized concentrations of $Mg^{2+}$ such as from the shark kidney can be as high as 40 mM [218, 219]. It has been demonstrated that extracellular $Mg^{2+}$ behaved as a partial agonist for CaSR supported by the relative higher $EC_{50}$ of 10 mM for $Mg^{2+}$ vs. 3 mM for $Ca^{2+}$ when the CaSR was expressed in *X. laevis* oocytes[10]. $Mg^{2+}$ also has an $EC_{50}$ that is about twice that of $Ca^{2+}$ to augment of production of IPs and arachidonic acid in studies using transient expression of rat CaSR in CHO cells. Consistently, CaSR transiently expressed in HEK cells has an EC50 for intracellular calcium responses of 15-20 and 3-5 mM for to $Mg^{2+}$ and $Ca^{2+}$ under physiological conditions, respectively (in the presence of 150 mM NaCl) [220, 221].

Despite the higher $EC_{50}$ of $Mg^{2+}$, small changes in extracellular calcium or $Mg^{2+}$ in the presence of elevated concentrations of the other divalent cation are able to trigger CaSR mediated intracellular calcium transients in mouse distal convoluted tubule cells (MDCT)[222]. However the role of $Mg^{2+}$ as a partial but physiologically important agonist is largely uninvestigated despite significant progress in the understanding in the structure and function of CaSR-mediated extracellular calcium signaling, including developing computational algorithms, site-directed mutagenesis studies, functional assays, and molecular dynamics (MD) stimulation [38, 59-60, 70, 215, and 223-227].

Figure 30A:
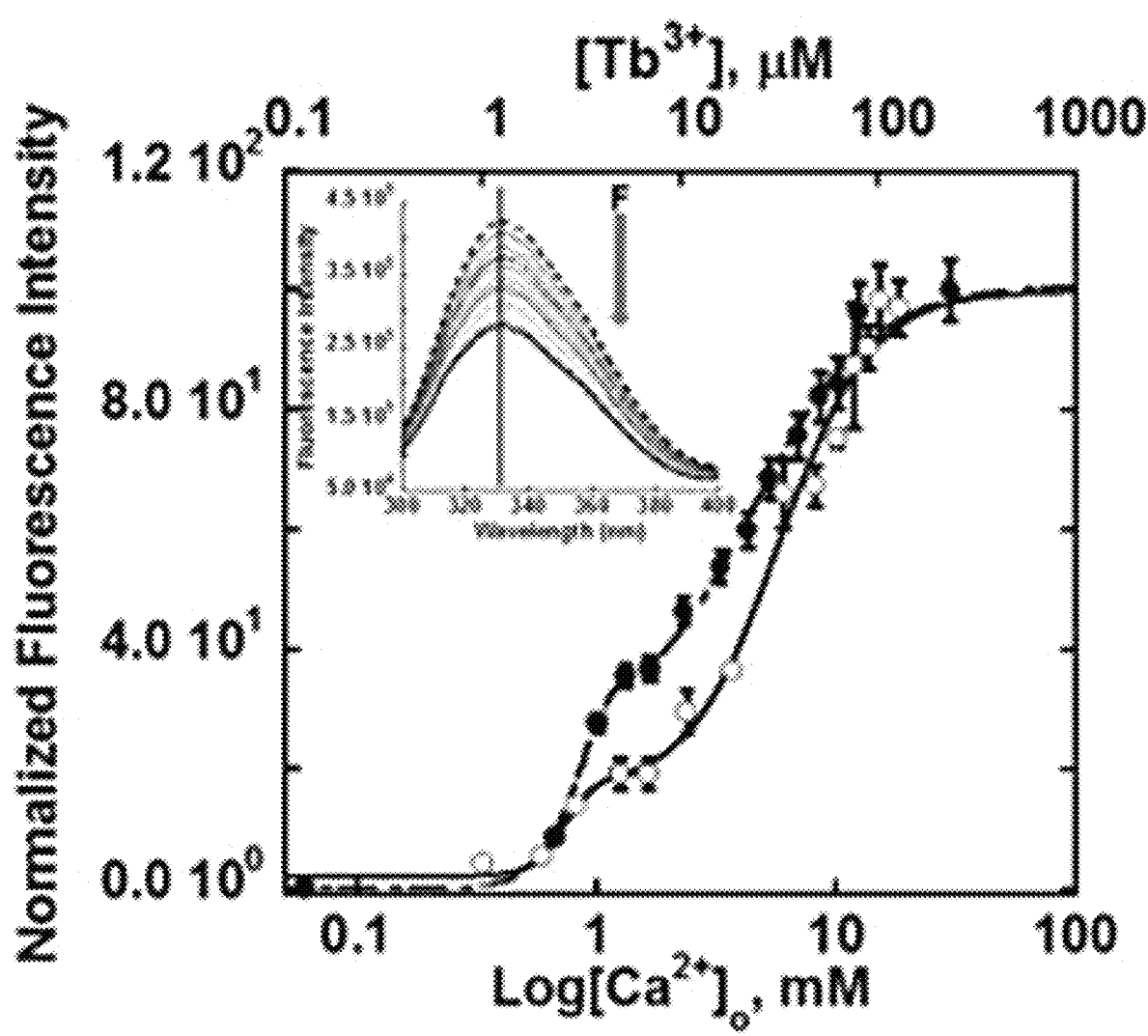
FIGS. 30A-30D show graphs demonstrating (FIG. 30A) The ECD exhibits two phase binding curves for Ca2+ (○) by Trp fluorescence signal change (insert) and for Tb3+ (●) monitored by LRET. Such a change can be fitted with 2-phase Hill equation with Hill numbers of 1.1 and 3.8 and Kd of 0.9 and 10 mM, respectively, for Ca2+ (FIG. 30B) Subdomain 1 of the ECD with 3 Ca2+-binding sites also exhibits 2-phase Tb3+ titration. Removal of Site 1 (Mut1), largely removes the initial strong binding phase (FIG. 30C). Ca2+ competes with Tb3+ for ECD binding by LRET.
Figure 30B:
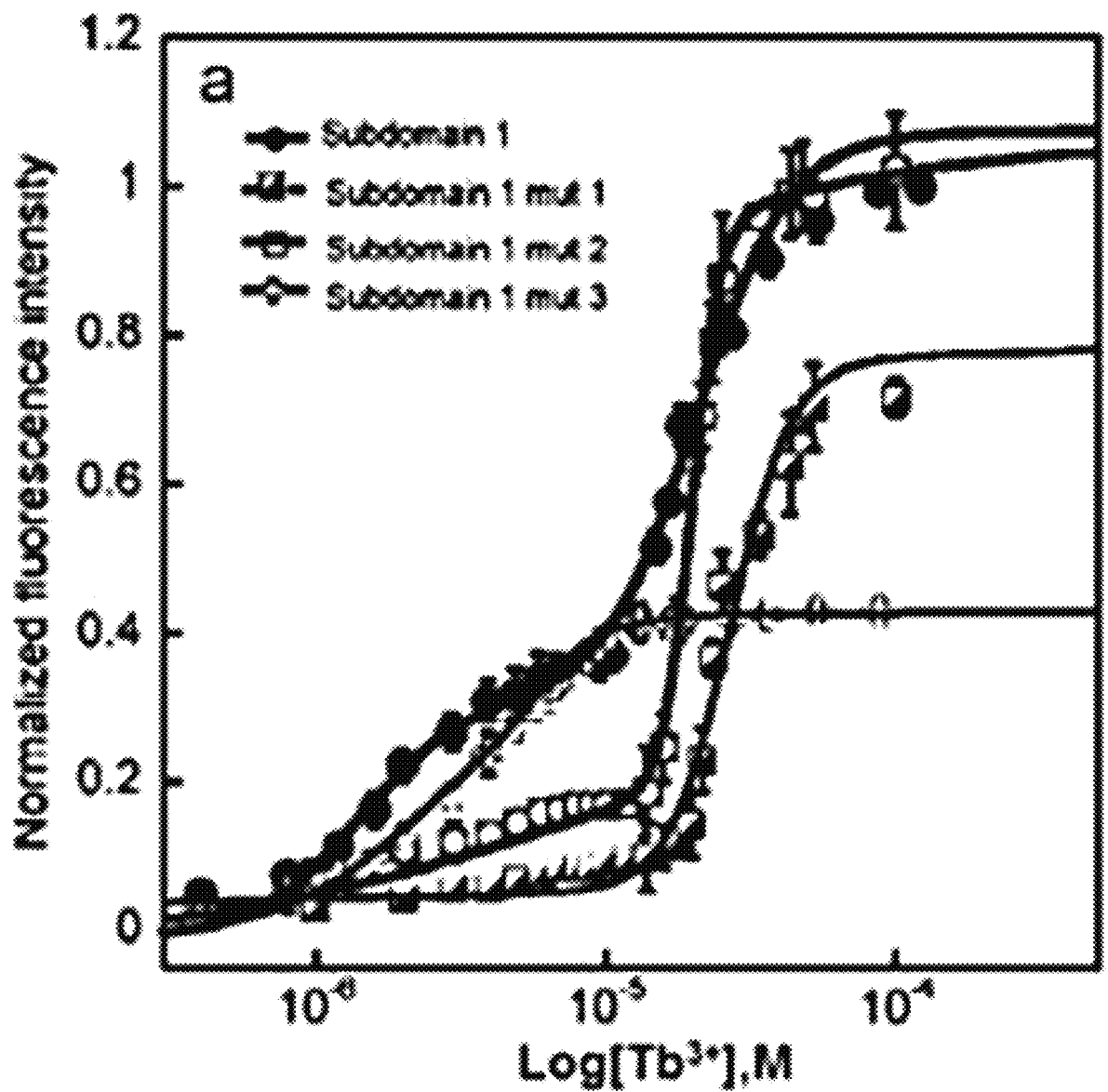
Figure 30C:
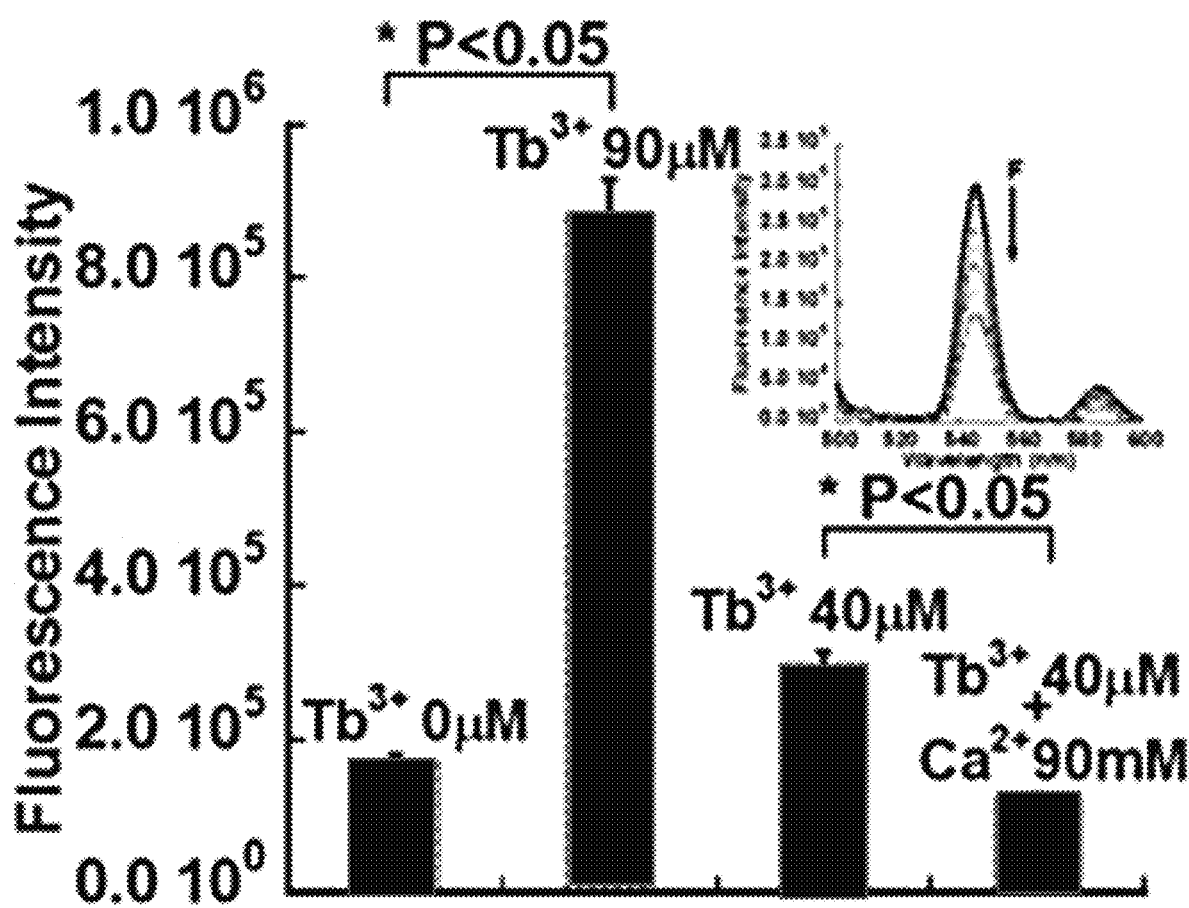
Figure 30D:
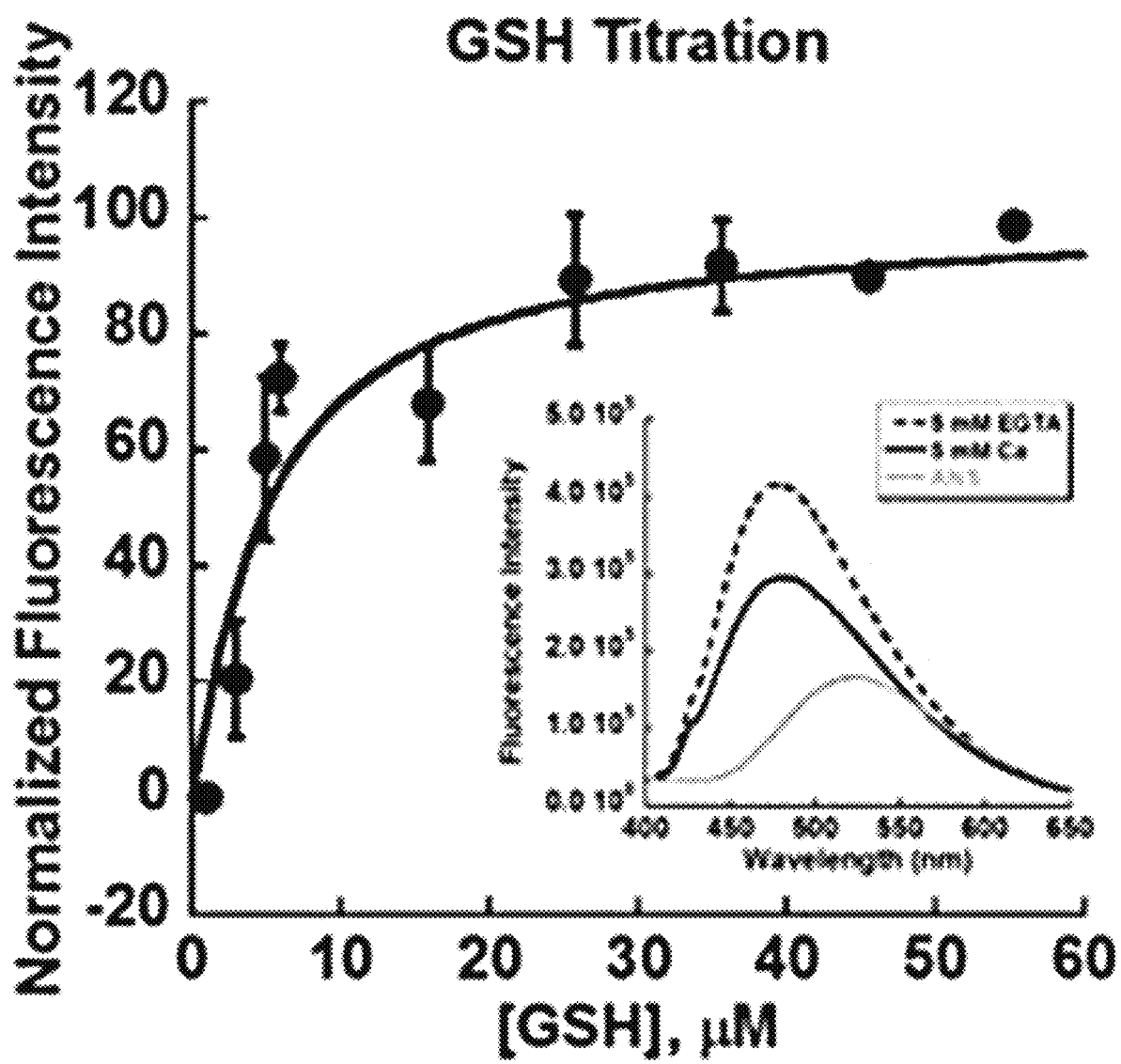
Figure 31A:
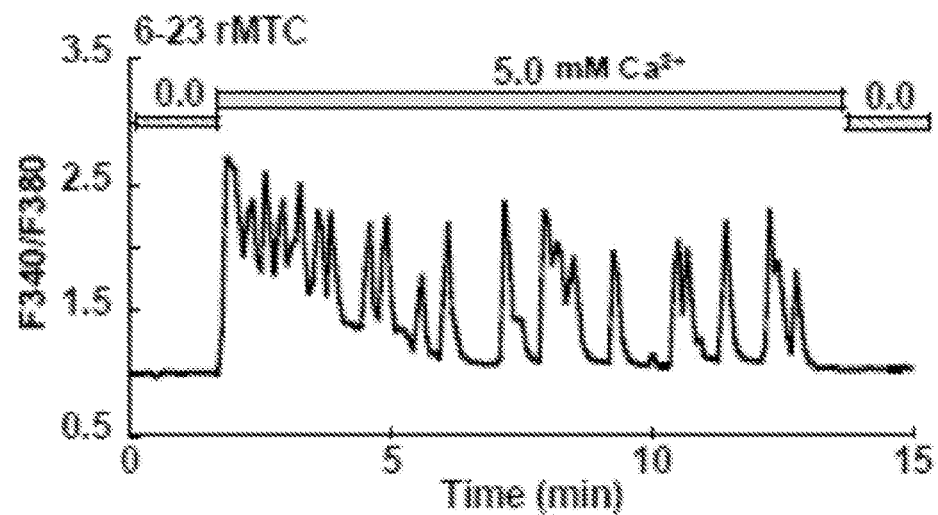
FIGS. 31A-31B show intracellular calcium responses monitored by Fura-2 in 6-23 MTC cells, which endogenously express the CaSR (FIG. 31A) and Mg2+ induced Intracellular calcium responses monitored by Fura-2 in CaSR transiently transfected HEK293 cells (FIG. 31B).
Figure 31B:
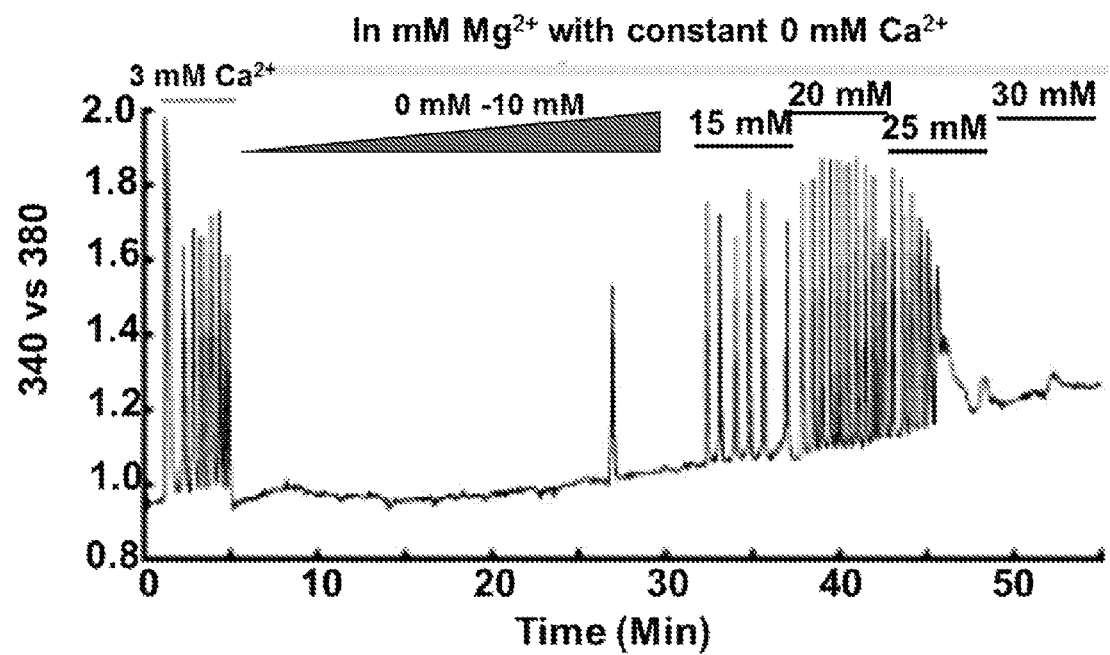
Figure 32A:
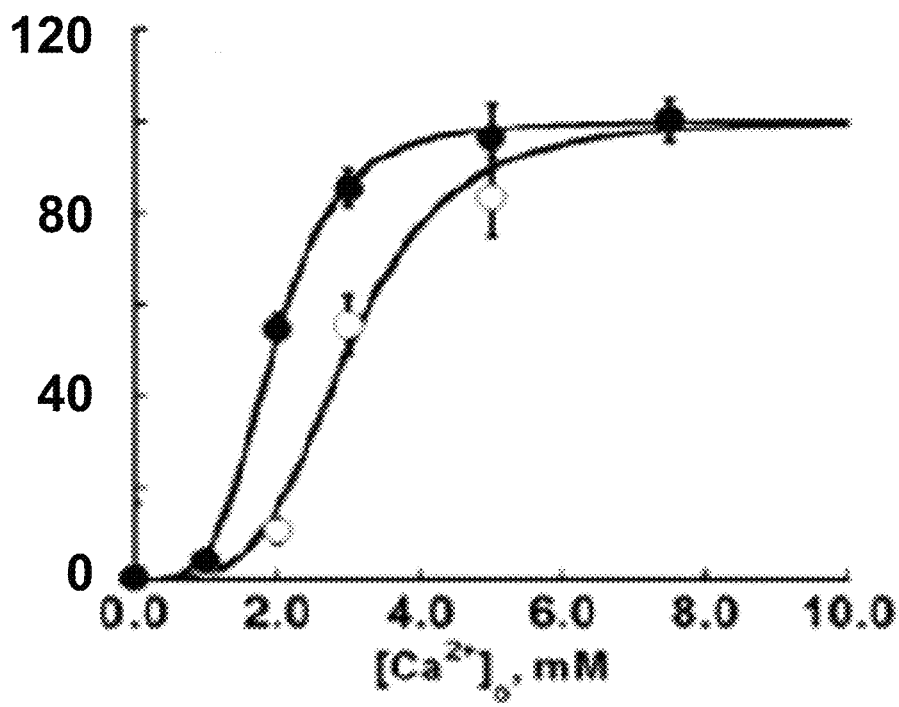
FIGS. 32A-32B show graphs demonstrating IP (FIG. 32A) and ERK (FIG. 32B) activities. Disease-associated CaSR mutations disrupt the homo-cooperativity of CaSR activity/L-Phe enhanced the $Ca^{2+}$-induced ERK activity in HEK-CaSR cells (insert).
Figure 32B:
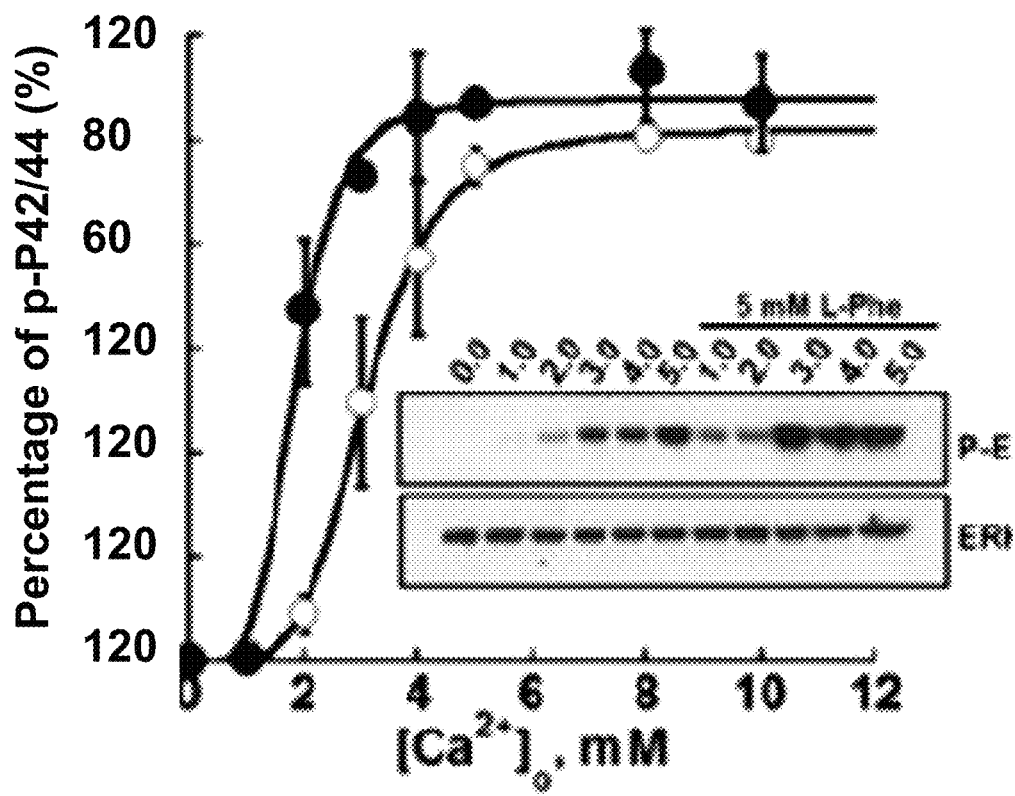

Two complementary approaches-monitoring $[Ca^{2+}]_i$ oscillations in living cells and performing molecular dynamics (MD) simulations—to provide important insights into how the CaSR functions and to understand the behavior of the receptor at the atomic level. By mutating the predicted residues that are involved in $Ca^{2+}$-binding, we reported that the predicted $Ca^{2+}$-binding site within the hinge region of the ECD of CaSR (denoted as Hinge site or Site 1) and its interaction with other $Ca^{2+}$-binding sites within the ECD is essential for tuning functional positive homotropic cooperativity caused by changes in $[Ca^{2+}]_o$. Our results, based on functional data suggest that cooperative binding of $Ca^{2+}$ at the CaSR's multiple $Ca^{2+}$-binding sites likely maximizes its responses over a narrow physiological range of $[Ca^{2+}]_o$ independent of amino acids or other agonists[45-47]. Our developed working model challenges current paradigms for GPCR signaling and provides the most comprehensive view currently available for the role of the CaSR's ECD in binding and functional cooperativity and in the molecular basis for diseases and biased signaling (FIGS. 30A-30B). By developing mammalian expression of a functional dimer with reduced glycosylation, the first determination of the structure of ECD of CaSR at 2.1 Å (FIGS. 30A-30B) has recently been made. The overall structure of ECD of CaSR is similar to the modeled structure and the structures of the EC domains of other cGPCR family members, such as mGluRs and GABA receptors, although the sequence homology among the members of the cGPCR family are generally quite low (20-30%) (FIG. 31).

Investigation of the Molecular Basis for Tuning CaSR Mediated Signal Pathways (Functional Selectivity).

CaSR is able to trigger multiple intracellular signaling pathways including Gq/11 signaling, Gi/o signaling, Gs signaling, extracellular signal-regulated kinases 1 and 2 (ERK1/2) signaling, and intracellular calcium ($[Ca^{2+}]_i$) mobilization. Using various assays, we have shown that disease mutations such as P172 near the $Ca^{2+}$-binding sites biases the signaling pathways from Gq/11 to ERK1/2 signaling (FIGS. 35A-35D). Clinically relevant mutations have been shown to impact regulation and signaling bias by positive (e.g. Cinacalet) and negative (e.g NPS-2143) allosteric modulators [272].

This Example further aims to (1) verify key residues contributing to the heterotropic cooperativity described above, and (2) probe the effects of ligand/agonist binding on the biased agonism to establish the correlation between the ECD and the modulation of downstream signaling pathways and the modulation of several signaling pathways. The effect of agonists ($[Ca]_o$, Phe), antagonists, and pharmochaperones of CaSR on $Ca^{2+}$ dynamics and intracellular signaling can be determined via the IP and ERK pathways in HEK 293 and 6-23 cells as well as calcitonin production in the latter. Mutations at the key residues involved in ligand-binding can be introduced to test the effects of these mutations on the synergistic effect using the established in vitro binding assays and cell-based functional assays previously described. In addition to calcium mobilization and ER calcium release via Gq/11, the total inositol phosphates [227], MAP kinase activities, cAMP activities can be determined using established methods [273]. To reduce error using gel western assay, we will using FRET solution assay reported by Brauner-Osborne. Similar assay will also be applied to cAMP activity via Gs pathway. Measurement of calcitonin (CT) release in 6-23 cells will be determined

[274]. The concentration of calcitonin secreted by the cells will be done using the rat calcitonin IRMA Kit (I mmutopics)[249].

References For Example 2

1. Reeves, P. J., et al., *Structure and function in rhodopsin: high-level expression of rhodopsin with restricted and homogeneous N-glycosylation by a tetracycline-inducible N-acetylglucosaminyltransferase I-negative HEK293S stable mammalian cell line.* Proc Natl Acad Sci USA, 2002. 99(21): p. 13419-24.

2. Jacobsen, S. E., et al., *Delineation of the GPRC6A receptor signaling pathways using a mammalian cell line stably expressing the receptor.* J Pharmacol Exp Ther, 2013. 347(2): p. 298-309.

3. Kenakin, T. and A. Christopoulos, *Measurements of ligand bias and functional affinity.* Nat Rev Drug Discov, 2013. 12(6): p. 483.

4. Makita, N. and T. Iiri, *Biased agonism: a novel paradigm in G protein-coupled receptor signaling observed in acquired hypocalciuric hypercalcemia.* Endocr J, 2014. 61(4): p. 303-9.

5. Kornfeld, R. and S. Kornfeld, *Assembly of asparagine-linked oligosaccharides.* Annu Rev Biochem, 1985. 54: p. 631-64.

6. Schachter, H., *Biosynthetic controls that determine the branching and microheterogeneity of protein-bound oligosaccharides.* Biochem Cell Biol, 1986. 64(3): p. 163-81.

7. Bouschet, T. and J. M. Henley, *Calcium as an extracellular signalling molecule: perspectives on the Calcium Sensing Receptor in the brain.* C R Biol, 2005. 328(8): p. 691-700.

8. Hofer, A. M. and E. M. Brown, *Extracellular calcium sensing and signalling.* Nat Rev Mol Cell Biol, 2003. 4(7): p. 530-8.

9. Robertson, M. A., et al., *Specific changes in the oligosaccharide moieties of VSV grown in different lectin-resistant CHO cells.* Cell, 1978. 13(3): p. 515-26.

10. Brown, E. M., et al., *Cloning and characterization of an extracellular Ca(2+)-sensing receptor from bovine parathyroid.* Nature, 1993. 366(6455): p. 575-80.

11. Mathias, R. S., et al., *Identification of the calcium-sensing receptor in the developing tooth organ.* J Bone Miner Res, 2001. 16(12): p. 2238-44.

12. Hinson, T. K., et al., *Identification of putative transmembrane receptor sequences homologous to the calcium-sensing G-protein-coupled receptor.* Genomics, 1997. 45(2): p. 279-89.

13. Cheng, I., et al., *Identification and localization of the extracellular calcium-sensing receptor in human breast.* J Clin Endocrinol Metab, 1998. 83(2): p. 703-7.

14. Cima, R. R., et al., *Identification and functional assay of an extracellular calcium-sensing receptor in Necturus gastric mucosa.* Am J Physiol, 1997. 273(5 Pt 1): p. G1051-60.

15. Buchan, A. M., et al., *Mechanism of action of the calcium-sensing receptor in human antral gastrin cells.* Gastroenterology, 2001. 120(5): p. 1128-39.

16. Lundgren, S., et al., *A protein involved in calcium sensing of the human parathyroid and placental cytotrophoblast cells belongs to the LDL-receptor protein superfamily.* Exp Cell Res, 1994. 212(2): p. 344-50.

17. Chattopadhyay, N., et al., *Extracellular calcium-sensing receptor induces cellular proliferation and activation of a nonselective cation channel in 0373 human astrocytoma cells.* Brain Res, 1999. 851(1-2): p. 116-24.

18. Brown, E. M. and R. J. MacLeod, *Extracellular calcium sensing and extracellular calcium signaling.* Physiol Rev, 2001. 81(1): p. 239-297.

19. Chang, W. and D. Shoback, *Extracellular Ca2+-sensing receptors—an overview.* Cell Calcium, 2004. 35(3): p. 183-96.

20. Hebert, S. C., *Extracellular calcium-sensing receptor: implications for calcium and magnesium handling in the kidney.* Kidney Int, 1996. 50(6): p. 2129-39.

21. Hofer, A. M., et al., *The extracellular calcium-sensing receptor and cell-cell signaling in epithelia.* Cell Calcium, 2004. 35(3): p. 297-306.

22. Fudge, N. J. and C. S. Kovacs, *Physiological studies in heterozygous calcium sensing receptor (CaSR) gene-ablated mice confirm that the CaSR regulates calcitonin release in vivo.* BMC Physiol, 2004. 4(1): p. 5.

23. Kovacs, C. S., et al., *Regulation of murine fetal-placental calcium metabolism by the calcium-sensing receptor.* J Clin Invest, 1998. 101(12): p. 2812-20.

24. Breitwieser, G. E., *Calcium sensing receptors and calcium oscillations: calcium as a first messenger.* Curr Top Dev Biol, 2006. 73: p. 85-114.

25. Walter, S., et al., *Pharmacology of AMG 416 (Velcalcetide), a novel peptide agonist of the calcium-sensing receptor, for the treatment of secondary hyperparathyroidism in hemodialysis patients.* J Pharmacol Exp Ther, 2013. 346(2): p. 229-40.

26. Conigrave, A. D., S. J. Quinn, and E. M. Brown, *L-amino acid sensing by the extracellular Ca2+-sensing receptor.* Proc Natl Acad Sci USA, 2000. 97(9): p. 4814-9.

27. Wang, M., et al., *Activation of family C G-protein-coupled receptors by the tripeptide glutathione.* J Biol Chem, 2006. 281(13): p. 8864-70.

28. Francesconi, A. and R. M. Duvoisin, *Divalent cations modulate the activity of metabotropic glutamate receptors.* J Neurosci Res, 2004. 75(4): p. 472-9.

29. Vetter, T. and M. J. Lohse, *Magnesium and the parathyroid.* Curr Opin Nephrol Hypertens, 2002. 11(4): p. 403-10.

30. Galvez, T., et al., *Ca(2+) requirement for high-affinity gamma-aminobutyric acid (GABA) binding at GABA(B) receptors: involvement of serine 269 of the GABA(B)R1 subunit.* Mol Pharmacol, 2000. 57(3): p. 419-26.

31. Wise, A., et al., *Calcium sensing properties of the GABA(B) receptor.* Neuropharmacology, 1999. 38(11): p. 1647-56.

32. Gether, U., *Uncovering molecular mechanisms involved in activation of G protein-coupled receptors.* Endocr Rev, 2000. 21(1): p. 90-113.

33. Oldham, W. M. and H. E. Hamm, Heterotrimeric G protein activation by G-protein-coupled receptors. Nat Rev Mol Cell Biol, 2008. 9(1): p. 60-71.

34. Rosenbaum, D. M., S. G. Rasmussen, and B. K. Kobilka, *The structure and function of G-protein-coupled receptors.* Nature, 2009. 459(7245): p. 356-63.

35. Zhou, L. and L. M. Bohn, *Functional selectivity of GPCR signaling in animals.* Curr Opin Cell Biol, 2014. 27: p. 102-8.

36. Thakker, R. V., *Diseases associated with the extracellular calcium-sensing receptor.* Cell Calcium, 2004. 35(3): p. 275-82.

37. Kinoshita, Y., et al., *Functional activities of mutant calcium-sensing receptors determine clinical presentations in patients with autosomal dominant hypocalcemia.* J Clin Endocrinol Metab, 2014. 99(2): p. E363-8.

38. Zhang, C. M., N.; Hannan, F.; Nesbit, M; Thakker, R; Hamelberg, D.; Brown, E.; Yang, J., *Role of Ca2+ and L-Phe* in Regulating Functional Cooperativity of Disease-Associated "Toggle" Calcium-Sensing Receptor Mutations. PLoS One, 2014.

39. Brown, E. M., et al., Extracellular calcium potentiates the inhibitory effects of magnesium on parathyroid function in dispersed bovine parathyroid cells. Metabolism, 1984. 33(2): p. 171-6.

40. Ruat, M., et al., Cloned and expressed rat Ca2+-sensing receptor. J Biol Chem, 1996. 271(11): p. 5972-5.

41. Bai, M., et al., Intermolecular interactions between dimeric calcium-sensing receptor monomers are important for its normal function. Proc Natl Acad Sci USA, 1999. 96(6): p. 2834-9.

42. Pace, A. J., L. Gama, and G. E. Breitwieser, Dimerization of the calcium-sensing receptor occurs within the extracellular domain and is eliminated by Cys→Ser mutations at Cys101 and Cys236. J Biol Chem, 1999. 274(17): p. 11629-34.

43. Suzuki, Y., et al., Negative cooperativity of glutamate binding in the dimeric metabotropic glutamate receptor subtype 1. J Biol Chem, 2004. 279(34): p. 35526-34.

44. Kunishima, N., et al., Structural basis of glutamate recognition by a dimeric metabotropic glutamate receptor. Nature, 2000. 407(6807): p. 971-7.

45. Bai, M., S. Trivedi, and E. M. Brown, Dimerization of the extracellular calcium-sensing receptor (CaR) on the cell surface of CaR-transfected HEK293 cells. J Biol Chem, 1998. 273(36): p. 23605-10.

46. Bai, M., Structure-function relationship of the extracellular calcium-sensing receptor. Cell Calcium, 2004. 35(3): p. 197-207.

47. Zhang, Z., et al., The extracellular calcium-sensing receptor dimerizes through multiple types of intermolecular interactions. J Biol Chem, 2001. 276(7): p. 5316-22.

48. Jingami, H., S. Nakanishi, and K. Morikawa, Structure of the metabotropic glutamate receptor. Curr Opin Neurobiol, 2003. 13(3): p. 271-8.

49. Quinn, S. J., M. Bai, and E. M. Brown, pH Sensing by the calcium-sensing receptor. J Biol Chem, 2004. 279(36): p. 37241-9.

50. Hu, J. and A. M. Spiegel, Naturally occurring mutations of the extracellular Ca2+-sensing receptor: implications for its structure and function. Trends Endocrinol Metab, 2003. 14(6): p. 282-8.

51. Pearce, S. H., et al., Functional characterization of calcium-sensing receptor mutations expressed in human embryonic kidney cells. J Clin Invest, 1996. 98(8): p. 1860-6.

52. Hebert, S. C. and E. M. Brown, The extracellular calcium receptor. Curr Opin Cell Biol, 1995. 7(4): p. 484-92.

53. Bai, M., Structure and function of the extracellular calcium-sensing receptor (Review). Int J Mol Med, 1999. 4(2): p. 115-25.

54. Zhang, Z., et al., Three adjacent serines in the extracellular domains of the CaR are required for L-amino acid-mediated potentiation of receptor function. J Biol Chem, 2002. 277(37): p. 33727-35.

55. Mun, H. C., et al., The extracellular Ca2+-sensing receptor's venus fly trap domain is required for L-amino acid sensing. J Biol Chem, 2004.

56. Conigrave, A. D., et al., L-amino acid sensing by the calcium-sensing receptor: a general mechanism for coupling protein and calcium metabolism? Eur J Clin Nutr, 2002. 56(11): p. 1072-80.

57. Conigrave, A. D. and H. C. Lok, Activation of renal calcium and water excretion by novel physiological and pharmacological activators of the calcium-sensing receptor. Clin Exp Pharmacol Physiol, 2004. 31(5-6): p. 368-71.

58. Yang, W., et al., The effects of ca(2+) binding on the dynamic properties of a designed ca(2+)-binding protein(,). Biochemistry, 2005. 44(23): p. 8267-73.

59. Jiang, Y., et al., Elucidation of a novel extracellular calcium-binding site on metabotropic glutamate receptor 1{alpha} (mGluR1{alpha}) that controls receptor activation. J Biol Chem, 2010. 285(43): p. 33463-74.

60. Zhang, C., et al., Identification of an L-phenylalanine binding site enhancing the cooperative responses of the calcium-sensing receptor to calcium. J Biol Chem, 2014. 289(8): p. 5296-309.

61. Tsuchiya, D., et al., Structural views of the ligand-binding cores of a metabotropic glutamate receptor complexed with an antagonist and both glutamate and Gd3+. Proc Natl Acad Sci USA, 2002. 99(5): p. 2660-5.

62. Nagar, B., et al., Structural basis of calcium-induced E-cadherin rigidification and dimerization. Nature, 1996. 380(6572): p. 360-4.

63. Magno, A. L., B. K. Ward, and T. Ratajczak, The calcium-sensing receptor: a molecular perspective. Endocr Rev, 2011. 32(1): p. 3-30.

64. Venkatakrishnan, A. J., et al., Molecular signatures of G-protein-coupled receptors. Nature, 2013. 494(7436): p. 185-94.

65. Dore, A. S., et al., Structure of class C GPCR metabotropic glutamate receptor 5 transmembrane domain. Nature, 2014. 511(7511): p. 557-62.

66. Wu, H., et al., Structure of a class C GPCR metabotropic glutamate receptor 1 bound to an allosteric modulator. Science, 2014. 344(6179): p. 58-64.

67. Flock, T., et al., Universal allosteric mechanism for Galpha activation by GPCRs. Nature, 2015. 524(7564): p. 173-9.

68. Shukla, A. K., G. Singh, and E. Ghosh, Emerging structural insights into biased GPCR signaling. Trends Biochem Sci, 2014. 39(12): p. 594-602.

69. Davey, A. E., et al., Positive and negative allosteric modulators promote biased signaling at the calcium-sensing receptor. Endocrinology, 2012. 153(3): p. 1232-41.

70. Zhang, C., et al., Direct determination of multiple ligand interactions with the extracellular domain of the calcium-sensing receptor. J Biol Chem, 2014. 289(48): p. 33529-42.

71. Tang, S., et al., Design and application of a class of sensors to monitor Ca2+ dynamics in high Ca2+ concentration cellular compartments. Proc Natl Acad Sci USA, 2011. 108(39): p. 16265-70.

72. Doshi, U. H., D, Improved Statistical Sampling and Accuracy with Accelerated Molecular Dynamics on Rotatable Torsions. J. Chem. Theory Comput., 2012. 8(11): p. 4004-4012.

73. Doshi, U. H., D., Achieving Rigorous Accelerated Conformational Sampling in Explicit Solvent. Journal of Physical Chemistry Letters, 2014. 5: p. 1217-1224.

74. Kirberger, M., et al., Integration of Diverse Research Methods to Analyze and Engineer Ca-Binding Proteins: From Prediction to Production. Curr Bioinform, 2010. 5(1): p. 68-80.

75. Wang, X., et al., Towards predicting Ca2+-binding sites with different coordination numbers in proteins with atomic resolution. Proteins, 2009. 75(4): p. 787-98.

76. A, E., W. S S, and H. G N., A novel mutation in the calcium-sensing receptor (CASR) gene in a hypocalcemic

*patient presenting with symptoms of lupus*. CDA/CSEM Professional Conference and Annual Meetings Oct. 18-21, 2006 Abstract.

77. A, K., et al., *Parathyroid hormone therapy is an effective treatment in autosomal dominant hypocalcemia caused by activating mutations of calcium-sensing receptor*. Fifht International Conference on Children?s Bone Health 2009 Abstract PT-37.

78. A, K., et al., *An idiopathic epilepsy syndrome linked to 3q13.3-q21 and missense mutations in the extracellular calcium sensing receptor gene*. Annals of Neurology 2008 64: 158-167.

79. A, L., et al., *New type of calcium-sensing receptor mutation leading to isolated hypoparathyroidism*. Prog & Abstr Endo Soc 83rd Ann Meet 2001 P1-504.

80. A, L., et al., *New mutation of the calcium-sensing receptor gene associated with isolated hypoparathyroidism*. Prog & Abs 83rd Ann Meet Endo Soc 2001 P3-123.

81. A, L., et al., *Activating mutations of the calcium-sensing receptor: management of hypocalcemia*. Journal of Clinical Endocrinology and Metabolism 2001 86: 5313-5323.

82. A, L., et al., *A large homozygous or heterozygous in-frame deletion within the calcium-sensing receptor?s carboxylterminal cytoplasmic tail that causes autosomal dominant hypocalcemia*. Journal of Clinical Endocrinology and Metabolism 2000 85: 1695-1702.

83. A, U.-K., et al., *A novel mutation (E767K) in the second extracellular loop of the calcium-sensing receptor in a family with autosomal dominant hypocalcemia*. American Journal of Medical Genetics 2005 132A: 125-129.

84. AO, H., et al., *Calcium-induced activation of a mutant G-protein-coupled receptor causes in vitro transformation of NIH/3T3 cells*. Neoplasia 1999 1: 485-491.

85. B, F.-S., et al., *Correction of hypercalcemia by cinacalcet in familial hypocalciuric hypercalcemia*. Clinical Endocrinology 2007 68: 321-325.

86. B, H., et al., *Functional characterization of calcium sensing receptor polymorphisms and absence of association with indices of calcium homeostasis and bone mineral density*. Clinical Endocrinology 2006 5: 598-605.

87. B, O., et al., *Unusually severe phenotype of neonatal primary hyperparathyroidism due to a heterozygous inactivating mutation in the CASR gene*. European Journal of Pediatrics 2008 5: 569-73.

88. BK, W., et al., *Novel mutations in the calcium-sensing receptor gene associated with biochemical and function differences in familial hypocalciuric hypercalcemia*. Clinical Endocrinology 2006 64: 580-587.

89. BK, W., et al., *Functional deletion of the calcium-sensing receptor in a case of neonatal severe hyperparathyroidism*. Journal of Clinical Endocrinology and Metabolism 2004 89: 3721-3730.

90. BK, W., et al., *A novel mutation (L174R) in the Ca2+-sensing receptor sensing receptor gene associated with familial hypocalciuric hypercalcemia*. Human Mutation 1997 10: 233-235.

91. BK, W., et al., *A novel homozygous deletion in the calcium-sensing receptor ligand-binding domain associated with neonatal severe hyperparathyroidism*. Journal of Pediatric Endocrinology and Metabolism 2006 19: 93-100.

92. C, H., et al., *Novel mutations of the calcium-sensing receptor in familial hypocalciuric hypercalcemia and autosomal dominant hypocalcemia*. Prog & Abs 87th Ann Meet Endo Soc 2005 P2-407.

93. C, L., et al., *Identification of a novel inactivating R465Q mutation of the calcium-sensing receptor*. Biochemical and Biophysical Research Communications 2006 342: 996-1002.

94. C, M., et al., *Familial hypocalciuric hypercalcemia in a woman with metastatic breast cancer: A case report of mistaken identity*. Journal of Clinical Endocrinology and Metabolism 2003 88: 5132-5136.

95. C, S., et al., *Delineating a Ca2+ binding pocket within the Venus Flytrap Module of the human calcium-sensing receptor*. The Journal of Biological Chemistry 2005 280: 37917-37923.

96. C, V., et al., *A new missense mutation in the calcium-sensing receptor in familial benign hypercalcemia associated with lipoatrophy and insulin resistant diabetes*. Clinical Endocrinology 2000 53: 393-398.

97. CP, B., et al., *A family with autosomal dominant hypocalcaemia with hypercalciuria (ADHH): mutational analysis, phenotypic variability and treatment challenges*. Journal of Pediatric Endocrinology and Metabolism 2005 18: 689-699.

98. C-W, L., et al., *Novel missense mutation in the CASR gene in a Chinese family with familial hypocalciuric hypercalcemia*. Clinica Chimica Acta 2005 360: 167-172.

99. D, A.-H., et al., *A novel mutation in the calcium-sensing receptor responsible for autosomal dominant hypocalcemia in a family with uncommon parathyroid hormone polymorphisms*. Journal of Molecular Endocrinology 2003 31: 255-262.

100. D, D., et al., *Normalization of serum calcium, phosphorus, and magnesium with homeopathic PTH in a child with hypocalcemic hypercalciuria (HCHC) and a mutation of the calcium-sensing receptor gene*. Prog Abs 83rd Ann Mtg Endo Soc 2001 Abs P3-125.

101. D, I., et al., *Successful treatment of hypoparathyroidism caused by a novel calcium-sensing receptor mutation with thiazide diuretics and low dose alfacalcidol*. Bone 1998 23S: S382.

102. DR, C., et al., *Hypocalcemia and a novel calcium-sensing receptor activating mutation*. Ann Sci Meet Royal Australasian College Physicians Int Med J 2005 (Suppl.); 35: A68.

103. E, L., et al., *Two novel mutations of the calcium sensing receptor gene*. Prog & Abs Endo Soc 90th Ann Meet 2008 P1-568.

104. EA, W., et al., *Did cinacalcet help in the management of neonatal severe hyperparathyroidism secondary to a novel homozygous inactivating mutation of the calcium-sensing receptor?* Fifth International Conference on Children's Bone Health 2009 Abstract PT-35.

105. EE, M., et al., *A Ca(2+)-sensing receptor mutation causes hypoparathyroidism by increasing receptor sensitivity to Ca2+ and maximal signal transduction*. Pediatric Research 1997 42: 443-447.

106. EE, M., et al., *Novel mutations in the calcium-sensing receptor gene in tropical chronic pancreatitis in India*. Scandinavian Journal of Gastroenterology 2008 43: 117-121.

107. F, C., et al., *No evidence for mutations in the calcium-sensing receptor gene in sporadic parathyroid adenomas*. Journal of Bone and Mineral Research 1999 14: 878-882.

108. F, C., et al., *Genetic analyses in familial isolated hyperparathyroidism: implication for clinical assessment and surgical management*. Clinical Endocrinology 2006 64: 146-152.

109. F, C., et al., *Two Italian kindreds with familial hypocalciuric hypercalcemia caused by loss-of-function mutations in the calcium-sensing receptor (CaR) gene: functional characterization of a novel CaR missense mutation*. Clinical Endocrinology 2003 58: 199-206. Erratum. 2003 Clin Endocrinol 58: 671.

110. F, C., et al., *Identification and functional characterization of loss-of-function mutations of the calcium-sensing receptor in four Italian kindreds with familial hypocalciuric hypercalcemia*. European Journal of Endocrinology 2009 3: 481-9.

111. F, D., et al., *Severe neonatal hyperparathyroidism due to a large homozygous deletion of the calcium-sensing receptor gene requiring peritoneal dialysis before surgical care*. Prog Abs 87th Ann Mtg Endo Soc 2005 Abs P2-607.

112. F, D.-F., et al., *Neonatal severe hyperparathyroidism due to a heterozygous mutation of the calcium sensing receptor gene: evolution with conservative medical treatment*. Endocrine Society Congress 2009 P3-719.

113. F, D.-F., et al., *Molecular analysis of the calcium-sensing receptor (CaSR) gene in 40 patients suspected to have familial hypocalciuric hypercalcemia (FHH)*. European Congress of Endocrinology 2008 Endocrine Abstracts 16: OC4.7.

114. F, D. L., et al., *Sporadic hypoparathyroidism caused by de novo gain-of-function mutations of the Ca(2+)-sensing receptor*. Journal of Clinical Endocrinology and Metabolism 1997 82: 2710-2715.

115. F, H., et al., *A novel homozygous inactivating mutation, Pro339Thr, of the calcium-sensing receptor is associated with isolated primary hyperparathyroidism*. Endo Abstracts 2007 13 OC9.

116. FH, Y., et al., *Genetic variation at the calcium-sensing receptor (CASR) locus: implications for clinical molecular diagnostics*. Clinical Biochemistry 2007 8: 551-61.

117. FHJ, C. D. Y., et al., *Calcium-sensing receptor (CASR) mutations and denaturing high performance liquid chromatography (DHPLC)*. Journal of Molecular Endocrinology 2009 4: 331-9.

118. G, S., et al., *Calcium metabolism and endocrine functions in a family with familial hypocalciuric hypercalcemia*. Experimental and clinical endocrinology & diabetes 2003 111: 486-490.

119. G, T. J. C., et al., *Neonatal severe hyperparathyroidism associated with a novel de novo heterozygous R551K inactivating mutation and a heterozygous A986S polymorphism of the calcium-sensing receptor gene*. Clinical Endocrinology 2007 67: 385-392.

120. G, V., et al., *R990G polymorphism of calcium-sensing receptor does produce a gain-of-function and predispose to primary hypercalciuria*. Kidney International 2007 11: 1155-62.

121. GN, H., et al., *Recurrent familial hypocalcemia due to germline mosaicism for an activating mutation of the calcium-sensing receptor gene*. Journal of Clinical Endocrinology and Metabolism 2003 88:3674-3681.

122. H, H., et al., *A novel activating mutation (C129S) in the calcium-sensing receptor in a Japanese family with autosomal dominant hypocalcemia*. Journal of Human Genetics 2001 46: 41-44.

123. HJLM, T., et al., *Normalization of serum calcium by cinacalcet in a patient with hypercalcaemia due to a de novo inactivating mutation of the calcium-sensing receptor*. Journal of Internal Medicine 2006 260: 177-182.

124. III, H. H., et al., *Clustered inactivation utations and benign polymorphisms of the calcium receptor gene in familial benign hypocalciuric hypercalcemia suggest receptor functional domains*. Journal of Clinical Endocrinology and Metabolism 1996 81: 1312-1317.

125. J, B., et al., *Mutations in the Ca2+-sensing receptor gene cause autosomal dominant and sporadic hypoparathyroidism*. Human Molecular Genetics 1996 5: 601-606.

126. J, H., et al., *Autosomal dominant hypocalcemia caused by a novel mutation in the loop 2 region of the human calcium receptor extracellular domain*. Journal of Bone and Mineral Research 2002 17: 1461-1469.

127. J, H., et al., *Autosomal dominant hypocalcemia in monozygotic twins caused by a de novo germline mutation near the amino-terminus of the human calcium receptor*. Journal of Bone and Mineral Research 2004 19: 578-586.

128. J, H., et al., *A region in the seven-transmembrane domain of the human Ca2+ receptor critical for response to Ca2+*. The Journal of Biological Chemistry 2005 280:5113-5120.

129. J, N., et al., *New mutations of calcium-sensing receptor gene in two Japanese patients with sporadic hypoparathyroidism with hypercalciuria*. XVth International Symposium of Endocrinology and Development, Paris, France., 1997 Horm. Res. 48: 798, 179.

130. J, R., et al., *A novel calcium-sensing receptor gene mutation in a family with an extensive history of familial hypocalciuric hypercalcemia*. British Endocrine Societies Joint Meeting 2005 Endocrine Abstracts P: P183.

131. J, W., et al., *Genetic testing in familial isolated hyperparathyroidism: unexpected results and their implications*. Journal of Medical Genetics 2004 41: 155-160.

132. JL, S., et al., *Autosomal dominant hypoparathyroidism associated with short stature and premature osteoarthritis*. Journal of Clinical Endocrinology and Metabolism 1999 84: 3036-3040.

133. JT, D. D. and A. SE *Nomenclature for the description of human sequence variations*. Human Genetics 2001 109: 121-124.

134. K, A., et al., *Familial hypocalciuric hypercalcemia associated with mutation in the human Ca2+-sensing receptor gene*. Journal of Clinical Endocrinology and Metabolism 1995 80: 2594-2598.

135. K, B., et al., *Parathyroid adenoma in a subject with familial hypocalciuric hypercalcemia: coincidence or causality? Journal of Clinical Endocrinology and Metabolism* 2002 87: 1015-1016.

136. K, M., et al., *Severe hypercalcemia in a 9-year-old Brazilian girl due to a novel inactivating mutation of the calcium-sensing receptor*. Journal of Clinical Endocrinology and Metabolism 2004 89: 5936-5941.

137. K, M., et al., *Identification and functional analysis of a novel inactivating mutation (A804D) of the calcium-sensing receptor gene*. Clinical Endocrinology 2004 61: 780-782.

138. K, N., et al., *Hypocalciuric hypercalcemia presenting as neonatal rib fractures*. Pediatric Emergency Care 2006 22: 722-724.

139. K, P., et al., *Citrate infusion test in the diagnosis of hypocalcemia due to a mutation in the calcium-sensing receptor gene*. European Journal of Internal Medicine 2002 13: 276-279.

140. K, S., et al., *Hydrochlorothiazide effectively reduces urinary calcium excretion in two Japanese patients with gain-of-function mutations of the calcium-sensing receptor gene*. Journal of Clinical Endocrinology and Metabolism 2002 87: 3068-3073.

141. L, D. S.-L., et al., *Identification and functional characterization of novel calcium-sensing receptor muta-* tions in familial hypocalciuric hypercalcemia and autosomal dominant hypocalcemia. Journal of Clinical Endocrinology and Metabolism 2002 87:1309-1318.

142. L, D. S.-L., et al., *An acceptor slice site mutation in the calcium-sensing receptor (CASR) gene in familial hypocalciuric hypercalcemia and neonatal severe hyperparathyroidism*. Human Mutation 2001 18: 411-421.

143. L, D. S.-L., et al., *Two novel mutations in the calcium-sensing receptor gene in familial hypocalciuric hypercalcemia and neonatal severe hyperparathyroidism*. Journal of Bone and Mineral Research 2002 17s1: M438.

144. L, F., et al., *Neonatal hyperparathyroidism and pamidronate therapy in an extremely premature infant*. Pediatrics 2007 120: e1350-1354.

145. LS, R., et al., *New mutation in the CaSR involving three generation in a family with hypocalciuric hypercalcemia*. Endocrine Society Congress 2009 P2-204.

146. M, B., et al., *Expression and characterization of inactivating and activating mutations in the human Ca2+-osensing receptor*. The Journal of Biological Chemistry 1996 32: 19537-45.

147. M, B., et al., *In vivo and in vitro characterization of neonatal hyperparathyroidism resulting from a de novo, heterozygous mutation in the Ca2+-sensing receptor gene: normal maternal calcium homeostasis as a cause of secondary hyperparathyroidism in familial benign hypocalciuric hypercalcemia*. Journal of Clinical Investigation 1997 99: 88-96.

148. M, D., et al., *A new missense mutation in the CASR gene in familial interstitial lung disease with hypocalciuric hypercalcemia and defective granulocyte function*. American journal of respiratory and critical care medicine 2008 177: 558-559.

149. M, H., et al., *Benigne familiare hypoka/ziurische hyperka/zamie (FHH)? neue mutation des calcium sensing receptors (CaSR) bei einem 7-juhrigen madchen*. Jahrestagung der Sachsisch-Thuringischen Gesellschaft fur Kinder- und Jugendmedizin und Kinderchirurgie am 04. und 05. April 2008 in Chenitz 2008 Abstract P29.

150. M, K., et al., *Two novel missense mutations in calcium-sensing receptor gene associated with neonatal severe hyperparathyroidism*. Journal of Clinical Endocrinology and Metabolism 1997 82: 2716-2719.

151. M, S., F. E, and Z. J Hypocalciuric hypercalcemia due to de novo mutation of the calcium-sensing receptor. Medicina (Buenos Aires) 2004 64: 337-339.

152. M, S., et al., *A case of gain-of-function mutation in calcium-sensing receptor: supplemental hydration is required for renal protection*. Clinical Nephrology 2005 63: 481-486.

153. M, S., et al., *A novel gain-of-function mutation (F821L) in the transmembrane domain of calcium-sensing receptor is a cause of severe sporadic hypoparathyroidism*. European Journal of Pediatrics 2004 163:94-98.

154. M, Y., et al., *Comparison of hypocalcemic hypercalciuria between patients with idiopathic hypoparathyroidism and those with gain-of-function mutations in the calcium-sensing receptor: is it possible to differentiate the two disorders?* Journal of Clinical Endocrinology and Metabolism 2000 85: 4583-4591.

155. M, Y., et al., *Familial hypocalciuric hypercalcemia caused by a R648 stop mutation in the calcium sensing receptor gene*. Journal of Bone Mineral Research 2002 17: 2174-2182.

156. MR, B., et al., *Late Presentation of an Infant with Neonatal Severe Hyperparathyroidism*. Journal of Bone and Mineral Research 2001 16s1: Abstract SU510, page S428.

157. MR, P., et al., *Autosomal dominant hypocalcemia caused by a Ca2+-sensing receptor gene mutation*. Nature Genetics 1994 8: 303-307.

158. MR, P., et al., *Mutations in the human Ca2+-sensing receptor gene cause familial hypocalciuric hypercalcemia and neonatal severe hyperparathyroidism*. Cell 1993 75: 1297-1303.

159. N, C., et al., *An adult patient with severe hypercalcaemia and hypocalciuria due to a novel homozygous inactivating mutation of calcium-sensing receptor*. Clinical Endocrinology 1999 50: 537-543.

160. N, C., et al., *A family of autosomal dominant hypocalcemia with an activating mutation of calcium-sensing receptor gene*. Endocrine Journal 2003 50: 91-96.

161. N, J., et al., *Mapping of the calcium-sensing receptor gene (CASR) to human chromosome 3q13.3-21 by fluorescence in situ hybridization, and localization to rat chromosome 11 and mouse chromosome 16*. Mammalian Genome 1995 6: 798-801.

162. N, J., et al., *Insertion of an Alu sequence in the Ca2+-sensing receptor gene in familial hypocalciuric hypercalcemia and neonatal severe hyperparathyroidism*. American Journal of Human Genetics 1999 56: 880-886.

163. P, C., et al., *Characterization of 25 calcium-sensing receptor mutations in disorders of calcium homeostasis*. Society for Endocrinology. BES Endocrine 2007 Abstracts 13: P1.

164. P, F., et al., *A novel mutation of the calcium sensing receptor gene is associated with chronic pancreatitis in a family with heterozygous SPINK1 mutations*. BMC Gastroenterology 2003 3:34:00.

165. P, F., et al., *Identification of a novel calcium-sensing receptor gene mutation causing familial hypocalciuric hypercalcemia by single-strand conformation polymorphism analysis*. Experimental and clinical endocrinology & diabetes 2005 113: 31-34.

166. P, F., et al., *Mutations in the calcium-sensing receptor: a new genetic risk factor for chronic pancreatitis?* Scandinavian Journal of Gastroenterology 2006 41:343-348.

167. P, S., et al., *Familial hypocalciuric hypercalcemia and neonatal severe hyperparathyroidism associated with mutations in the human Ca2+-sensing receptor gene in three Danish families*. Scandinavian Journal of Clinical and Laboratory Investigation 2000 60: 221-227.

168. PH, N., et al., *Molecular genetic analysis of the calcium sensing receptor gene in patients clinically suspected to have familial hypocalciuric hypercalcemia: phenotypic variation and mutation spectrum in a Danish population*. Journal of Clinical Endocrinology and Metabolism 2007 92: 4373-4379.

169. Pidasheva, et al., *Impaired cotranslational processing of the calcium-sensing receptor due to signal peptide missense mutations in familial hypocalciuric hypercalcemia*. Human Molecular Genetics 2005 14:1679-1690.

170. Pidasheva, et al., *The calcium-sensing receptor (CASR) dimerizes in the endoplasmic reticulum: biochemical and biophysical characterization of novel CASR mutations causing familial hypocalciuric hypercalcemia*. Human Molecular Genetics 2006 15:2200-2209.

171. PT, C., et al., *An activating calcium sensing receptor mutation associated with normocalcemic (idiopathic) hypercalciuric nephrolithiasis*. Journal of Bone and Mineral Research 2002 17s1: S127, Abs 1008.

172. Q, D., et al., *Naturally-occurring mutation in the calcium-sensing receptor (CaSR) reveals the significance of extracellular domain loop III for receptor and signal transduction*. Endocrine Society Congress 2009 OR30-5.

173. R, L., et al., *The Ca2+-sensing receptor gene (PCAR1) mutation T151 M in isolated autosomal dominant hypoparathyroidism.* Human Genetics 1996 98: 129-133.

174. R, M., et al., *Familial hypocalciuric hypercalcemia (FHH) caused by P748L mutation in the calcium sensing receptor (CaSR) gene.* European Congress of Endocrinology 2006 Endocrine Abstracts 11 P163.

175. R, O., et al., *A novel activating mutation in calcium-sensing receptor gene associated with a family of autosomal dominant hypocalcemia.* Journal of Clinical Endocrinology and Metabolism 1999 84: 363-366.

176. R, R., et al., *Novel inactivating mutations of the calcium-sensing receptor: the calcimimetic NPS-R-568 improves signal transduction of mutant receptors.* Journal of Clinical Endocrinology and Metabolism 2008 93: 4797-4803.

177. R, V.-P., et al., *Functional characterization of a calcium-sensing receptor mutation in severe autosomal dominant hypocalcemia with a Bartter-like syndrome.* Journal of the American Society of Nephrology 2002 13: 2259-2266.

178. Rajguru, et al., *Neonatal primary hyperparathyroidism due to a new calcium sensing receptor mutation.* Pediatircs Research 2001 49s: P3-294.

179. RC, M., et al., *A novel CASR gene mutation in an octogenarian with asymptomatic hypercalcemia.* Hong Kong Medical Journal 2008 14: 226-228.

180. S, A., et al., *Marked hypercalcemia in a five month old male associated with heterozygous point mutation in the calcium-sensing receptor gene.* Prog & Abs 80th Ann Meet Endo Soc 1998 p. 493 Abs. P3-535.

181. S, F., et al., *Inactivating mutations of calcium-sensing receptor results in parathyroid lipohyperplasia.* Diagnostic Molecular Pathology 2001 10: 242-247.

182. S, M., et al., *Severe hypocalcemia due to a de novo mutation in the fifth transmembrane domain of the calcium-sensing receptor.* Americal Journal of Medical Genetics 2006 140A: 98-101.

183. S, S., S. K P, and N. RS *Autosomal dominant hypoparathyroidism with severe hypomagnesemia and hypocalcemia, successfully treated with recombinant PTH and continuous magnesium infusion.* Journal of Pediatric Endocrinology and Metabolism 2008 21: 385-391.

184. S, W., et al., *Association between activating mutations of calcium-sensing receptor and Bartter?s syndrome.* Lancet 2002 360: 692-694.

185. S, W., et al., *Neonatal severe hyperparathyroidism: genotype/phenotype correlation and the use of pamidronate as rescue therapy.* European Journal of Pediatrics 2004 163: 589-594.

186. SC, D. A., K. SK, and D. S.-L. L *Novel mutation of the calcium-sensing receptor gene in familial hypocalciuric hypercalcemia and neonatal severe hyperparathyroidism.* Clinical Endocrinology 2006 65: 826-831.

187. SD, M., et al., *A hypocalcemic child with a novel activating mutation of the calcium-sensing receptor gene: successful treatment with recombinant human parathyroid hormone.* Journal of Clinical Endocrinology and Metabolism 2006 91: 2474-2479.

188. SHS, P., et al., *Calcium-sensing receptor mutations in familial hypocalciuric hypercalcaemia with recurrent pancreatitis.* Clinical Endocrinology 1996 45: 675-680.

189. SHS, P., et al., *A familial syndrome of hypocalcemia with hypercalciuria due to mutations in the calcium-sensing receptor.* New England Journal of Medicine 1996 335: 1115-1122.

190. SHS, P., et al., *Calcium-sensing receptor mutations in familial benign hypercalcemia and neonatal hyperparathyroidism.* Journal of Clinical Investigation 1995 2683-2692.

191. SHS, P., et al., *Functional characterization of calcium-sensing receptor mutations expressed in human embryonic kidney cells.* Journal of Clinical Investigation 1996 98: 1860-1866.

192. SI, W., et al., *A case report of familial benign hypocalciuric hypercalcemia: a mutation in the calcium-sensing receptor gene.* Yonsei Medical Journal 2006 47: 255-258.

193. SK, S., T. S, and H. GN *Novel inactivating mutation of the calcium-sensing receptor associated with familial hypocalciuric hypercalcemia.* Pediatric Academic Societies Annual Meeting. Honolulu Hi. May 3-6 2008 Board N 697, Course N 3798.

194. T, C., et al., *Familial hypercalcemia and hypercalciuria caused by a novel mutation in the cytoplasmic tail of the calcium receptor.* Journal of Clinical Endocrinology and Metabolism 2000 85: 2042-2047.

195. T, N., et al., *A novel mutation in Ca2+-sensing receptor gene in familial hypocalciuric hypercalcemia.* Endocrine 2001 15: 277-282.

196. T, W., et al., *Familial hypoparathyroidism: identification of a novel gain of function mutation in transmembrane domain 5 of the calcium-sensing receptor.* Journal of Clinical Endocrinology and Metabolism 1998 83: 2497-2502.

197. T-S, J., et al., *A novel mutation in the calcium-sensing receptor gene in a Chinese subject with persistent hypercalcemia and hypocalciuria.* Journal of Clinical Endocrinology and Metabolism 2001 86: 13-15.

198. V, G., et al., *Calcium-sensing Receptor (CASR) Mutations in Hypercalcemic States: Functional Analyses of Novel and Recurrent Mutations Identified in a Single Endocrine Clinic Over Three Years.* ASMR Congress 2009 Abstract.

199. WF, S., et al., *Familial isolated hyperparathyroidism. Clinical and genetic characteristics of 36 kindreds.* Medicine 2002 81: 1-26.

200. Wystrychowski, et al., *Functional characterization of calcium-sensing receptor codon 227 mutations presenting either as familial (benign) hypocalciuric hypercalcemia or neonatal hyperparathyroidism.* Journal of Clinical Endocrinology and Metabolism 2005 90:864-870.

201. XM, Z., et al., *A missense mutation in the seventh transmembrane domain constitutively activates the human Ca2+ receptor.* Febs Letter 1999 448:180-184.

202. Y, O., et al., *Insulinoma cell calcium-sensing receptor influences insulin secretion in a case with concurrent familial hypocalciuric hypercalcemia and malignant metastatic insulinoma.* European Journal of Endocrinology 2008 159: 81-89.

203. YH, C., et al., *Mutations of the human Ca(2+)-sensing receptor gene that cause familial hypocalciuric hypercalcemia.* American Journal of Human Genetics 1995 56: 1075-1079.

204. YL, S., et al., *Familial benign hypercalcemia (FBH) with age-associated hypercalciuria and a missense mutation in the calcium-sensing receptor (CaSR) expands the spectrum of the syndrome towards primary hyperparathyroidism.* Journal of Bone Mineral Research 1999 14s1: SU062, S447.

205. YM, T., et al., *Autosomal dominant hypocalcemia: a novel activating mutation (E604K) in the cysteine-rich domain of the calcium-sensing receptor.* Journal of Clinical Endocrinology and Metabolism 2003 88: 605-610.

206. YP, C., et al., *Three novel activating mutations in the calcium-sensing receptor for autosomal dominant hypocalcemia*. Molecular Genetics and Metabolism 2000 71: 591-598.

207. Z, Z., et al., *Identification and functional characterization of a novel mutation in the calcium-sensing receptor in familial hypocalciuric hypercalcemia: modulation of clinical severity by vitamin D status*. Journal of Clinical Endocrinology and Metabolism 2007 92: 2616-2623.

208. Kirberger, M., et al., *Statistical analysis of structural characteristics of protein Ca2+-binding sites*. J Biol Inorg Chem, 2008. 13(7): p. 1169-81.

209. Wang, X., et al., *Analysis and prediction of calcium-binding pockets from apo-protein structures exhibiting calcium-induced localized conformational changes*. Protein Sci, 2010. 19(6): p. 1180-90.

210. Zhao, K., et al., *Predicting Ca2+-binding sites using refined carbon clusters*. Proteins, 2012. 80(12): p. 2666-79.

211. Zhou, Y., et al., *Prediction of EF-hand calcium-binding proteins and analysis of bacterial EF-hand proteins*. Proteins, 2006. 65(3): p. 643-55.

212. Case, D. A., et al., *The Amber biomolecular simulation programs*. J Comput Chem, 2005. 26(16): p. 1668-88.

213. Hornak, V., et al., *Comparison of multiple Amber force fields and development of improved protein backbone parameters*. Proteins, 2006. 65(3): p. 712-25.

214. Zhang, C., et al., *Role of Ca2+ and L-Phe in regulating functional cooperativity of disease-associated "toggle" calcium-sensing receptor mutations*. PLoS One, 2014. 9(11): p. e113622.

215. Hannan, F. M., et al., *Identification of 70 calcium-sensing receptor mutations in hyper-and hypo-calcaemic patients: evidence for clustering of extracellular domain mutations at calcium-binding sites*. Hum Mol Genet, 2012. 21(12): p. 2768-78.

216. Rodriguez-Ortiz, M. E., et al., *Magnesium modulates parathyroid hormone secretion and upregulates parathyroid receptor expression at moderately low calcium concentration*. Nephrol Dial Transplant, 2014. 29(2): p. 282-9.

217. Hebert, S. C., E. M. Brown, and H. W. Harris, *Role of the Ca(2+)-sensing receptor in divalent mineral ion homeostasis*. J Exp Biol, 1997. 200 (Pt 2): p. 295-302.

218. Hentschel, H., et al., *Localization of Mg2+-sensing shark kidney calcium receptor SKCaR in kidney of spiny dogfish, Squalus acanthias*. Am J Physiol Renal Physiol, 2003. 285(3): p. F430-9.

219. Horowicz, P. and J. W. Burger, *Unidirectional fluxes of sodium ions in the spiny dogfish, Squalus acanthias*. Am J Physiol, 1968. 214(3): p. 635-42.

220. Bai, M., et al., *Expression and characterization of inactivating and activating mutations in the human Ca2+ o-sensing receptor*. J Biol Chem, 1996. 271(32): p. 19537-45.

221. Nearing, J., et al., *Polyvalent cation receptor proteins (CaRs) are salinity sensors in fish*. Proc Natl Acad Sci USA, 2002. 99(14): p. 9231-6.

222. Bapty, B. W., et al., *Extracellular Mg2(+)-and Ca2 (+)-sensing in mouse distal convoluted tubule cells*. Kidney Int, 1998. 53(3): p. 583-92.

223. Huang, Y., et al., *Multiple Ca(2+)-binding sites in the extracellular domain of the Ca(2+)-sensing receptor corresponding to cooperative Ca(2+) response*. Biochemistry, 2009. 48(2): p. 388-98.

224. Huang, Y., et al., *A single EF-hand isolated from STIM1 forms dimer in the absence and presence of Ca2+*. FEBS J, 2009. 276(19): p. 5589-97.

225. Huang, Y., et al., *Identification and dissection of Ca(2+)-binding sites in the extracellular domain of Ca(2+)-sensing receptor*. J Biol Chem, 2007. 282(26): p. 19000-10.

226. Jiang, J., et al., *Site-specific modification of calmodulin Ca(2)(+) affinity tunes the skeletal muscle ryanodine receptor activation profile*. Biochem J. 432(1): p. 89-99.

227. Jiang, Y. F., et al., *Protein kinase C (PKC) phosphorylation of the Ca2+ o-sensing receptor (CaR) modulates functional interaction of G proteins with the CaR cytoplasmic tail*. J Biol Chem, 2002. 277(52): p. 50543-9.

228. Kubo, Y., T. Miyashita, and Y. Murata, *Structural basis for a Ca2+-sensing function of the metabotropic glutamate receptors*. Science, 1998. 279(5357): p. 1722-5.

229. Zhuo, Y., et al., *Effect of Ca(2)(+) on the steady-state and time-resolved emission properties of the genetically encoded fluorescent sensor CatchER*. J Phys Chem B, 2015. 119(6): p. 2103-11.

230. Muto, T., et al., *Structures of the extracellular regions of the group II/III metabotropic glutamate receptors*. Proc Natl Acad Sci USA, 2007. 104(10): p. 3759-64.

231. Niswender, C. M. and P. J. Conn, *Metabotropic glutamate receptors: physiology, pharmacology, and disease*. Annu Rev Pharmacol Toxicol, 2010. 50: p. 295-322.

232. Tan, Y. M., et al., *Autosomal dominant hypocalcemia: a novel activating mutation (E604K) in the cysteine-rich domain of the calcium-sensing receptor*. J Clin Endocrinol Metab, 2003. 88(2): p. 605-10.

233. Casado, V., et al., *Old and new ways to calculate the affinity of agonists and antagonists interacting with G-protein-coupled monomeric and dimeric receptors: the receptor-dimer cooperativity index*. Pharmacol Ther, 2007. 116(3): p. 343-54.

234. Christopoulos, A. and T. Kenakin, *G protein-coupled receptor allosterism and complexing*. Pharmacol Rev, 2002. 54(2): p. 323-74.

235. Durroux, T., *Principles: a model for the allosteric interactions between ligand binding sites within a dimeric GPCR*. Trends Pharmacol Sci, 2005. 26(7): p. 376-84.

236. Kenakin, T., *Allosteric modulators: the new generation of receptor antagonist*. Mol Interv, 2004. 4(4): p. 222-9.

237. Kenakin, T., *G-protein coupled receptors as allosteric machines*. Receptors Channels, 2004. 10(2): p. 51-60.

238. Zhou, Y., et al., *Identification of a Ca2+-binding domain in the rubella virus nonstructural protease*. J Virol, 2007. 81(14): p. 7517-28.

239. Ye, Y., et al., *Calcium and lanthanide affinity of the EF-loops from the C-terminal domain of calmodulin*. J Inorg Biochem, 2005. 99(6): p. 1376-83.

240. Horrocks, W. D., Jr., B. Holmquist, and B. L. Vallee, *Energy transfer between terbium (III) and cobalt (II) in thermolysin: a new class of metal-metal distance probes*. Proc Natl Acad Sci USA, 1975. 72(12): p. 4764-8.

241. Markowitz, J., et al., *Calcium-binding properties of wild-type and EF-hand mutants of S1008 in the presence and absence of a peptide derived from the C-terminal negative regulatory domain of p53*. Biochemistry, 2005. 44(19): p. 7305-14.

242. Forsen, S. and S. Linse, *Cooperativity: over the Hill*. Trends Biochem Sci, 1995. 20(12): p. 495-7.

243. Yang, W., et al., *Rational design of a calcium-binding protein*. J Am Chem Soc, 2003. 125(20): p. 6165-71.

244. Ye, Y., et al., *Metal binding affinity and structural properties of an isolated EF-loop in a scaffold protein*. Protein Eng, 2001. 14(12): p. 1001-13.

245. Sridharan, R., et al., *Fluorescent approaches for understanding interactions of ligands with G protein coupled receptors.* Biochim Biophys Acta, 2014. 1838(1 Pt A): p. 15-33.

246. Dolmetsch, R. E., K. Xu, and R. S. Lewis, *Calcium oscillations increase the efficiency and specificity of gene expression.* Nature, 1998. 392(6679): p. 933-6.

247. Miedlich, S., L. Gama, and G. E. Breitwieser, *Calcium sensing receptor activation by a calcimimetic suggests a link between cooperativity and intracellular calcium oscillations.* J Biol Chem, 2002. 277(51): p. 49691-9.

248. Young, S. H. and E. Rozengurt, *Amino acids and Ca2+ stimulate different patterns of Ca2+ oscillations through the Ca2+-sensing receptor.* Am J Physiol Cell Physiol, 2002. 282(6): p. C1414-22.

249. Thomsen, A. R., et al., *Strontium is a biased agonist of the calcium-sensing receptor in rat medullary thyroid carcinoma 6-23 cells.* J Pharmacol Exp Ther, 2012. 343(3): p. 638-49.

250. Huang, C. and R. T. Miller, *The calcium-sensing receptor and its interacting proteins.* J Cell Mol Med, 2007. 11(5): p. 923-34.

251. Wellendorph, P. and H. Brauner-Osborne, *Molecular basis for amino acid sensing by family C G-protein-coupled receptors.* Br J Pharmacol, 2009. 156(6): p. 869-84.

252. Cheng, S. X., J. P. Geibel, and S. C. Hebert, *Extracellular polyamines regulate fluid secretion in rat colonic crypts via the extracellular calcium-sensing receptor.* Gastroenterology, 2004. 126(1): p. 148-58.

253. Tu, C. L., et al., *The role of the calcium-sensing receptor in epidermal differentiation.* Cell Calcium, 2004. 35(3): p. 265-73.

254. Vaidehi, N., S. Bhattacharya, and A. B. Larsen, *Structure and dynamics of G-protein coupled receptors.* Adv Exp Med Biol, 2014. 796: p. 37-54.

255. Loria, J. P., M. Rance, and A. G.r. Palmer, *A Relaxation-Compensated Carr-Purcell-Meiboom-Gill Sequence for Characterizing Chemical Exchange by NMR Spectroscopy.* Journal of the American Chemical Society, 1999. 121(10): p. 2331-2332.

256. Mulder, F. A., et al., *Slow internal dynamics in proteins: application of NMR relaxation dispersion spectroscopy to methyl groups in a cavity mutant of T4 lysozyme.* Journal of the American Chemical Society, 2002. 124(7): p. 1443-51.

257. Tolkatchev, D., P. Xu, and F. Ni, *Probing the kinetic landscape of transient peptide-protein interactions by use of peptide (15)n NMR relaxation dispersion spectroscopy: binding of an antithrombin peptide to human prothrombin.* Journal of the American Chemical Society, 2003. 125(41): p. 12432-42.

258. Kempf, J. G., et al., *Dynamic requirements for a functional protein hinge.* Journal of Molecular Biology, 2007. 368(1): p. 131-49.

259. Tugarinov, V., et al., *Cross-correlated relaxation enhanced 1H[bond]13C NMR spectroscopy of methyl groups in very high molecular weight proteins and protein complexes.* Journal of the American Chemical Society, 2003. 125(34): p. 10420-8.

260. Macnaughtan, M. A., A. M. Kane, and J. H. Prestegard, *Mass spectrometry assisted assignment of NMR resonances in reductively 13C-methylated proteins.* J Am Chem Soc, 2005. 127(50): p. 17626-7.

261. Liu, Y., R. A. Kahn, and J. H. Prestegard, *Dynamic structure of membrane-anchored Arf*GTP.* Nat Struct Mol Biol. 17(7): p. 876-81.

262. Zhang, C. M., N.; Hannan, F.; Nesbit, M; Thakker, R; Hamelberg, D.; Brown, E.; Yang, J., *Role of Ca2+ and L-Phe in Regulating Functional Cooperativity of Disease-Associated "Toggle" Calcium-Sensing Receptor Mutations.* To be submitted, 2014.

263. Alexander, S. T., et al., *Critical Cysteine Residues in Both the Calcium-Sensing Receptor and the Allosteric Activator AMG 416 Underlie the Mechanism of Action.* Mol Pharmacol, 2015. 88(5): p. 853-65.

264. Martin, K. J., et al., *AMG 416 (velcalcetide) is a novel peptide for the treatment of secondary hyperparathyroidism in a single-dose study in hemodialysis patients.* Kidney Int, 2014. 85(1): p. 191-7.

265. Nemeth, E. F. and W. G. Goodman, *Calcimimetic and Calcilytic Drugs: Feats, Flops, and Futures.* Calcif Tissue Int, 2015.

266. Chen, P., et al., *Population pharmacokinetics analysis of AMG 416, an allosteric activator of the calcium-sensing receptor, in subjects with secondary hyperparathyroidism receiving hemodialysis.* J Clin Pharmacol, 2015. 55(6): p. 620-8.

267. Walter, S., et al., *Comparison of AMG 416 and cinacalcet in rodent models of uremia.* BMC Nephrol, 2014. 15: p. 81.

268. Shen, J., et al., *A pharmacokinetic/pharmacodynamic model for AMG 416, a novel calcimimetic peptide, following a single intravenous dose in healthy subjects.* J Clin Pharmacol, 2014. 54(10): p. 1125-33.

269. Martin, K. J., et al., *Velcalcetide (AMG 416), a novel peptide agonist of the calcium-sensing receptor, reduces serum parathyroid hormone and FGF23 levels in healthy male subjects.* Nephrol Dial Transplant, 2014. 29(2): p. 385-92.

270. Mayer, T., et al., *A mutant form of the rho protein can restore stress fibers and adhesion plaques in v-src transformed fibroblasts.* Oncogene, 1999. 18(12): p. 2117-28.

271. Streiff, J. H., et al., *Saturation transfer difference nuclear magnetic resonance spectroscopy as a method for screening proteins for anesthetic binding.* Mol Pharmacol, 2004. 66(4): p. 929-35.

272. Cook, A. E., et al., *Biased allosteric modulation at the CaS receptor engendered by structurally diverse calcimimetics.* Br J Pharmacol, 2015. 172(1): p. 185-200.

273. Kifor, O., et al., *Regulation of MAP kinase by calcium-sensing receptor in bovine parathyroid and CaR-transfected HEK293 cells.* Am J Physiol Renal Physiol, 2001. 280(2): p. F291-302.

274. Bai, M., et al., *In vivo and in vitro characterization of neonatal hyperparathyroidism resulting from a de novo, heterozygous mutation in the Ca2+-sensing receptor gene: normal maternal calcium homeostasis as a cause of secondary hyperparathyroidism in familial benign hypocalciuric hypercalcemia.* J Clin Invest, 1997. 99(1): p. 88-96.

275. Conigrave, A. D. and D. R. Hampson, *Broad-spectrum L-amino acid sensing by class 3 G-protein-coupled receptors.* Trends Endocrinol Metab, 2006. 17(10): p. 398-407.

276. Conigrave, A. D. and D. R. Hampson, *Broad-spectrum amino acid-sensing class C G-protein coupled receptors: molecular mechanisms, physiological significance and options for drug development.* Pharmacol Ther, 2010. 127(3): p. 252-60.

277. Rajagopal, S., K. Rajagopal, and R. J. Lefkowitz, *Teaching old receptors new tricks: biasing seven-transmembrane receptors.* Nat Rev Drug Discov, 2010. 9(5): p. 373-86.

278. Desguin, B., et al., *METALLOPROTEINS. A tethered niacin-derived pincer complex with a nickel-carbon bond in lactate racemase*. Science, 2015. 349(6243): p. 66-9.

279. Hu, J., et al., *Structural biology of transmembrane domains: efficient production and characterization of transmembrane peptides by NMR*. Protein Sci, 2007. 16(10): p. 2153-65.

280. Hu, J., et al., *Ligand binding in the conserved interhelical loop of CorA, a magnesium transporter from Mycobacterium tuberculosis*. J Biol Chem, 2009. 284(23): p. 15619-28.

281. Hu, J., et al., *The crystal structure of GXGD membrane protease FlaK*. Nature, 2011. 475(7357): p. 528-31.

282. Hu, J., et al., *Resolution of structure of PIP5K1A reveals molecular mechanism for its regulation by dimerization and dishevelled*. Nat Commun, 2015. 6: p. 8205

Example 3

Figures 33A, 33B:
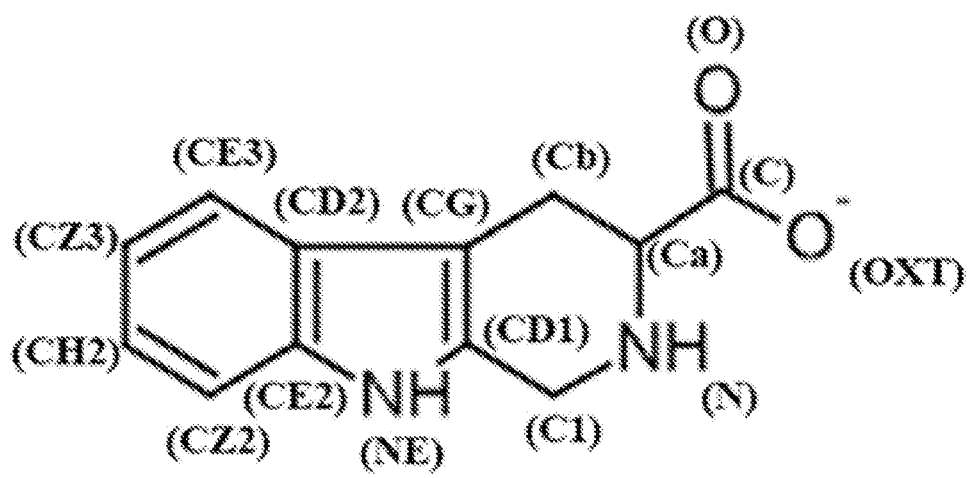
FIGS. 33A-33B can demonstrate the coordination of TNCA at the ligand binding site of CaSR-ECD. TNCA is coordinated by conserved residues at the ligand binding site of the ECD of the CaSR. The residues involved in TNCA binding include: S147, A168, S170, and Y218 for backbone binding, and W70, A298, I416 and E297 for sidechain binding. The detailed distance information is listed.

TNCA is coordinated by conserved residues at the native ligand binding site of CaSR-ECD (FIGS. 33A-33B). The residues involved in TNCA binding include: S147, A168, S170, and Y218 for backbone binding, and W70, A298, I416 and E297 for sidechain binding. The detailed distance information is listed in FIG. 37B.

We claim:

1. A method of treating a disease in a subject, the method comprising the step of:
administering an amount of L-1,2,3,4-tetrahydronorharman-3-carboxylic acid (TNCA) to the subject in need thereof, wherein the subject has a disease associated with a mutation of the extracellular calcium-binding domain (ECD) of a calcium-sensing receptor protein (CaSR) or a disease associated with abnormal CaSR expression or abnormal CaSR activity in a subject in need thereof.

2. The method of claim 1, wherein the amount of TCNA administered modulates the activity of a CaSR.

3. The method of claim 1, wherein the amount of TCNA administered increases the activity of a CaSR.

4. The method of claim 1, wherein the amount of TCNA administered decreases the activity of a CaSR.

5. The method of claim 1, wherein the disease is selected from the group consisting of: familial hypocalciuric hypercalcemia (FHH), autosomal dominant hypocalcemia (ADH), neonatal severe hyperparathyroidism (NSHPT), primary hyperparathyroidism (PHPT), severe secondary hyperparathyroidism in a patient receiving dialysis treatment for kidney failure, tertiary hyperparathyroidism, persistent or recurrent hyperparathyroidism, hyperparathyroidism occurring after renal transplantation, lithium-induced hyperparathyroidism, hypoparathyroidism, kidney stones, hypomagnesemia, hypermagnesemia, calciphylaxis osteoporosis dysfunction of the CaSR arising from activating or inactivating autoantibodies, hypocalcemia, hypercalcemia, a hypomagnesemia related disease, and a cancer associated with an altered expression of CaSR.

6. The method of claim 1, wherein the ECD has at least one amino acid mutation selected from the group consisting of: R25X, T138M, N118K, E127K/G/A, C129Y/F/S/R, L125P/F, P55L, C60F, R185Q, Q245R, R220W/P/Q, E250K, R227L, P221L/S, W208S, R172R/K, E297K/D, T151M/R/K, Q164X, and F351V, wherein the mutations are numbered in relation to SEQ ID NO.: 13, and wherein X represents any amino acid other than the wild-type amino acid.

7. The method of claim 1, wherein the TNCA is admixed with a pharmaceutically acceptable carrier.

8. The method of claim 1, wherein the amount is an amount effective to potentiate $Ca^{2+}$ or $Mg^{2+}$ activation of the CaSR.

9. A method comprising:
contacting an extracellular calcium-binding domain (ECD) of a calcium sensing receptor protein (CaSR) with L-1,2,3,4-tetrahydronorharman-3-carboxylic acid (TNCA) and a candidate compound suspected of modulating the activity of the CaSR; and
measuring CaSR activity or TNCA binding to the ECD.

10. The method of claim 9, wherein the L-1,2,3,4-tetrahydronorharman-3-carboxylic acid (TNCA) and the candidate compound simultaneously contact the ECD, and wherein the method comprises the step of directly or indirectly measuring TNCA binding to the ECD.

11. The method of claim 9, wherein the TNCA is detectably labeled.

12. The method of claim 9, wherein the amino acid sequence of the ECD is that of an ECD of a CaSR having amino acid sequence selected from SEQ ID NOS.: 1-18.

13. The method of claim 9, wherein the ECD has at least one mutation compared to an ECD of a CaSR having amino acid sequence selected from SEQ ID NOS.: 1-18.

14. The method of claim 9 wherein the ECD of the CaSR has a binding pocket configured by the amino acids S147, A168, S170, Y218, W70, A298, I416, and E297 of SEQ ID NO.: 13, or equivalents thereof.

15. The method of claim 9, wherein the ECD contains at least one mutation selected from R25X, T138/M, N118 K, E127K/G/A, C129Y/F/S/R, L125P/F, P55L, C60F, R185Q, Q245R, R220W/P/Q, E250K, R227L, P221L/S, W208S, R172R/K, E297K/D, T151M/R/K, Q164X, F351V, wherein the mutations are numbered according to SEQ ID NO.: 13, and wherein X represents any amino acid other than the wild-type amino acid.

16. The method of claim 9, wherein CaSR activity is measured by measuring $Ca^{2+}$ or $Mg^{2+}$ binding to the ECD.

* * * * *

SEQUENCE LISTING

<160> NUMBER OF SEQ ID NOS: 18

<210> SEQ ID NO 1
<211> LENGTH: 593
<212> TYPE: PRT
<213> ORGANISM: Homo sapiens

<400> SEQUENCE: 1

```
Tyr Gly Pro Asp Gln Arg Ala Gln Lys Lys Gly Asp Ile Ile Leu Gly
1               5                   10                  15

Gly Leu Phe Pro Ile His Phe Gly Val Ala Ala Lys Asp Gln Asp Leu
            20                  25                  30

Lys Ser Arg Pro Glu Ser Val Glu Cys Ile Arg Tyr Asn Phe Arg Gly
        35                  40                  45

Phe Arg Trp Leu Gln Ala Met Ile Phe Ala Ile Glu Glu Ile Asn Ser
    50                  55                  60

Ser Pro Ala Leu Leu Pro Asn Leu Thr Leu Gly Tyr Arg Ile Phe Asp
65                  70                  75                  80

Thr Cys Asn Thr Val Ser Lys Ala Leu Glu Ala Thr Leu Ser Phe Val
                85                  90                  95

Ala Gln Asn Lys Ile Asp Ser Leu Asn Leu Asp Glu Phe Cys Asn Cys
            100                 105                 110

Ser Glu His Ile Pro Ser Thr Ile Ala Val Val Gly Ala Thr Gly Ser
        115                 120                 125

Gly Val Ser Thr Ala Val Ala Asn Leu Leu Gly Leu Phe Tyr Ile Pro
    130                 135                 140

Gln Val Ser Tyr Ala Ser Ser Ser Arg Leu Leu Ser Asn Lys Asn Gln
145                 150                 155                 160

Phe Lys Ser Phe Leu Arg Thr Ile Pro Asn Asp Glu His Gln Ala Thr
                165                 170                 175

Ala Met Ala Asp Ile Ile Glu Tyr Phe Arg Trp Asn Trp Val Gly Thr
            180                 185                 190

Ile Ala Ala Asp Asp Asp Tyr Gly Arg Pro Gly Ile Glu Lys Phe Arg
        195                 200                 205

Glu Glu Ala Glu Glu Arg Asp Ile Cys Ile Asp Phe Ser Glu Leu Ile
    210                 215                 220

Ser Gln Tyr Ser Asp Glu Glu Ile Gln His Val Val Glu Val Ile
225                 230                 235                 240

Gln Asn Ser Thr Ala Lys Val Ile Val Val Phe Ser Ser Gly Pro Asp
                245                 250                 255

Leu Glu Pro Leu Ile Lys Glu Ile Val Arg Arg Asn Ile Thr Gly Lys
            260                 265                 270

Ile Trp Leu Ala Ser Glu Ala Trp Ala Ser Ser Ser Leu Ile Ala Met
```

```
                275                 280                 285
Pro Gln Tyr Phe His Val Val Gly Gly Thr Ile Gly Phe Ala Leu Lys
        290                 295                 300
Ala Gly Gln Ile Pro Gly Phe Arg Glu Phe Leu Lys Lys Val His Pro
305                 310                 315                 320
Arg Lys Ser Val His Asn Gly Phe Ala Lys Glu Phe Trp Glu Glu Thr
                325                 330                 335
Phe Asn Cys His Leu Gln Glu Gly Ala Lys Gly Pro Leu Pro Val Asp
            340                 345                 350
Thr Phe Leu Arg Gly His Glu Glu Ser Gly Asp Arg Phe Ser Asn Ser
        355                 360                 365
Ser Thr Ala Phe Arg Pro Leu Cys Thr Gly Asp Glu Asn Ile Ser Ser
370                 375                 380
Val Glu Thr Pro Tyr Ile Asp Tyr Thr His Leu Arg Ile Ser Tyr Asn
385                 390                 395                 400
Val Tyr Leu Ala Val Tyr Ser Ile Ala His Ala Leu Gln Asp Ile Tyr
                405                 410                 415
Thr Cys Leu Pro Gly Arg Gly Leu Phe Thr Asn Gly Ser Cys Ala Asp
            420                 425                 430
Ile Lys Lys Val Glu Ala Trp Gln Val Leu Lys His Leu Arg His Leu
        435                 440                 445
Asn Phe Thr Asn Asn Met Gly Glu Gln Val Thr Phe Asp Glu Cys Gly
    450                 455                 460
Asp Leu Val Gly Asn Tyr Ser Ile Ile Asn Trp His Leu Ser Pro Glu
465                 470                 475                 480
Asp Gly Ser Ile Val Phe Lys Glu Val Gly Tyr Tyr Asn Val Tyr Ala
                485                 490                 495
Lys Lys Gly Glu Arg Leu Phe Ile Asn Glu Glu Lys Ile Leu Trp Ser
            500                 505                 510
Gly Phe Ser Arg Glu Val Pro Phe Ser Asn Cys Ser Arg Asp Cys Leu
        515                 520                 525
Ala Gly Thr Arg Lys Gly Ile Ile Glu Gly Glu Pro Thr Cys Cys Phe
    530                 535                 540
Glu Cys Val Glu Cys Pro Asp Gly Glu Tyr Ser Asp Glu Thr Asp Ala
545                 550                 555                 560
Ser Ala Cys Asn Lys Cys Pro Asp Asp Phe Trp Ser Asn Glu Asn His
                565                 570                 575
Thr Ser Cys Ile Ala Lys Glu Ile Glu Phe Leu Ser Trp Thr Glu Pro
            580                 585                 590
Phe

<210> SEQ ID NO 2
<211> LENGTH: 600
<212> TYPE: PRT
<213> ORGANISM: Artificial Sequence
<220> FEATURE:
<223> OTHER INFORMATION: human CaSR with FLAG Tag

<400> SEQUENCE: 2

Tyr Gly Pro Asp Gln Arg Ala Gln Lys Lys Gly Asp Ile Ile Leu Gly
1               5                   10                  15
Gly Leu Phe Pro Ile His Phe Gly Val Ala Ala Lys Asp Gln Asp Leu
            20                  25                  30
Lys Ser Arg Pro Glu Ser Val Glu Cys Ile Arg Tyr Asn Phe Arg Gly
        35                  40                  45
```

-continued

```
Phe Arg Trp Leu Gln Ala Met Ile Phe Ala Ile Glu Glu Ile Asn Ser
    50                  55                  60

Ser Pro Ala Leu Leu Pro Asn Leu Thr Leu Gly Tyr Arg Ile Phe Asp
65                  70                  75                  80

Thr Cys Asn Thr Val Ser Lys Ala Leu Glu Ala Thr Leu Ser Phe Val
                85                  90                  95

Ala Gln Asn Lys Ile Asp Ser Leu Asn Leu Asp Glu Phe Cys Asn Cys
                100                 105                 110

Ser Glu His Ile Pro Ser Thr Ile Ala Val Val Gly Ala Thr Gly Ser
            115                 120                 125

Gly Val Ser Thr Ala Val Ala Asn Leu Leu Gly Leu Phe Tyr Ile Pro
    130                 135                 140

Gln Val Ser Tyr Ala Ser Ser Ser Arg Leu Leu Ser Asn Lys Asn Gln
145                 150                 155                 160

Phe Lys Ser Phe Leu Arg Thr Ile Pro Asn Asp Glu His Gln Ala Thr
                165                 170                 175

Ala Met Ala Asp Ile Ile Glu Tyr Phe Arg Trp Asn Trp Val Gly Thr
            180                 185                 190

Ile Ala Ala Asp Asp Tyr Gly Arg Pro Gly Ile Glu Lys Phe Arg
    195                 200                 205

Glu Glu Ala Glu Glu Arg Asp Ile Cys Ile Asp Phe Ser Glu Leu Ile
    210                 215                 220

Ser Gln Tyr Ser Asp Glu Glu Ile Gln His Val Val Glu Val Ile
225                 230                 235                 240

Gln Asn Ser Thr Ala Lys Val Ile Val Val Phe Ser Ser Gly Pro Asp
                245                 250                 255

Leu Glu Pro Leu Ile Lys Glu Ile Val Arg Arg Asn Ile Thr Gly Lys
                260                 265                 270

Ile Trp Leu Ala Ser Glu Ala Trp Ala Ser Ser Ser Leu Ile Ala Met
    275                 280                 285

Pro Gln Tyr Phe His Val Val Gly Gly Thr Ile Gly Phe Ala Leu Lys
    290                 295                 300

Ala Gly Gln Ile Pro Gly Phe Arg Glu Phe Leu Lys Lys Val His Pro
305                 310                 315                 320

Arg Lys Ser Val His Asn Gly Phe Ala Lys Glu Phe Trp Glu Glu Thr
                325                 330                 335

Phe Asn Cys His Leu Gln Glu Gly Ala Lys Gly Pro Leu Pro Val Asp
                340                 345                 350

Tyr Lys Asp Asp Asp Lys Thr Phe Leu Arg Gly His Glu Glu Ser
            355                 360                 365

Gly Asp Arg Phe Ser Asn Ser Ser Thr Ala Phe Arg Pro Leu Cys Thr
    370                 375                 380

Gly Asp Glu Asn Ile Ser Ser Val Glu Thr Pro Tyr Ile Asp Tyr Thr
385                 390                 395                 400

His Leu Arg Ile Ser Tyr Asn Val Tyr Leu Ala Val Tyr Ser Ile Ala
                405                 410                 415

His Ala Leu Gln Asp Ile Tyr Thr Cys Leu Pro Gly Arg Gly Leu Phe
            420                 425                 430

Thr Asn Gly Ser Cys Ala Asp Ile Lys Lys Val Glu Ala Trp Gln Val
            435                 440                 445

Leu Lys His Leu Arg His Leu Asn Phe Thr Asn Met Gly Glu Gln
    450                 455                 460
```

```
Val Thr Phe Asp Glu Cys Gly Asp Leu Val Gly Asn Tyr Ser Ile Ile
465                 470                 475                 480

Asn Trp His Leu Ser Pro Glu Asp Gly Ser Ile Val Phe Lys Glu Val
            485                 490                 495

Gly Tyr Tyr Asn Val Tyr Ala Lys Lys Gly Glu Arg Leu Phe Ile Asn
        500                 505                 510

Glu Glu Lys Ile Leu Trp Ser Gly Phe Ser Arg Glu Val Pro Phe Ser
            515                 520                 525

Asn Cys Ser Arg Asp Cys Leu Ala Gly Thr Arg Lys Gly Ile Ile Glu
        530                 535                 540

Gly Glu Pro Thr Cys Cys Phe Glu Cys Val Glu Cys Pro Asp Gly Glu
545                 550                 555                 560

Tyr Ser Asp Glu Thr Asp Ala Ser Ala Cys Asn Lys Cys Pro Asp Asp
            565                 570                 575

Phe Trp Ser Asn Glu Asn His Thr Ser Cys Ile Ala Lys Glu Ile Glu
        580                 585                 590

Phe Leu Ser Trp Thr Glu Pro Phe
        595                 600

<210> SEQ ID NO 3
<211> LENGTH: 169
<212> TYPE: PRT
<213> ORGANISM: Artificial Sequence
<220> FEATURE:
<223> OTHER INFORMATION: ECD subdomain 1 of CaSR (amino acids 132-300 of
      SEQ ID NO: 1)

<400> SEQUENCE: 3

Ser Glu His Ile Pro Ser Thr Ile Ala Val Val Gly Ala Thr Gly Ser
1               5                   10                  15

Gly Val Ser Thr Ala Val Ala Asn Leu Leu Gly Leu Phe Tyr Ile Pro
            20                  25                  30

Gln Val Ser Tyr Ala Ser Ser Arg Leu Leu Ser Asn Lys Asn Gln
        35                  40                  45

Phe Lys Ser Phe Leu Arg Thr Ile Pro Asn Asp Glu His Gln Ala Thr
50                  55                  60

Ala Met Ala Asp Ile Ile Glu Tyr Phe Arg Trp Asn Trp Val Gly Thr
65                  70                  75                  80

Ile Ala Ala Asp Asp Asp Tyr Gly Arg Pro Gly Ile Glu Lys Phe Arg
                85                  90                  95

Glu Glu Ala Glu Glu Arg Asp Ile Cys Ile Asp Phe Ser Glu Leu Ile
            100                 105                 110

Ser Gln Tyr Ser Asp Glu Glu Ile Gln His Val Val Glu Val Ile
        115                 120                 125

Gln Asn Ser Thr Ala Lys Val Ile Val Val Phe Ser Ser Gly Pro Asp
        130                 135                 140

Leu Glu Pro Leu Ile Lys Glu Ile Val Arg Arg Asn Ile Thr Gly Lys
145                 150                 155                 160

Ile Trp Leu Ala Ser Glu Ala Trp Ala
                165

<210> SEQ ID NO 4
<211> LENGTH: 140
<212> TYPE: PRT
<213> ORGANISM: Artificial Sequence
<220> FEATURE:
<223> OTHER INFORMATION: ECD subdomain 2 of CaSR (amino acids 185-324 of
      SEQ ID NO: 1)
```

<400> SEQUENCE: 4

```
Arg Thr Ile Pro Asn Asp Glu His Gln Ala Thr Ala Met Ala Asp Ile
1               5                   10                  15

Ile Glu Tyr Phe Arg Trp Asn Trp Val Gly Thr Ile Ala Ala Asp Asp
            20                  25                  30

Asp Tyr Gly Arg Pro Gly Ile Glu Lys Phe Arg Glu Glu Ala Glu Glu
        35                  40                  45

Arg Asp Ile Cys Ile Asp Phe Ser Glu Leu Ile Ser Gln Tyr Ser Asp
50                  55                  60

Glu Glu Glu Ile Gln His Val Val Glu Val Ile Gln Asn Ser Thr Ala
65                  70                  75                  80

Lys Val Ile Val Val Phe Ser Ser Gly Pro Asp Leu Glu Pro Leu Ile
                85                  90                  95

Lys Glu Ile Val Arg Arg Asn Ile Thr Gly Lys Ile Trp Leu Ala Ser
            100                 105                 110

Glu Ala Trp Ala Ser Ser Ser Leu Ile Ala Met Pro Gln Tyr Phe His
        115                 120                 125

Val Val Gly Gly Thr Ile Gly Phe Ala Leu Lys Ala
    130                 135                 140
```

<210> SEQ ID NO 5
<211> LENGTH: 106
<212> TYPE: PRT
<213> ORGANISM: Artificial Sequence
<220> FEATURE:
<223> OTHER INFORMATION: ECD subdomain 3 of human CaSR (amino acids 340-445 of SEQ ID NO: 1)

<400> SEQUENCE: 5

```
Arg Lys Ser Val His Asn Gly Phe Ala Lys Glu Phe Trp Glu Glu Thr
1               5                   10                  15

Phe Asn Cys His Leu Gln Glu Gly Ala Lys Gly Pro Leu Pro Val Asp
            20                  25                  30

Thr Phe Leu Arg Gly His Glu Glu Ser Gly Asp Arg Phe Ser Asn Ser
        35                  40                  45

Ser Thr Ala Phe Arg Pro Leu Cys Thr Gly Asp Glu Asn Ile Ser Ser
50                  55                  60

Val Glu Thr Pro Tyr Ile Asp Tyr Thr His Leu Arg Ile Ser Tyr Asn
65                  70                  75                  80

Val Tyr Leu Ala Val Tyr Ser Ile Ala His Ala Leu Gln Asp Ile Tyr
                85                  90                  95

Thr Cys Leu Pro Gly Arg Gly Leu Phe Thr
            100                 105
```

<210> SEQ ID NO 6
<211> LENGTH: 84
<212> TYPE: PRT
<213> ORGANISM: Artificial Sequence
<220> FEATURE:
<223> OTHER INFORMATION: human CaSR systeine rich domain

<400> SEQUENCE: 6

```
Leu Trp Ser Gly Phe Ser Arg Glu Val Pro Phe Ser Asn Cys Ser Arg
1               5                   10                  15

Asp Cys Leu Ala Gly Thr Arg Lys Gly Ile Ile Glu Gly Glu Pro Thr
            20                  25                  30

Cys Cys Phe Glu Cys Val Glu Cys Pro Asp Gly Glu Tyr Ser Asp Glu
```

```
                35                  40                  45
Thr Asp Ala Ser Ala Cys Asn Lys Cys Pro Asp Asp Phe Trp Ser Asn
 50                  55                  60

Glu Asn His Thr Ser Cys Ile Ala Lys Glu Ile Glu Phe Leu Ser Trp
 65                  70                  75                  80

Thr Glu Pro Phe

<210> SEQ ID NO 7
<211> LENGTH: 688
<212> TYPE: PRT
<213> ORGANISM: Artificial Sequence
<220> FEATURE:
<223> OTHER INFORMATION: Shark CaSR ECD

<400> SEQUENCE: 7

Met Val Phe Pro Ser Pro Phe Gly Pro Cys Cys Gln Leu Val Leu Arg
 1               5                  10                  15

Trp Lys Thr Ser Lys Glu Asn Arg Cys Ser Ser Leu Lys Val Ser Thr
                20                  25                  30

Thr Glu Ser Ala Pro Thr Ile Thr Glu Thr Ser Lys Lys Ala Gln Thr
                35                  40                  45

Phe Val Ser Lys Leu Thr Leu Val Glu Ala Glu Gln Ser Asp Leu Leu
 50                  55                  60

Lys Ala Leu Gly Glu Glu Asp Cys Thr Met Gly Gly His His Tyr Gly
 65                  70                  75                  80

Leu Leu Ile Leu Gly Phe Thr Leu Leu Gln Ser Tyr Cys Val Ser Glu
                85                  90                  95

Tyr Gly Pro Asn Gln Arg Ala Gln Lys Lys Gly Asp Ile Ile Leu Gly
                100                 105                 110

Gly Leu Phe Pro Ile His Phe Gly Val Thr Ala Lys Asp Gln Asp Leu
                115                 120                 125

Lys Ser Arg Pro Glu Met Thr Lys Cys Phe Arg Tyr Asn Phe Arg Gly
130                 135                 140

Phe Arg Trp Leu Gln Ala Met Ile Phe Ala Ile Glu Glu Ile Asn Asn
145                 150                 155                 160

Ser Met Ala Phe Leu Pro Asn Ile Thr Leu Gly Tyr Arg Ile Phe Asp
                165                 170                 175

Thr Cys Asn Thr Val Ser Lys Ala Leu Glu Ala Thr Leu Ser Phe Val
                180                 185                 190

Ala Gln Asn Lys Ile Asp Ser Leu Asn Leu Asp Glu Phe Cys Asn Cys
                195                 200                 205

Ser Asp His Ile Pro Ser Thr Ile Ala Val Val Gly Ala Thr Gly Ser
210                 215                 220

Gly Ile Ser Thr Ala Val Ala Asn Leu Leu Gly Leu Phe Tyr Ile Pro
225                 230                 235                 240

Gln Val Ser Tyr Ala Ser Ser Ser Arg Leu Leu Ser Asn Lys Asn Gln
                245                 250                 255

Tyr Lys Ser Phe Leu Arg Thr Ile Pro Asn Asp Glu Gln Gln Ala Thr
                260                 265                 270

Ala Met Ala Asp Ile Ile Gln His Phe Gln Trp Asn Trp Val Gly Thr
                275                 280                 285

Leu Ala Ala Asp Asp Asp Tyr Gly Arg Pro Gly Ile Glu Lys Phe Arg
290                 295                 300

Glu Glu Ala Glu Glu Arg Asp Ile Cys Ile Asp Phe Ser Glu Leu Ile
305                 310                 315                 320
```

Ser Gln Tyr Tyr Thr Gln Glu Glu Leu Gln His Val Ala Glu Val Ile
            325                 330                 335

Gln Asn Ser Thr Ala Lys Val Ile Val Val Phe Ser Ser Gly Pro Asp
        340                 345                 350

Leu Glu Pro Ile Ile Gln Glu Ile Val Arg Arg Asn Ile Thr Gly Arg
    355                 360                 365

Ile Trp Leu Ala Ser Glu Ala Trp Ala Ser Ser Leu Ile Ala Lys
370                 375                 380

Pro Glu Tyr Phe His Val Val Gly Gly Thr Ile Gly Phe Ala Leu Arg
385                 390                 395                 400

Ala Gly His Ile Pro Gly Phe Tyr Glu Phe Leu Gln Arg Val His Pro
                405                 410                 415

Ser Arg Ser Ser Asp Asn Gly Phe Val Lys Glu Phe Trp Glu Glu Thr
                420                 425                 430

Phe Lys Cys Tyr Leu Thr Glu Lys Ser Leu Thr Gln Leu Lys Gln Ser
            435                 440                 445

Lys Thr Pro Gly His Asp Gly Ser Thr Val Val Gly Asn Ile Thr Ser
        450                 455                 460

Ser Lys Leu Leu Pro Pro Cys Thr Gly Asp Glu Asn Ile Met Ser Val
465                 470                 475                 480

Glu Thr Pro Tyr Leu Asp Tyr Thr His Met Arg Ile Ser Tyr Asn Val
                485                 490                 495

Tyr Met Ala Val Tyr Ser Ile Ala His Ala Leu Gln Asp Ile Tyr Thr
            500                 505                 510

Cys Thr Pro Gly Lys Gly Ile Phe Glu Asn Gly Ser Cys Ala Asp Ile
        515                 520                 525

Lys Lys Val Glu Ala Trp Gln Val Leu Lys His Leu Lys His Leu Lys
530                 535                 540

Phe Thr Asn Ser Met Gly Glu Gln Val Asp Phe Asp Asp Gln Gly Asp
545                 550                 555                 560

Leu Lys Gly Asn Tyr Thr Ile Ile Asn Trp Gln Leu Ser Ser Glu Asp
                565                 570                 575

Gln Ser Val Val Phe Gln Glu Val Gly Asn Tyr Asn Ala Tyr Ala Lys
            580                 585                 590

Pro Gly Glu Arg Leu Tyr Ile Asn Glu Ser Lys Val Leu Trp Ser Gly
        595                 600                 605

Phe Ser Lys Val Val Pro Phe Ser Asn Cys Thr His Asp Cys Ile Pro
610                 615                 620

Gly Thr Arg Lys Gly Ile Ile Glu Gly Glu Pro Thr Cys Cys Phe Glu
625                 630                 635                 640

Cys Val Ser Cys Ala Glu Gly Glu Tyr Ser Asp Glu Asn Asp Ala Ser
                645                 650                 655

Ala Cys Thr Lys Cys Pro Asn Asp Phe Trp Ser Asn Glu Asn His Thr
            660                 665                 670

Tyr Cys Ile Glu Lys Glu Ile Glu Tyr Leu Ser Trp Thr Glu Pro Phe
        675                 680                 685

<210> SEQ ID NO 8
<211> LENGTH: 601
<212> TYPE: PRT
<213> ORGANISM: Artificial Sequence
<220> FEATURE:
<223> OTHER INFORMATION: Zebrafish CaSR ECD

<400> SEQUENCE: 8

```
Met Arg Phe His Leu Lys Phe Tyr Leu His Tyr Leu Val Leu Leu Gly
1               5                   10                  15

Ser Ser Cys Val Ile Ser Thr Tyr Gly Pro Asn Gln Arg Ala Gln Lys
            20                  25                  30

Thr Gly Asp Ile Leu Leu Gly Gly Leu Phe Pro Met His Phe Gly Val
        35                  40                  45

Ala Ser Lys Asp Gln Asp Leu Ala Ala Arg Pro Glu Ser Thr Glu Cys
    50                  55                  60

Val Arg Tyr Asn Phe Arg Gly Phe Arg Trp Leu Gln Ser Met Ile Phe
65                  70                  75                  80

Ala Ile Glu Glu Ile Asn Asn Ser Ser Thr Leu Leu Pro Asn Ile Thr
                85                  90                  95

Leu Gly Tyr Arg Ile Phe Asp Thr Cys Asn Thr Val Ser Lys Ala Leu
                100                 105                 110

Glu Ala Ser Leu Ser Phe Val Ala Gln Asn Lys Ile Asp Ser Leu Asn
            115                 120                 125

Leu Asp Glu Phe Cys Asn Cys Thr Gly Asn Ile Pro Ser Thr Ile Ala
        130                 135                 140

Val Val Gly Ala Ser Gly Ser Ala Val Ser Thr Ala Val Ala Asp Leu
145                 150                 155                 160

Leu Gly Leu Phe Tyr Ile Pro Gln Ile Ser Tyr Ala Ser Ser Ser Arg
                165                 170                 175

Leu Leu Ser Asn Lys Asn Gln Tyr Lys Ser Phe Met Arg Thr Ile Pro
            180                 185                 190

Thr Asp Glu Tyr Gln Ala Ile Ala Met Ala Ala Ile Glu His Phe
        195                 200                 205

Gln Trp Asn Trp Val Ile Ala Ile Ala Ser Asp Asp Glu Tyr Gly Arg
210                 215                 220

Pro Gly Ile Glu Lys Phe Glu Asn Glu Met Phe His Arg Asp Ile Cys
225                 230                 235                 240

Ile Asp Leu Asn Val Leu Ile Ser Gln Tyr Val Asp Glu Ala Glu Ile
                245                 250                 255

Arg Arg Leu Ala Asp Arg Ile Gln Asn Ser Ser Ala Lys Val Ile Val
            260                 265                 270

Val Phe Ala Ser Gly Pro Asp Ile Glu Pro Leu Val Lys Glu Met Val
        275                 280                 285

Arg Arg Asn Ile Thr Asp Arg Val Trp Leu Ala Ser Glu Ala Trp Ala
290                 295                 300

Ser Ser Ser Leu Val Ala Lys Pro Glu Tyr Leu Asp Val Met Gly Gly
305                 310                 315                 320

Thr Ile Gly Phe Ala Leu Arg Ala Gly His Ile Pro Gly Phe Lys Asp
                325                 330                 335

Phe Leu Gln Gln Val His Pro Lys Lys Ser Ser His Asn Glu Phe Val
            340                 345                 350

Arg Glu Phe Trp Glu Glu Thr Phe Asn Cys Tyr Leu Glu Asp Ser Pro
        355                 360                 365

Arg Asn Ala Asp Ser Glu Asn Gly Ser Thr Ser Phe Arg Pro Leu Cys
370                 375                 380

Thr Gly Glu Glu Asp Ile Ala Ser Val Glu Thr Pro Tyr Leu Asp Tyr
385                 390                 395                 400

Thr His Leu Arg Ile Ser Tyr Asn Val Tyr Val Ala Tyr Ala Ile
                405                 410                 415
```

-continued

Ala Gln Ala Leu Gln Asp Ile Leu Thr Cys Thr Pro Gly Lys Gly Leu
            420                 425                 430

Phe Ser Asn Gly Ser Cys Ala Asp Ile Arg Lys Val Glu Ala Trp Gln
        435                 440                 445

Val Leu Lys Gln Leu Arg His Leu Asn Phe Ile Asp Ser Met Gly Glu
    450                 455                 460

Arg Val Arg Phe Asp Asn Gly Ser Glu Leu Ser Ala Asn Tyr Thr Ile
465                 470                 475                 480

Ile Asn Trp His Arg Ser Pro Glu Asp Gly Ser Val Val Phe Lys Glu
                485                 490                 495

Val Gly Tyr Tyr Ser Ile His Asn Lys Asn Val Ala Lys Leu Ser Ile
            500                 505                 510

Asp Lys Ser Lys Ile Leu Trp Asn Gly Arg Leu Thr Glu Val Pro Phe
        515                 520                 525

Ser Asn Cys Ser Val Glu Cys Glu Pro Gly Thr Arg Lys Gly Ile Ile
    530                 535                 540

Asp Gly Glu Pro Thr Cys Cys Phe Glu Cys Thr Glu Cys Ser Asp Gly
545                 550                 555                 560

Glu Tyr Ser Asp His Lys Asp Ala Ser Phe Cys Val Lys Cys Pro Asn
                565                 570                 575

Asn Ser Trp Ser Asn Gly Asn His Thr Ser Cys Phe Leu Lys Gln Ile
            580                 585                 590

Glu Phe Leu Ser Trp Thr Glu Pro Phe
            595                 600

<210> SEQ ID NO 9
<211> LENGTH: 597
<212> TYPE: PRT
<213> ORGANISM: Artificial Sequence
<220> FEATURE:
<223> OTHER INFORMATION: Salmon CaSR ECD

<400> SEQUENCE: 9

Met Arg Phe Tyr Leu Tyr Tyr Leu Val Leu Leu Gly Phe Ser Ser Val
1               5                   10                  15

Ile Ser Thr Tyr Gly Pro His Gln Arg Ala Gln Lys Thr Gly Asp Ile
            20                  25                  30

Leu Leu Gly Gly Leu Phe Pro Met His Phe Gly Val Thr Ser Lys Asp
        35                  40                  45

Gln Asp Leu Ala Ala Arg Pro Glu Ser Thr Glu Cys Val Arg Tyr Asn
    50                  55                  60

Phe Arg Gly Phe Arg Trp Leu Gln Ala Met Ile Phe Ala Ile Glu Glu
65                  70                  75                  80

Ile Asn Asn Ser Ser Thr Leu Leu Pro Asn Ile Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Thr Asp His Ile Pro Ser Thr Ile Ala Val Val Gly Ala
    130                 135                 140

Ser Gly Ser Ala Val Ser Thr Ala Val Ala Asn Leu Leu Gly Leu Phe
145                 150                 155                 160

Tyr Ile Pro Gln Ile Ser Tyr Ala Ser Ser Ser Arg Leu Leu Ser Asn
                165                 170                 175

```
Lys Asn Gln Phe Lys Ser Phe Met Arg Thr Ile Pro Thr Asp Glu His
                180                 185                 190

Gln Ala Thr Ala Met Ala Asp Ile Ile Asp Tyr Phe Gln Trp Asn Trp
            195                 200                 205

Val Ile Ala Val Ala Ser Asp Asp Glu Tyr Gly Arg Pro Gly Ile Glu
        210                 215                 220

Lys Phe Glu Lys Glu Met Glu Glu Arg Asp Ile Cys Ile His Leu Ser
225                 230                 235                 240

Glu Leu Ile Ser Gln Tyr Phe Glu Glu Trp Gln Ile Gln Gly Leu Val
                245                 250                 255

Asp Arg Ile Glu Asn Ser Ser Ala Lys Val Ile Val Phe Ala Ser
            260                 265                 270

Gly Pro Asp Ile Glu Pro Leu Ile Lys Glu Met Val Arg Arg Asn Ile
        275                 280                 285

Thr Asp Arg Ile Trp Leu Ala Ser Glu Ala Trp Ala Thr Thr Ser Leu
        290                 295                 300

Ile Ala Lys Pro Glu Tyr Leu Asp Val Val Gly Thr Ile Gly Phe
305                 310                 315                 320

Ala Leu Arg Ala Gly Glu Ile Pro Gly Phe Lys Asp Phe Leu Gln Glu
                325                 330                 335

Val Thr Pro Lys Lys Ser Ser His Asn Glu Phe Val Arg Glu Phe Trp
            340                 345                 350

Glu Glu Thr Phe Asn Cys Tyr Leu Glu Asp Ser Gln Arg Leu Arg Asp
        355                 360                 365

Ser Glu Asn Gly Ser Thr Ser Phe Arg Pro Leu Cys Thr Gly Glu Glu
370                 375                 380

Asp Ile Met Gly Ala Glu Thr Pro Tyr Leu Asp Tyr Thr His Leu Arg
385                 390                 395                 400

Ile Ser Tyr Asn Val Tyr Val Ala Val His Ser Ile Ala Gln Ala Leu
                405                 410                 415

Gln Asp Ile Leu Thr Cys Ile Pro Gly Arg Gly Leu Phe Ser Asn Asn
            420                 425                 430

Ser Cys Ala Asp Ile Lys Lys Ile Glu Ala Trp Gln Val Leu Lys Gln
        435                 440                 445

Leu Arg His Leu Asn Phe Ser Asn Ser Met Gly Glu Lys Val His Phe
        450                 455                 460

Asp Glu Asn Ala Asp Pro Ser Gly Asn Tyr Thr Ile Ile Asn Trp His
465                 470                 475                 480

Arg Ser Pro Glu Asp Gly Ser Val Val Phe Glu Glu Val Gly Phe Tyr
                485                 490                 495

Asn Met Arg Ala Lys Arg Gly Val Gln Leu Phe Ile Asp Asn Thr Lys
            500                 505                 510

Ile Leu Trp Asn Gly Tyr Asn Thr Glu Val Pro Phe Ser Asn Cys Ser
        515                 520                 525

Glu Asp Cys Glu Pro Gly Thr Arg Lys Gly Ile Ile Glu Ser Met Pro
        530                 535                 540

Thr Cys Cys Phe Glu Cys Thr Glu Cys Ser Glu Gly Glu Tyr Ser Asp
545                 550                 555                 560

His Lys Asp Ala Ser Val Cys Thr Lys Cys Pro Asn Asp Ser Trp Ser
                565                 570                 575

Asn Glu Asn His Thr Ser Cys Phe Leu Lys Glu Ile Glu Phe Leu Ser
            580                 585                 590

Trp Thr Glu Pro Phe
```

```
                595

<210> SEQ ID NO 10
<211> LENGTH: 611
<212> TYPE: PRT
<213> ORGANISM: Artificial Sequence
<220> FEATURE:
<223> OTHER INFORMATION: Chicken CaSR ECD

<400> SEQUENCE: 10

Met Thr Leu Tyr Ser Cys Cys Leu Ile Leu Leu Phe Thr Trp Asn
1               5                   10                  15

Thr Ala Ala Tyr Gly Pro Asn Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Asn Ser Pro Asn Leu Leu Pro Asn Met Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Tyr Gly Arg Pro Gly Ile Glu
    210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln Gln Val Val
                245                 250                 255

Glu Val Ile Gln Asn Ser Thr Ala Arg Val Ile Val Phe Ser Ser
            260                 265                 270

Gly Pro Asp Leu Glu Pro Leu Ile Lys Glu Ile Val Arg Arg Asn Ile
        275                 280                 285

Thr Gly Lys Ile Trp Leu Ala Ser Glu Ala Trp Ala Ser Ser Ser Leu
    290                 295                 300

Ile Ala Met Pro Glu Phe Phe Arg Val Ile Gly Ser Thr Ile Gly Phe
305                 310                 315                 320

Ala Leu Lys Ala Gly Gln Ile Pro Gly Phe Arg Glu Phe Leu Gln Lys
                325                 330                 335

Val His Pro Lys Lys Ser Ala Asn Asn Gly Phe Ala Lys Glu Phe Trp
            340                 345                 350

Glu Glu Thr Phe Asn Cys Tyr Leu Pro Ser Glu Ser Lys Asn Ser Pro
```

```
            355                 360                 365
Ala Ser Ala Ser Phe His Lys Ala His Glu Glu Gly Leu Gly Ala Gly
    370                 375                 380

Asn Gly Thr Ala Ala Phe Arg Pro Pro Cys Thr Gly Asp Glu Asn Ile
385                 390                 395                 400

Thr Ser Val Glu Thr Pro Tyr Met Asp Phe Thr His Leu Arg Ile Ser
                405                 410                 415

Tyr Asn Val Tyr Leu Ala Val Tyr Ser Ile Ala His Ala Leu Gln Asp
            420                 425                 430

Ile Tyr Thr Cys Thr Pro Gly Lys Gly Leu Phe Thr Asn Gly Ser Cys
        435                 440                 445

Ala Asp Ile Lys Lys Val Glu Ala Trp Gln Val Leu Lys His Leu Arg
    450                 455                 460

His Leu Asn Phe Thr Ser Asn Met Gly Glu Gln Val Asp Phe Asp Glu
465                 470                 475                 480

Phe Gly Asp Leu Val Gly Asn Tyr Ser Ile Ile Asn Trp His Leu Ser
                485                 490                 495

Pro Glu Asp Gly Ser Val Val Phe Glu Glu Val Gly His Tyr Asn Val
            500                 505                 510

Tyr Ala Lys Lys Gly Glu Arg Leu Phe Ile Asn Glu Asn Lys Ile Leu
        515                 520                 525

Trp Ser Gly Phe Ser Lys Glu Val Pro Phe Ser Asn Cys Ser Arg Asp
    530                 535                 540

Cys Leu Pro Gly Thr Arg Lys Gly Ile Ile Glu Gly Glu Pro Thr Cys
545                 550                 555                 560

Cys Phe Glu Cys Val Asp Cys Pro Asp Gly Glu Tyr Ser Asp Glu Thr
                565                 570                 575

Asp Ala Ser Ala Cys Asp Lys Cys Pro Glu Asp Tyr Trp Ser Asn Glu
            580                 585                 590

Asn His Thr Ser Cys Ile Pro Lys Gln Ile Glu Phe Leu Ser Trp Thr
        595                 600                 605

Glu Pro Phe
    610

<210> SEQ ID NO 11
<211> LENGTH: 612
<212> TYPE: PRT
<213> ORGANISM: Artificial Sequence
<220> FEATURE:
<223> OTHER INFORMATION: Mouse CaSR ECD

<400> SEQUENCE: 11

Met Ala Trp Phe Gly Tyr Cys Leu Ala Leu Leu Ala Leu Thr Trp His
1               5                   10                  15

Ser Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ser Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Met Thr Leu Gly Tyr Arg
                85                  90                  95

Ile Phe Asp Thr Cys Asn Thr Val Ser Lys Ala Leu Glu Ala Thr Leu
```

```
              100             105             110
    Ser Phe Val Ala Gln Asn Lys Ile Asp Ser Leu Asn Leu Asp Glu Phe
            115                 120                 125

Cys Asn Cys Ser Glu His Ile Pro Ser Thr Ile Ala Val Val Gly Ala
            130                 135                 140

Thr Gly Ser Gly Val Ser Thr Ala Val Ala Asn Leu Leu Gly Leu Phe
    145                 150                 155                 160

Tyr Ile Pro Gln Val Ser Tyr Ala Ser Ser Arg Leu Leu Ser Asn
                        165                 170                 175

Lys Asn Gln Phe Lys Ser Phe Leu Arg Thr Ile Pro Asn Asp Glu His
                    180                 185                 190

Gln Ala Thr Ala Met Ala Asp Ile Ile Glu Tyr Phe Arg Trp Asn Trp
                195                 200                 205

Val Gly Thr Ile Ala Ala Asp Asp Tyr Gly Arg Pro Gly Ile Glu
                210                 215                 220

Lys Phe Arg Glu Glu Ala Glu Glu Arg Asp Ile Cys Ile Asp Phe Ser
    225                 230                 235                 240

Glu Leu Ile Ser Gln Tyr Ser Asp Glu Glu Ile Gln Gln Val Val
                        245                 250                 255

Glu Val Ile Gln Asn Ser Thr Ala Lys Val Ile Val Phe Ser Ser
                    260                 265                 270

Gly Pro Asp Leu Glu Pro Leu Ile Lys Glu Ile Val Arg Arg Asn Ile
                    275                 280                 285

Thr Gly Arg Ile Trp Leu Ala Ser Glu Ala Trp Ala Ser Ser Ser Leu
                290                 295                 300

Ile Ala Met Pro Glu Tyr Phe His Val Val Gly Thr Ile Gly Phe
    305                 310                 315                 320

Gly Leu Lys Ala Gly Gln Ile Pro Gly Phe Arg Glu Phe Leu Gln Lys
                    325                 330                 335

Val His Pro Arg Lys Ser Val His Asn Gly Phe Ala Lys Glu Phe Trp
                340                 345                 350

Glu Glu Thr Phe Asn Cys His Leu Gln Asp Gly Ala Lys Gly Pro Leu
                355                 360                 365

Pro Val Asp Thr Phe Val Arg Ser His Glu Glu Gly Asn Arg Leu
                370                 375                 380

Leu Asn Ser Ser Thr Ala Phe Arg Pro Leu Cys Thr Gly Asp Glu Asn
    385                 390                 395                 400

Ile Asn Ser Val Glu Thr Pro Tyr Met Asp Tyr Glu His Leu Arg Ile
                    405                 410                 415

Ser Tyr Asn Val Tyr Leu Ala Val Tyr Ser Ile Ala His Ala Leu Gln
                420                 425                 430

Asp Ile Tyr Thr Cys Leu Pro Gly Arg Gly Leu Phe Thr Asn Gly Ser
                435                 440                 445

Cys Ala Asp Ile Lys Lys Val Glu Ala Trp Gln Val Leu Lys His Leu
    450                 455                 460

Arg His Leu Asn Phe Thr Asn Asn Met Gly Glu Gln Val Thr Phe Asp
    465                 470                 475                 480

Glu Cys Gly Asp Leu Val Gly Asn Tyr Ser Ile Ile Asn Trp His Leu
                    485                 490                 495

Ser Pro Glu Asp Gly Ser Ile Val Phe Lys Glu Val Gly Tyr Tyr Asn
                500                 505                 510

Val Tyr Ala Lys Lys Gly Glu Arg Leu Phe Ile Asn Glu Gly Lys Ile
                515                 520                 525
```

```
Leu Trp Ser Gly Phe Ser Arg Glu Val Pro Phe Ser Asn Cys Ser Arg
        530                 535                 540

Asp Cys Gln Ala Gly Thr Arg Lys Gly Ile Ile Glu Gly Glu Pro Thr
545                 550                 555                 560

Cys Cys Phe Glu Cys Ala Glu Cys Pro Asp Gly Glu Tyr Ser Gly Glu
                565                 570                 575

Thr Asp Ala Ser Ala Cys Asp Lys Cys Pro Asp Asp Phe Trp Ser Asn
                580                 585                 590

Glu Asn His Thr Ser Cys Ile Ala Lys Glu Ile Glu Phe Leu Ala Trp
            595                 600                 605

Thr Glu Pro Phe
        610

<210> SEQ ID NO 12
<211> LENGTH: 612
<212> TYPE: PRT
<213> ORGANISM: Artificial Sequence
<220> FEATURE:
<223> OTHER INFORMATION: Rat CaSR ECD

<400> SEQUENCE: 12

Met Ala Ser Tyr Ser Cys Cys Leu Ala Leu Leu Ala Leu Ala Trp His
1               5                   10                  15

Ser Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
50                  55                  60

Phe Arg Gly Phe Arg Trp Leu Gln Ala Met Ile Phe Ala Ile Glu Glu
65                  70                  75                  80

Ile Asn Ser Ser Pro Ser Leu Leu Pro Asn Met Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                165                 170                 175

Lys Asn Gln Tyr Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Tyr Gly Arg Pro Gly Ile Glu
    210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln Gln Val Val
                245                 250                 255

Glu Val Ile Gln Asn Ser Thr Ala Lys Val Ile Val Val Phe Ser Ser
            260                 265                 270
```

Gly Pro Asp Leu Glu Pro Leu Ile Lys Glu Ile Val Arg Asn Ile
    275                 280                 285

Thr Gly Arg Ile Trp Leu Ala Ser Glu Ala Trp Ala Ser Ser Leu
    290                 295                 300

Ile Ala Met Pro Glu Tyr Phe His Val Gly Gly Thr Ile Gly Phe
305                 310                 315                 320

Gly Leu Lys Ala Gly Gln Ile Pro Gly Phe Arg Glu Phe Leu Gln Lys
                325                 330                 335

Val His Pro Arg Lys Ser Val His Asn Gly Phe Ala Lys Glu Phe Trp
            340                 345                 350

Glu Glu Thr Phe Asn Cys His Leu Gln Glu Gly Ala Lys Gly Pro Leu
                355                 360                 365

Pro Val Asp Thr Phe Val Arg Ser His Glu Glu Gly Gly Asn Arg Leu
    370                 375                 380

Leu Asn Ser Ser Thr Ala Phe Arg Pro Leu Cys Thr Gly Asp Glu Asn
385                 390                 395                 400

Ile Asn Ser Val Glu Thr Pro Tyr Met Asp Tyr Glu His Leu Arg Ile
                405                 410                 415

Ser Tyr Asn Val Tyr Leu Ala Val Tyr Ser Ile Ala His Ala Leu Gln
            420                 425                 430

Asp Ile Tyr Thr Cys Leu Pro Gly Arg Gly Leu Phe Thr Asn Gly Ser
        435                 440                 445

Cys Ala Asp Ile Lys Lys Val Glu Ala Trp Gln Val Leu Lys His Leu
450                 455                 460

Arg His Leu Asn Phe Thr Asn Asn Met Gly Glu Gln Val Thr Phe Asp
465                 470                 475                 480

Glu Cys Gly Asp Leu Val Gly Asn Tyr Ser Ile Ile Asn Trp His Leu
                485                 490                 495

Ser Pro Glu Asp Gly Ser Ile Val Phe Lys Glu Val Gly Tyr Tyr Asn
            500                 505                 510

Val Tyr Ala Lys Lys Gly Glu Arg Leu Phe Ile Asn Glu Glu Lys Ile
        515                 520                 525

Leu Trp Ser Gly Phe Ser Arg Glu Val Pro Phe Ser Asn Cys Ser Arg
    530                 535                 540

Asp Cys Gln Ala Gly Thr Arg Lys Gly Ile Ile Glu Gly Glu Pro Thr
545                 550                 555                 560

Cys Cys Phe Glu Cys Val Glu Cys Pro Asp Gly Glu Tyr Ser Gly Glu
                565                 570                 575

Thr Asp Ala Ser Ala Cys Asp Lys Cys Pro Asp Asp Phe Trp Ser Asn
            580                 585                 590

Glu Asn His Thr Ser Cys Ile Ala Lys Glu Ile Glu Phe Leu Ala Trp
        595                 600                 605

Thr Glu Pro Phe
    610

<210> SEQ ID NO 13
<211> LENGTH: 612
<212> TYPE: PRT
<213> ORGANISM: Artificial Sequence
<220> FEATURE:
<223> OTHER INFORMATION: human CasR ECD

<400> SEQUENCE: 13

Met Ala Phe Tyr Ser Cys Cys Trp Val Leu Leu Ala Leu Thr Trp His
1               5                   10                  15

```
Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Tyr Gly Arg Pro Gly Ile Glu
            210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln His Val Val
                245                 250                 255

Glu Val Ile Gln Asn Ser Thr Ala Lys Val Ile Val Phe Ser Ser
            260                 265                 270

Gly Pro Asp Leu Glu Pro Leu Ile Lys Glu Ile Val Arg Arg Asn Ile
        275                 280                 285

Thr Gly Lys Ile Trp Leu Ala Ser Glu Ala Trp Ala Ser Ser Ser Leu
290                 295                 300

Ile Ala Met Pro Gln Tyr Phe His Val Val Gly Thr Ile Gly Phe
305                 310                 315                 320

Ala Leu Lys Ala Gly Gln Ile Pro Gly Phe Arg Glu Phe Leu Lys Lys
                325                 330                 335

Val His Pro Arg Lys Ser Val Asn Gly Phe Ala Lys Glu Phe Trp
            340                 345                 350

Glu Glu Thr Phe Asn Cys His Leu Gln Glu Gly Ala Lys Gly Pro Leu
        355                 360                 365

Pro Val Asp Thr Phe Leu Arg Gly His Glu Glu Ser Gly Asp Arg Phe
370                 375                 380

Ser Asn Ser Ser Thr Ala Phe Arg Pro Leu Cys Thr Gly Asp Glu Asn
385                 390                 395                 400

Ile Ser Ser Val Glu Thr Pro Tyr Ile Asp Tyr Thr His Leu Arg Ile
                405                 410                 415

Ser Tyr Asn Val Tyr Leu Ala Val Tyr Ser Ile Ala His Ala Leu Gln
            420                 425                 430
```

```
Asp Ile Tyr Thr Cys Leu Pro Gly Arg Gly Leu Phe Thr Asn Gly Ser
            435                 440                 445

Cys Ala Asp Ile Lys Lys Val Glu Ala Trp Gln Val Leu Lys His Leu
450                 455                 460

Arg His Leu Asn Phe Thr Asn Asn Met Gly Glu Gln Val Thr Phe Asp
465                 470                 475                 480

Glu Cys Gly Asp Leu Val Gly Asn Tyr Ser Ile Ile Asn Trp His Leu
                485                 490                 495

Ser Pro Glu Asp Gly Ser Ile Val Phe Lys Glu Val Gly Tyr Tyr Asn
            500                 505                 510

Val Tyr Ala Lys Lys Gly Glu Arg Leu Phe Ile Asn Glu Glu Lys Ile
        515                 520                 525

Leu Trp Ser Gly Phe Ser Arg Glu Val Pro Phe Ser Asn Cys Ser Arg
530                 535                 540

Asp Cys Leu Ala Gly Thr Arg Lys Gly Ile Ile Glu Gly Glu Pro Thr
545                 550                 555                 560

Cys Cys Phe Glu Cys Val Glu Cys Pro Asp Gly Glu Tyr Ser Asp Glu
                565                 570                 575

Thr Asp Ala Ser Ala Cys Asn Lys Cys Pro Asp Asp Phe Trp Ser Asn
            580                 585                 590

Glu Asn His Thr Ser Cys Ile Ala Lys Glu Ile Glu Phe Leu Ser Trp
        595                 600                 605

Thr Glu Pro Phe
    610

<210> SEQ ID NO 14
<211> LENGTH: 622
<212> TYPE: PRT
<213> ORGANISM: Artificial Sequence
<220> FEATURE:
<223> OTHER INFORMATION: gibbon CaSR ECD

<400> SEQUENCE: 14

Met Ala Phe Tyr Ser Cys Cys Trp Val Leu Leu Ala Leu Thr Trp His
1               5                   10                  15

Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Ser Arg Leu Leu Ser Asn
                165                 170                 175
```

```
Lys Asn Gln Phe Lys Ser Phe Leu Arg Thr Ile Pro Asn Asp Glu His
                180                 185                 190

Gln Ala Thr Ala Met Ala Asp Ile Ile Glu Tyr Phe Arg Trp Asn Trp
            195                 200                 205

Val Gly Thr Ile Ala Ala Asp Asp Tyr Gly Arg Pro Gly Ile Glu
        210                 215                 220

Lys Phe Arg Glu Glu Ala Glu Arg Asp Ile Cys Ile Asp Phe Ser
225                 230                 235                 240

Glu Leu Ile Ser Gln Tyr Ser Asp Glu Glu Ile Gln His Val Val
                245                 250                 255

Glu Val Ile Gln Asn Ser Thr Ala Lys Val Ile Val Phe Ser Ser
                260                 265                 270

Gly Pro Asp Leu Glu Pro Leu Ile Lys Glu Ile Val Arg Arg Asn Ile
        275                 280                 285

Thr Gly Lys Ile Trp Leu Ala Ser Glu Ala Trp Ala Ser Ser Ser Leu
        290                 295                 300

Ile Ala Met Pro Gln Tyr Phe His Val Val Gly Gly Thr Ile Gly Phe
305                 310                 315                 320

Ala Leu Lys Ala Gly Gln Ile Pro Gly Phe Arg Glu Phe Leu Lys Lys
                325                 330                 335

Val His Pro Arg Lys Ser Val His Asn Gly Phe Ala Lys Glu Phe Trp
                340                 345                 350

Glu Glu Thr Phe Asn Cys His Leu Gln Gly Ala Lys Gly Pro Leu
                355                 360                 365

Pro Val Asp Thr Phe Leu Arg Gly His Glu Glu Ser Gly Gly Arg Phe
        370                 375                 380

Ser Asn Ser Ser Thr Ala Phe Arg Pro Leu Cys Thr Gly Asp Glu Asn
385                 390                 395                 400

Ile Ser Ser Val Glu Thr Pro Tyr Ile Asp Tyr Thr His Leu Arg Ile
                405                 410                 415

Ser Tyr Asn Val Tyr Leu Ala Val Tyr Ser Ile Ala His Ala Leu Gln
                420                 425                 430

Asp Ile Tyr Thr Cys Leu Pro Gly Arg Gly Leu Phe Thr Asn Gly Ser
            435                 440                 445

Cys Ala Asp Ile Lys Lys Val Glu Ala Trp Gln Val Leu Lys His Leu
450                 455                 460

Arg His Leu Asn Phe Thr Asn Asn Met Gly Glu Gln Val Thr Phe Asp
465                 470                 475                 480

Glu Cys Gly Asp Leu Val Gly Asn Tyr Ser Ile Ile Asn Trp His Leu
                485                 490                 495

Ser Ala Glu Asp Gly Ser Ile Val Phe Lys Glu Val Gly Tyr Tyr Asn
                500                 505                 510

Val Tyr Ala Lys Lys Gly Glu Arg Leu Phe Ile Asn Glu Glu Lys Ile
            515                 520                 525

Leu Trp Ser Gly Phe Ser Arg Glu Pro Leu Thr Phe Val Leu Ser Val
            530                 535                 540

Pro Gln Val Pro Phe Ser Asn Cys Ser Arg Asp Cys Leu Ala Gly Thr
545                 550                 555                 560

Arg Lys Gly Ile Ile Glu Gly Pro Thr Cys Cys Phe Glu Cys Val
                565                 570                 575

Glu Cys Pro Asp Gly Glu Tyr Ser Asp Glu Thr Asp Ala Ser Ala Cys
                580                 585                 590

Asn Lys Cys Pro Asp Asp Phe Trp Ser Asn Glu Asn His Thr Ser Cys
```

```
            595                 600                 605
Ile Ala Lys Glu Ile Glu Phe Leu Ser Trp Thr Glu Pro Phe
    610                 615                 620

<210> SEQ ID NO 15
<211> LENGTH: 612
<212> TYPE: PRT
<213> ORGANISM: Artificial Sequence
<220> FEATURE:
<223> OTHER INFORMATION: dog CaSR ECD

<400> SEQUENCE: 15

Met Ala Phe His Ser Cys Ser Leu Ile Leu Leu Ala Ile Thr Trp Cys
1               5                   10                  15

Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Met Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140

Thr Gly Ser Gly Ile Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Tyr Gly Arg Pro Gly Ile Glu
    210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln Gln Val Val
                245                 250                 255

Glu Val Ile Gln Asn Ser Thr Ala Lys Val Ile Val Phe Ser Ser
            260                 265                 270

Gly Pro Asp Leu Glu Pro Leu Ile Lys Glu Ile Val Arg Arg Asn Ile
        275                 280                 285

Thr Gly Arg Ile Trp Leu Ala Ser Glu Ala Trp Ala Ser Ser Ser Leu
    290                 295                 300

Ile Ala Met Pro Glu Tyr Phe His Val Val Gly Gly Thr Ile Gly Phe
305                 310                 315                 320

Ala Leu Lys Ala Gly Gln Ile Pro Gly Phe Arg Glu Phe Leu Gln Lys
                325                 330                 335

Val His Pro Arg Lys Ser Val His Asn Gly Phe Ala Lys Glu Phe Trp
```

```
                340                 345                 350
Glu Glu Thr Phe Asn Cys His Leu Gln Glu Gly Ala Lys Gly Pro Leu
        355                 360                 365

Ser Met Asp Thr Phe Leu Arg Gly His Glu Glu Gly Gly Gly Arg Ile
    370                 375                 380

Ser Asn Ser Ser Thr Ala Phe Arg Pro Leu Cys Thr Gly Asp Glu Asn
385                 390                 395                 400

Ile Ser Ser Val Glu Thr Pro Tyr Met Asp Tyr Thr His Leu Arg Ile
                405                 410                 415

Ser Tyr Asn Val Tyr Leu Ala Val Tyr Ser Ile Ala His Ala Leu Gln
            420                 425                 430

Asp Ile Tyr Thr Cys Leu Pro Gly Arg Gly Leu Phe Thr Asn Gly Ser
        435                 440                 445

Cys Ala Asp Ile Lys Lys Val Glu Ala Trp Gln Val Leu Lys His Leu
    450                 455                 460

Arg His Leu Asn Phe Thr Asn Asn Met Gly Glu Gln Val Thr Phe Asp
465                 470                 475                 480

Glu Cys Gly Asp Leu Met Gly Asn Tyr Ser Ile Ile Asn Trp His Leu
                485                 490                 495

Ser Pro Glu Asp Gly Ser Ile Val Phe Lys Glu Val Gly Tyr Tyr Asn
            500                 505                 510

Val Tyr Ala Lys Lys Gly Glu Arg Leu Phe Ile Asn Glu Glu Lys Ile
        515                 520                 525

Leu Trp Ser Gly Phe Ser Arg Glu Met Pro Phe Ser Asn Cys Ser Arg
    530                 535                 540

Asp Cys Leu Ala Gly Thr Arg Lys Gly Ile Ile Glu Gly Glu Pro Thr
545                 550                 555                 560

Cys Cys Phe Glu Cys Val Glu Cys Pro Asp Gly Glu Tyr Ser Asp Glu
                565                 570                 575

Thr Asp Ala Ser Ala Cys Asp Lys Cys Pro Asp Asp Phe Trp Ser Asn
            580                 585                 590

Glu Asn His Thr Ser Cys Ile Ala Lys Glu Ile Glu Phe Leu Ser Trp
        595                 600                 605

Thr Glu Pro Phe
    610

<210> SEQ ID NO 16
<211> LENGTH: 553
<212> TYPE: PRT
<213> ORGANISM: Artificial Sequence
<220> FEATURE:
<223> OTHER INFORMATION: Bovine CaSR ECD

<400> SEQUENCE: 16

Met Ala Leu Tyr Ser Cys Cys Trp Ile Leu Leu Ala Phe Ser Thr Trp
1               5                   10                  15

Cys Thr Ser Ala Tyr Gly Pro Asp Gln Arg Ala Gln Lys Lys Gly Asp
            20                  25                  30

Ile Ile Leu Gly Gly Leu Phe Pro Ile His Phe Gly Val Ala Val Lys
        35                  40                  45

Asp Gln Asp Leu Lys Ser Arg Pro Glu Ser Val Glu Cys Ile Arg Tyr
    50                  55                  60

Asn Phe Arg Gly Phe Arg Trp Leu Gln Ala Met Ile Phe Ala Ile Glu
65                  70                  75                  80

Glu Ile Asn Ser Ser Pro Ala Leu Leu Pro Asn Met Thr Leu Gly Tyr
```

-continued

```
                85                  90                  95
Arg Ile Phe Asp Thr Cys Asn Thr Gln Val Ser Tyr Ala Ser Ser Ser
            100                 105                 110

Arg Leu Leu Ser Asn Lys Asn Gln Phe Lys Ser Phe Leu Arg Thr Ile
        115                 120                 125

Pro Asn Asp Glu His Gln Ala Thr Ala Met Ala Asp Ile Ile Glu Tyr
    130                 135                 140

Phe Arg Trp Asn Trp Val Gly Thr Ile Ala Ala Asp Asp Tyr Gly
145                 150                 155                 160

Arg Pro Gly Ile Glu Lys Phe Arg Glu Ala Glu Arg Asp Ile
                165                 170                 175

Cys Ile Asp Phe Ser Glu Leu Ile Ser Gln Tyr Ser Asp Glu Lys
                180                 185                 190

Ile Gln Gln Val Val Glu Val Ile Gln Asn Ser Thr Ala Lys Val Ile
        195                 200                 205

Val Val Phe Ser Ser Gly Pro Asp Leu Glu Pro Leu Ile Lys Glu Ile
    210                 215                 220

Val Arg Arg Asn Ile Thr Gly Arg Ile Trp Leu Ala Ser Glu Ala Trp
225                 230                 235                 240

Ala Ser Ser Ser Leu Ile Ala Met Pro Glu Tyr Phe His Val Val Gly
                245                 250                 255

Gly Thr Ile Gly Phe Gly Leu Lys Ala Gly Gln Ile Pro Gly Phe Arg
            260                 265                 270

Glu Phe Leu Gln Lys Val His Pro Arg Lys Ser Val His Asn Gly Phe
        275                 280                 285

Ala Lys Glu Phe Trp Glu Glu Thr Phe Asn Cys His Leu Gln Glu Gly
    290                 295                 300

Ala Lys Gly Pro Leu Pro Val Asp Thr Phe Leu Arg Gly His Glu Glu
305                 310                 315                 320

Gly Gly Ala Arg Leu Ser Asn Ser Pro Thr Ala Phe Arg Pro Leu Cys
                325                 330                 335

Thr Gly Glu Glu Asn Ile Ser Ser Val Glu Thr Pro Tyr Met Asp Tyr
            340                 345                 350

Thr His Leu Arg Ile Ser Tyr Asn Val Tyr Leu Ala Val Tyr Ser Ile
        355                 360                 365

Ala His Ala Leu Gln Asp Ile Tyr Thr Cys Ile Pro Gly Arg Gly Leu
    370                 375                 380

Phe Thr Asn Gly Ser Cys Ala Asp Ile Lys Lys Val Glu Ala Trp Gln
385                 390                 395                 400

Val Leu Lys His Leu Arg His Leu Asn Phe Thr Ser Asn Met Gly Glu
                405                 410                 415

Gln Val Thr Phe Asp Glu Cys Gly Asp Leu Ala Gly Asn Tyr Ser Ile
            420                 425                 430

Ile Asn Trp His Leu Ser Pro Glu Asp Gly Ser Ile Val Phe Lys Glu
        435                 440                 445

Val Gly Tyr Tyr Asn Val Tyr Ala Lys Lys Gly Glu Arg Leu Phe Ile
    450                 455                 460

Asn Asp Glu Lys Ile Leu Trp Ser Gly Phe Ser Arg Glu Val Pro Phe
465                 470                 475                 480

Ser Asn Cys Ser Arg Asp Cys Leu Ala Gly Thr Arg Lys Gly Ile Ile
                485                 490                 495

Glu Gly Glu Pro Thr Cys Cys Phe Glu Cys Val Glu Cys Pro Asp Gly
            500                 505                 510
```

```
Glu Tyr Ser Asp Glu Thr Asp Ala Ser Ala Cys Asp Lys Cys Pro Asp
            515                 520                 525

Asp Phe Trp Ser Asn Glu Asn His Thr Ser Cys Ile Ala Lys Glu Ile
530                 535                 540

Glu Phe Leu Ser Trp Thr Glu Pro Phe
545                 550

<210> SEQ ID NO 17
<211> LENGTH: 612
<212> TYPE: PRT
<213> ORGANISM: Artificial Sequence
<220> FEATURE:
<223> OTHER INFORMATION: Alpaca CaSR ECD

<400> SEQUENCE: 17

Met Ala Ser Tyr Ser Cys Cys Trp Ile Leu Leu Ala Phe Ala Trp Cys
1               5                   10                  15

Ala Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Met Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
130                 135                 140

Thr Gly Ser Gly Ile Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Tyr Gly Arg Pro Gly Ile Glu
210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln Gln Val Val
                245                 250                 255

Glu Val Ile Gln Asn Ser Thr Ala Lys Val Ile Val Phe Ser Ser
            260                 265                 270

Gly Pro Asp Leu Glu Pro Leu Ile Lys Glu Ile Val Arg Arg Asn Ile
        275                 280                 285

Thr Gly Arg Ile Trp Leu Ala Ser Glu Ala Trp Ala Ser Ser Ser Leu
290                 295                 300

Ile Ala Met Pro Glu Tyr Phe His Val Val Gly Gly Thr Ile Gly Phe
305                 310                 315                 320
```

```
Ala Leu Lys Ala Gly Gln Ile Pro Gly Phe Arg Glu Phe Leu Gln Lys
            325                 330                 335

Val His Pro Arg Lys Ser Val His Asn Gly Phe Ala Lys Glu Phe Trp
            340                 345                 350

Glu Glu Thr Phe Asn Cys His Leu Gln Glu Gly Ala Lys Gly Pro Leu
            355                 360                 365

Pro Val Asp Asn Phe Leu Arg Gly His Glu Glu Gly Gly Arg Thr
370                 375                 380

Ser Asn Ser Ser Thr Ala Phe Arg Pro Leu Cys Thr Gly Asp Glu Asn
385                 390                 395                 400

Ile Ser Ser Val Glu Thr Pro Tyr Met Asp Tyr Thr His Leu Arg Ile
            405                 410                 415

Ser Tyr Asn Val Tyr Leu Ala Val Tyr Ser Ile Ala His Ala Leu Gln
            420                 425                 430

Asp Ile Tyr Thr Cys Ile Pro Gly Arg Gly Leu Phe Thr Asn Gly Ser
            435                 440                 445

Cys Ala Asp Ile Lys Lys Val Glu Ala Trp Gln Val Leu Lys His Leu
    450                 455                 460

Arg His Leu Asn Phe Thr Asn Asn Met Gly Glu Gln Val Thr Phe Asp
465                 470                 475                 480

Glu Cys Gly Asp Leu Ala Gly Asn Tyr Ser Ile Ile Asn Trp His Leu
            485                 490                 495

Ser Pro Glu Asp Gly Ser Ile Val Phe Lys Glu Val Gly Tyr Tyr Asn
            500                 505                 510

Val Tyr Ala Lys Lys Gly Glu Arg Leu Phe Ile Asn Glu Glu Lys Ile
            515                 520                 525

Leu Trp Ser Gly Phe Ser Arg Glu Val Pro Phe Ser Asn Cys Ser Arg
    530                 535                 540

Asp Cys Leu Ala Gly Thr Arg Lys Gly Ile Ile Glu Gly Glu Pro Thr
545                 550                 555                 560

Cys Cys Phe Glu Cys Val Glu Cys Pro Asp Gly Glu Tyr Ser Asp Glu
            565                 570                 575

Thr Asp Ala Ser Ala Cys Asp Lys Cys Pro Asp Asp Phe Trp Ser Asn
            580                 585                 590

Glu Asn His Thr Ser Cys Ile Ala Lys Glu Ile Glu Phe Leu Ser Trp
            595                 600                 605

Thr Glu Pro Phe
    610

<210> SEQ ID NO 18
<211> LENGTH: 622
<212> TYPE: PRT
<213> ORGANISM: Artificial Sequence
<220> FEATURE:
<223> OTHER INFORMATION: pig CaSR ECD

<400> SEQUENCE: 18

Met Ala Phe Ser Ser Cys Cys Trp Ile Leu Leu Ala Leu Thr Trp Cys
1               5                   10                  15

Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
            35                  40                  45

Gln Asn Leu Glu Ser Arg Pro Glu Ser Val Glu Cys Ile Arg Tyr Asn
    50                  55                  60
```

```
Phe Arg Gly Phe Arg Trp Leu Gln Ala Met Ile Phe Ala Ile Glu Glu
 65                  70                  75                  80

Ile Asn Ser Ser Pro Ala Leu Leu Pro Asn Met Thr Leu Gly Tyr Arg
                 85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140

Thr Gly Ser Gly Ile Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Tyr Gly Arg Pro Gly Ile Glu
    210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln Gln Val Val
                245                 250                 255

Glu Val Ile Gln Asn Ser Thr Ala Lys Val Ile Val Phe Ser Ser
            260                 265                 270

Gly Pro Asp Leu Glu Pro Leu Ile Lys Glu Ile Val Arg Arg Asn Ile
        275                 280                 285

Thr Gly Lys Ile Trp Leu Ala Ser Glu Ala Trp Ala Ser Ser Ser Leu
290                 295                 300

Ile Ala Met Pro Glu Tyr Phe His Val Val Gly Gly Thr Ile Gly Phe
305                 310                 315                 320

Ala Leu Lys Ala Gly Gln Ile Pro Gly Phe Arg Glu Phe Leu Gln Lys
                325                 330                 335

Val His Pro Ser Lys Ser Val His Asn Gly Phe Ala Lys Glu Phe Trp
            340                 345                 350

Glu Glu Thr Phe Asn Cys His Leu Gln Glu Gly Ala Lys Gly Pro Leu
        355                 360                 365

Thr Thr Asp Thr Phe Leu Arg Gly His Glu Glu Gly Gly Arg Ile
370                 375                 380

Ser Asn Ser Ser Thr Ala Phe Arg Pro Leu Cys Thr Gly Asp Glu Asn
385                 390                 395                 400

Ile Ser Ser Val Glu Thr Pro Tyr Met Asp Tyr Thr His Leu Arg Ile
                405                 410                 415

Ser Tyr Asn Val Tyr Leu Ala Val Tyr Ser Ile Ala His Ala Leu Gln
            420                 425                 430

Asp Ile Tyr Thr Cys Ile Pro Gly Arg Gly Leu Phe Thr Asn Gly Ser
        435                 440                 445

Cys Ala Asp Ile Lys Lys Val Glu Ala Trp Gln Val Leu Lys His Leu
    450                 455                 460

Arg His Leu Asn Phe Thr Ser Asn Met Gly Glu Gln Val Thr Phe Asp
465                 470                 475                 480
```

-continued

```
Glu Tyr Gly Asp Leu Ala Gly Asn Tyr Ser Ile Ile Asn Trp His Leu
            485             490                 495

Ser Pro Glu Asp Gly Ser Ile Val Phe Lys Glu Val Gly Tyr Tyr Asn
            500             505             510

Val Tyr Ala Lys Lys Gly Glu Arg Leu Phe Ile Asn Glu Glu Lys Ile
        515             520             525

Leu Trp Ser Gly Phe Ser Arg Glu Pro Leu Thr Val Val Leu Pro Ile
    530             535             540

Leu Gln Val Pro Phe Ser Asn Cys Ser Arg Asp Cys Leu Ala Gly Thr
545             550             555                 560

Arg Lys Gly Ile Ile Glu Gly Glu Pro Thr Cys Cys Phe Glu Cys Val
            565             570             575

Glu Cys Pro Asp Gly Glu Tyr Ser Asp Glu Thr Asp Ala Ser Ala Cys
            580             585             590

Asp Lys Cys Pro Asp Asp Phe Trp Ser Asn Glu Asn His Thr Ser Cys
        595             600             605

Ile Ala Lys Glu Ile Glu Phe Leu Ser Trp Thr Glu Pro Phe
    610             615             620
```